United States Patent
Norton et al.

(10) Patent No.: US 11,913,959 B2
(45) Date of Patent: *Feb. 27, 2024

(54) METHODS OF TREATING AND PROGNOSING NONHEMATOPOIETIC MALIGNANT TUMORS

(71) Applicant: Memorial Sloan Kettering Cancer Center, New York, NY (US)

(72) Inventors: Larry Norton, New York, NY (US); Ross Levine, New York, NY (US); Maria Kleppe, New York, NY (US); Elizabeth Comen, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 258 days.

This patent is subject to a terminal disclaimer.

(21) Appl. No.: 17/207,412

(22) Filed: Mar. 19, 2021

(65) Prior Publication Data
US 2021/0263035 A1    Aug. 26, 2021

Related U.S. Application Data

(63) Continuation of application No. 15/533,911, filed as application No. PCT/US2015/064016 on Dec. 4, 2015, now Pat. No. 10,962,543.

(60) Provisional application No. 62/089,148, filed on Dec. 8, 2014.

(51) Int. Cl.
| | | |
|---|---|---|
| C12Q 1/6886 | (2018.01) | |
| G01N 33/574 | (2006.01) | |
| C07K 16/28 | (2006.01) | |
| A61K 31/7068 | (2006.01) | |
| A61K 31/7052 | (2006.01) | |
| A61K 31/52 | (2006.01) | |
| A61K 31/573 | (2006.01) | |
| A61K 31/704 | (2006.01) | |
| A61K 31/7048 | (2006.01) | |
| A61K 31/506 | (2006.01) | |
| A61K 38/17 | (2006.01) | |
| A61K 39/395 | (2006.01) | |
| A61K 45/06 | (2006.01) | |
| A61K 31/00 | (2006.01) | |

(52) U.S. Cl.
CPC ..... *G01N 33/57484* (2013.01); *A61K 31/506* (2013.01); *A61K 31/52* (2013.01); *A61K 31/573* (2013.01); *A61K 31/704* (2013.01); *A61K 31/7048* (2013.01); *A61K 31/7052* (2013.01); *A61K 31/7068* (2013.01); *A61K 38/177* (2013.01); *A61K 39/3955* (2013.01); *A61K 45/06* (2013.01); *C12Q 1/6886* (2013.01); *G01N 33/57496* (2013.01); *A61K 31/00* (2013.01); *C12Q 2600/136* (2013.01); *C12Q 2600/158* (2013.01); *G01N 2800/52* (2013.01); *G01N 2800/56* (2013.01); *G01N 2800/7028* (2013.01)

(58) Field of Classification Search
None
See application file for complete search history.

(56) References Cited

PUBLICATIONS

Nzula et al (Cancer Research, 2003, 63:3275-3280).*
Im et al (Leukemia, 2014, 28:1774-1783).*
Chang et al (BMC Cancer 2013, 13:55).*
Denkert et al (Lancet Oncology, 2018, 19:40-50).*
Connolly et al (Clinical Cancer Research, 2017, 23:2691-2701).*
Howell et al (Pharmaceuticals, 2010, 3:2022-2044).*
Kleppe et al (NPJ Breast Cancer, 2015, 1:15005).*
Juergens et al (Cancer Discovery, 1:2011, 599-607).*

* cited by examiner

*Primary Examiner* — Laura B Goddard
(74) *Attorney, Agent, or Firm* — Brown Rudnick LLP; Ian G. DiBernardo

(57) ABSTRACT

Provided herein are methods of treating a nonhematopoietic malignant tumor in a patient and methods of prognosing a nonhematopoietic malignant tumor in a patient, comprising administering to the patient a therapeutically effective amount of an agent that preferentially kills or inhibits proliferation or activity of leukocytes relative to nonhematopoietic cells.

Figure 1:
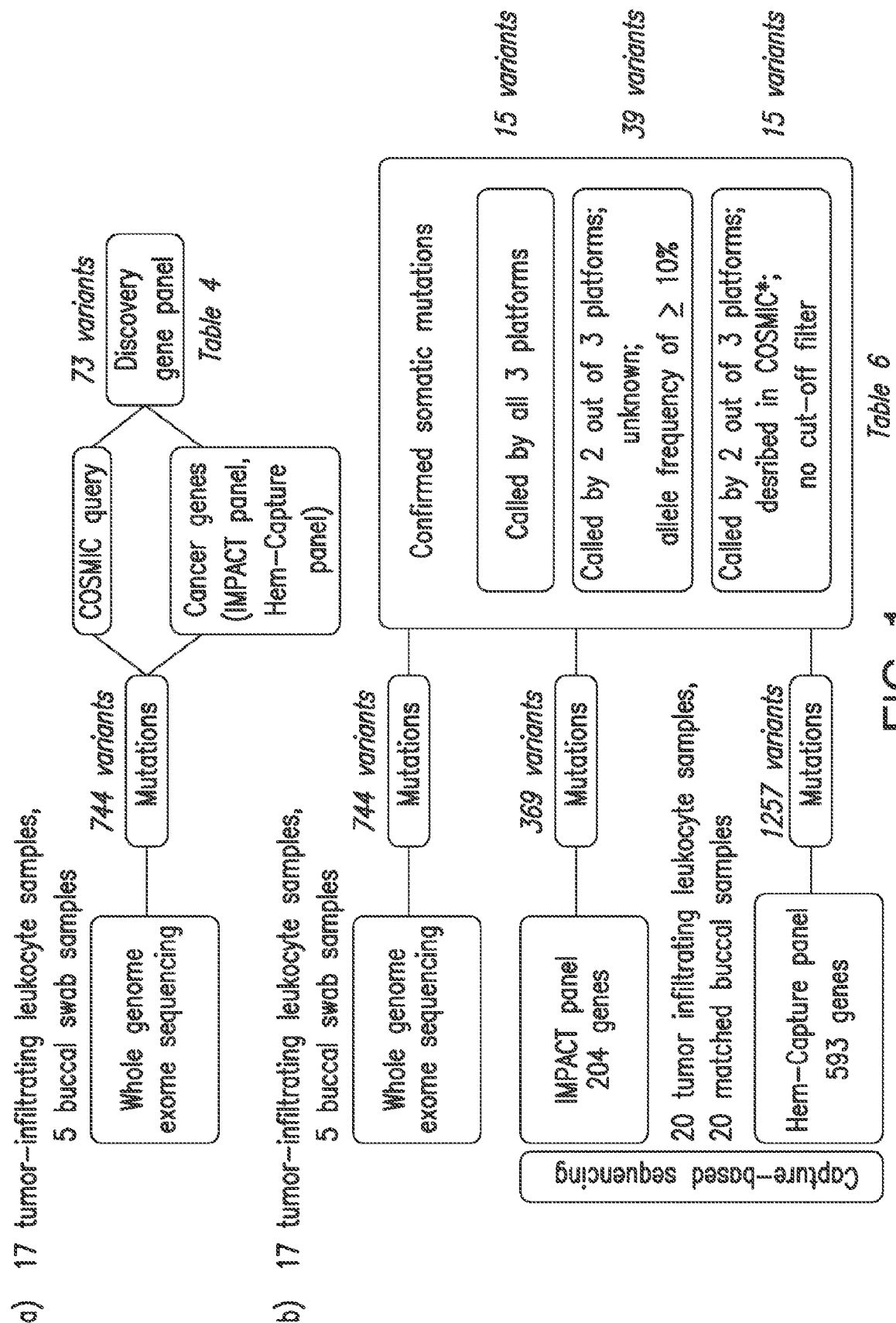

22 Claims, 3 Drawing Sheets
Specification includes a Sequence Listing.

METHODS OF TREATING AND PROGNOSING NONHEMATOPOIETIC MALIGNANT TUMORS

CROSS-REFERENCE TO RELATED APPLICATIONS

This application is a continuation of U.S. patent application Ser. No. 15/533,911, filed Jun. 7, 2017, now U.S. Pat. No. 10,962,543, which is a national stage entry of International Patent Application No. PCT/US2015/064016, filed Dec. 4, 2015, which claims the benefit of U.S. Provisional Application No. 62/089,148, filed Dec. 8, 2014, each of which is incorporated by reference herein in its entirety.

GOVERNMENT RIGHTS STATEMENT

This invention was made with government support under CA008748 awarded by the National Institutes of Health. The government has certain rights in the invention.

REFERENCE TO SEQUENCE LISTING SUBMITTED ELECTRONICALLY

This application incorporates by reference a Sequence Listing submitted with this application as a text file entitled "13542-005-228_Sequence_Listing_ST25.txt" created on Dec. 1, 2015 and having a size of 199 kilobytes.

1. FIELD

Provided herein are methods of treating a nonhematopoietic malignant tumor in a patient and methods of prognosing a nonhematopoietic malignant tumor in a patient.

2. BACKGROUND

In the past decade, candidate gene, exome, and genome sequencing studies have delineated a spectrum of somatic mutations in human malignancies (Cancer Genome Atlas Network, 2012, Nature, 490: 61-70; Ellis, M. J., et al., 2012, Nature, 486: 353-360). These include large-scale sequencing studies in breast cancer, which have identified recurrent mutations in genes and pathways that contribute to malignant transformation and to therapeutic response. Cancer cells interact with their microenvironment, including stromal cell constituents, infiltrating leukocytes, and circulating inflammatory cytokines originating from local and distant sites (Acharyya, S., et al., 2012, Cell, 150: 165-178; Karnoub, A. E., et al., 2007, Nature, 449: 557-563). Previous studies have shown that stromal cells found in breast cancers are characterized by specific mutations and site-specific epigenetic alterations (Kurose, K., et al., 2002, Nat Genet, 32: 355-357; Hu, M., et al., 2005, Nat Genet, 37: 899-905). In addition to tissue-specific stromal cells, circulating and tumor-infiltrating leukocytes can mediate primary tumor growth and metastasis (Granot, Z., et al., 2011, Cancer Cell, 20: 300-314; Grivennikov, S. I., et al., 2010, Cell, 140: 883-899). Recent evidence suggests that tumor-associated stromal cells and infiltrating leukocytes function differently than circulating or bone marrow resident hematopoietic cells (Acharyya, S., et al., 2012, Cell, 150: 165-178; Orimo, A. and Weinberg, R. A., 2006, Cell Cycle, 5: 1597-1601; Li, H. J., et al., 2012, Cancer Discov, 2: 840-855). In particular, several studies have indicated that the content of lymphoid and myeloid cells infiltrating breast cancers correlates with clinical outcome (Mahmoud, S. M., et al., 2011, J Clin Oncol, 29: 1949-1955; Mohammed, Z. M., et al., 2013, Br J Cancer, 109: 1676-1684; Loi, S., et al., 2013, J Clin Oncol, 31: 860-867).

It was recently demonstrated that some older individuals have clinically inapparent, clonal hematopoiesis characterized by recurrent, somatic mutations in TET2 (Busque, L., et al., 2012, Nat Genet, 44: 1179-1181). Tet2 loss in the hematopoietic compartment leads to increased self-renewal and myeloid bias of hematopoietic cells (Moran-Crusio, K., et al., 2011, Cancer Cell, 20: 11-24; Quivoron, C., et al., 2011, Cancer Cell, 20: 25-38; Ko, M., et al., 2011, Proc Natl Acad Sci USA, 108: 14566-14571).

Citation of a reference herein shall not be construed as an admission that such is prior art to the present disclosure.

3. SUMMARY OF THE INVENTION

The present invention provides methods of treating a nonhematopoietic malignant tumor in a patient comprising administering to the patient a therapeutically effective amount of an agent (hereinafter "First Agent") that preferentially kills or inhibits proliferation or activity of leukocytes relative to nonhematopoietic cells.

In specific embodiments, the First Agent is imatinib, daunorubicin, cytarabine, decitabine, azacitidine, etoposide, mercaptopurine, prednisone, idelalisib, ibrutinib, or ABT-199.

In a specific embodiment wherein one or more somatic mutations are present in TET2 in tumor infiltrating leukocytes of the nonhematopoietic malignant tumor, the First Agent is decitabine. In another specific embodiment wherein one or more somatic mutations are present in TET2 in tumor infiltrating leukocytes of the nonhematopoietic malignant tumor, the First Agent is azacitidine. In another specific embodiment wherein one or more somatic mutations are present in IDH2 in tumor infiltrating leukocytes of the nonhematopoietic malignant tumor, the First Agent is decitabine. In another specific embodiment wherein one or more somatic mutations are present in IDH2 in tumor infiltrating leukocytes of the nonhematopoietic malignant tumor, the First Agent is azacitidine.

In various embodiments, the First Agent comprises a leukocyte-specific antibody. In a specific embodiment, the leukocyte-specific antibody is an anti-CD45 antibody. In a specific embodiment, the leukocyte-specific antibody is an anti-CD33 antibody. In a specific embodiment, the leukocyte-specific antibody is an anti-CD20 antibody. In a specific aspect of such an embodiment, the anti-CD20 antibody is rituximab.

In certain embodiments, the leukocyte-specific antibody is conjugated to a cytotoxic drug. In a specific embodiment, the First Agent is an anti-CD33 antibody conjugated to calicheamicin. In a specific aspect of such an embodiment, the anti-CD33 antibody conjugated to calicheamicin is gemtuzumab ozogamicin.

In various embodiments, the method of treating a nonhematopoietic malignant tumor in a patient as described above further comprises administering to the patient another agent (hereinafter "Second Agent"), different from the First Agent, to treat the nonhematopoietic malignant tumor. In specific embodiments, the Second Agent is trastuzumab, lapatinib, fluorouracil, paclitaxel, or a platinum analog. In some embodiments, the Second Agent is an inhibitor of HER2. In a specific aspect of such embodiments, the inhibitor of HER2 is an anti-HER2 antibody (for example, trastuzumab). In another specific aspect of such embodiments, the inhibitor of HER2 is lapatinib.

In specific embodiments, the Second Agent is a broad spectrum cancer treatment. In specific aspects, the broad spectrum cancer treatment is a chemotherapeutic agent. The chemotherapeutic agent can be, but is not limited to, an alkylating agent, an anti-metabolite, an anti-microtubule agent, a topoisomerase inhibitor, a cytotoxic antibiotic, an antibody-drug conjugate, or a combination thereof. In some embodiments, the chemotherapeutic agent is an alkylating agent. In some embodiments, the chemotherapeutic agent is an anti-microtubule agent (for example, a taxane). In some embodiments, the chemotherapeutic agent is a cytotoxic antibiotic (for example, an anthracycline).

In various embodiments, the method of treating a nonhematopoietic malignant tumor in a patient as described above further comprises treating the patient with radiation therapy. In a specific embodiment, the radiation therapy is local radiation therapy. In a specific embodiment, the radiation therapy is involved field radiation therapy.

In various embodiments, the method of treating a nonhematopoietic malignant tumor in a patient as described above further comprises treating the patient by surgically resecting the nonhematopoietic malignant tumor.

In various embodiments wherein the patient has one or more somatic gene mutations present in tumor infiltrating leukocytes of the nonhematopoietic malignant tumor, the method of treating a nonhematopoietic malignant tumor in the patient as described above further comprises prior to the administering step a step of determining that the one or more somatic gene mutations are present in the tumor infiltrating leukocytes.

In certain embodiments, the step of determining comprises comparing the DNA sequence of the tumor infiltrating leukocytes with the DNA sequence of non-cancerous cells. In some embodiments, the step of determining further comprises generating a report that indicates the presence of one or more somatic gene mutations in the tumor infiltrating leukocytes. In a specific aspect of such embodiments, the report further indicates the prognosis of the patient based upon the presence of one or more somatic gene mutations in the tumor infiltrating leukocytes. In some embodiments, the step of determining further comprises communicating the presence of one or more somatic gene mutations in the tumor infiltrating leukocytes. In some embodiments, the step of determining further comprises communicating (i) the presence of one or more somatic gene mutations in the tumor infiltrating leukocytes, and (ii) that the First Agent is a selected or indicated therapy for the patient. In some embodiments, the step of determining further comprises obtaining the tumor infiltrating leukocytes from the tissue of the nonhematopoietic malignant tumor. In some embodiments, the step of determining further comprises extracting DNA from the tumor infiltrating leukocytes. In some embodiments, the step of determining further comprises sequencing the DNA of the tumor infiltrating leukocytes.

The present invention also provides methods of prognosing a nonhematopoietic malignant tumor in a patient comprising determining whether tumor infiltrating leukocytes of the nonhematopoietic malignant tumor have one or more somatic gene mutations, wherein if the tumor infiltrating leukocytes have one or more somatic gene mutations, then the patient is indicated to have a worse prognosis than if the tumor infiltrating leukocytes do not have the one or more somatic gene mutations.

In some embodiments, the method of prognosing the nonhematopoietic malignant tumor further comprises treating the patient with a therapy, wherein the therapy is a more aggressive therapy if the tumor infiltrating leukocytes are determined to have the one or more somatic gene mutations, than if the tumor infiltrating leukocytes do not have the one or more somatic gene mutations.

In certain embodiments, the step of determining whether tumor infiltrating leukocytes of the nonhematopoietic malignant tumor have one or more somatic gene mutations comprises comparing the DNA sequence of the tumor infiltrating leukocytes with the DNA sequence of non-cancerous cells. In some embodiments, the step of determining whether tumor infiltrating leukocytes of the nonhematopoietic malignant tumor have one or more somatic gene mutations further comprises generating a report that indicates the presence or absence of one or more somatic gene mutations in the tumor infiltrating leukocytes. In a specific aspect of such embodiments, the report further indicates the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating (i) the presence or absence of one or more somatic gene mutations in the tumor infiltrating leukocytes, and (ii) the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises obtaining the tumor infiltrating leukocytes from the tissue of the nonhematopoietic malignant tumor. In some embodiments, the step of determining whether tumor infiltrating leukocytes of the nonhematopoietic malignant tumor have one or more somatic gene mutations further comprises extracting DNA from the tumor infiltrating leukocytes. In some embodiments, the step of determining whether tumor infiltrating leukocytes of the nonhematopoietic malignant tumor have one or more somatic gene mutations further comprises sequencing the DNA of the tumor infiltrating leukocytes.

The tumor infiltrating leukocytes in any of the methods described herein can be, but are not limited to, neutrophils, eosinophils, basophils, monocytes, macrophages, and/or lymphocytes.

In various embodiments of the methods described herein, the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, EPHA7, MLL, CYLD, CEBPA, JAK3, ASXL1, KIT, MEF2B, and ERG. In specific embodiments, the one or more somatic gene mutations are present in one or more genes selected from the group consisting of BCOR, NOTCH2, TET2, NF1, EZH2, JAK1, DNMT3A, and TP53. In a specific embodiment, the one or more somatic gene mutations are present in TET2. In a specific embodiment, the one or more somatic gene mutations are present in IDH2.

In specific embodiments, the one or more somatic gene mutations are in a coding region. In one aspect of such embodiments, the one or more somatic mutations result in an amino acid substitution. In another aspect of such embodiments, the one or more somatic gene mutations result in a premature stop codon.

In specific embodiments of the methods described herein, the nonhematopoietic malignant tumor is an epithelial tumor. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor. In specific embodiments of the methods of treating a nonhematopoietic malignant tumor described herein, the nonhematopoietic malignant tumor is an epithelial tumor, and the First Agent preferentially kills or inhibits proliferation or activity of leukocytes relative to epithelial cells.

In a preferred embodiment of the methods described herein, the patient is a human patient.

4. BRIEF DESCRIPTION OF FIGURES

FIG. 1. Summary of the genetic analysis. The diagram outlines the steps used to filter the variants identified by whole-exome sequencing (a) and capture-based sequencing (b). *Indicates variants altering a codon previously reported in Catalogue Of Somatic gene mutations In Cancer (COSMIC) including different substitution of the same amino acid.

Figure 2:
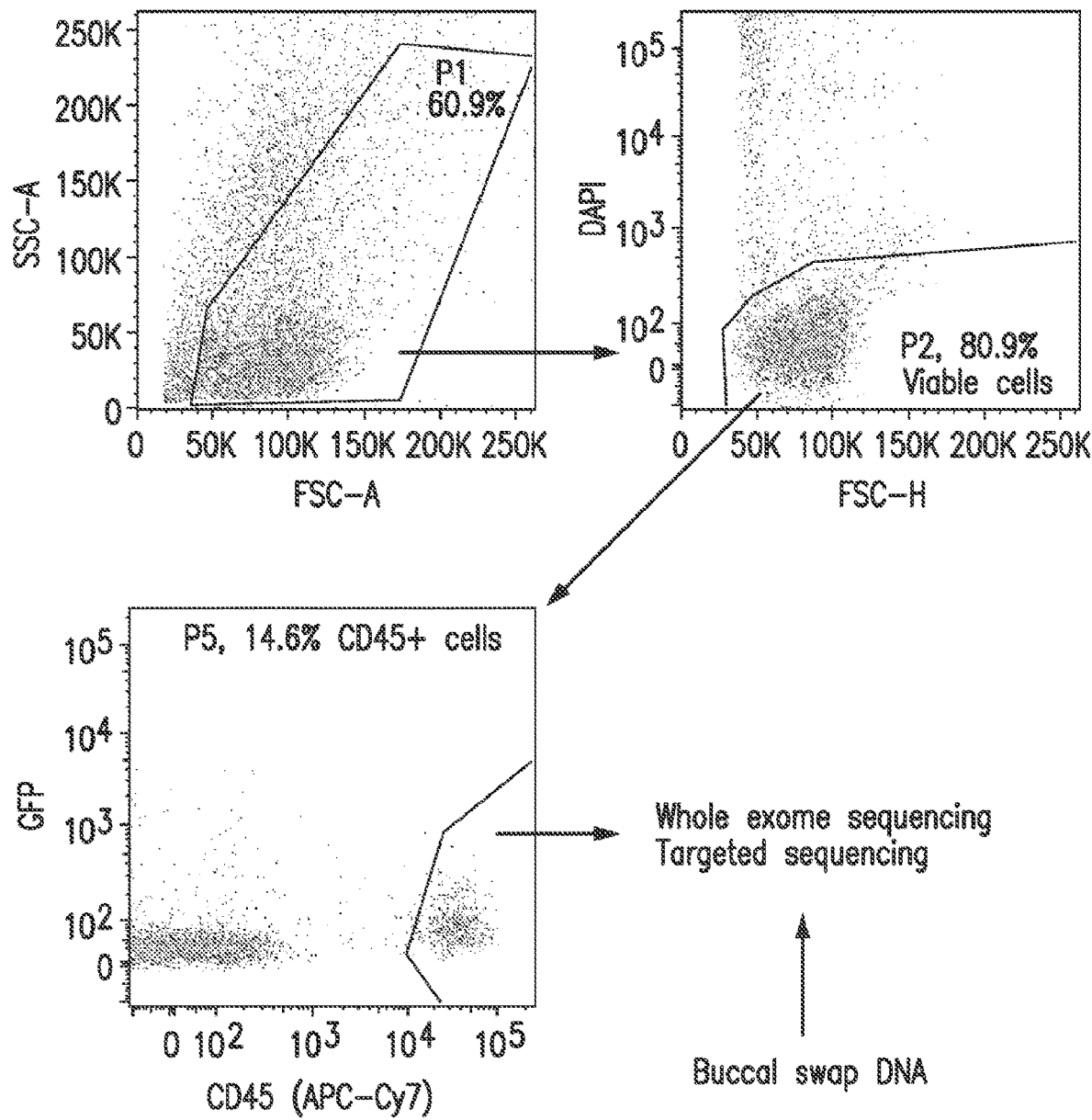
Figure 2:
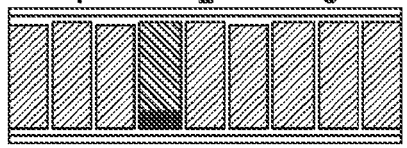
Figure 2:
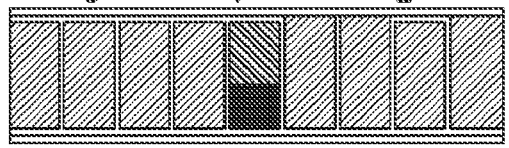
Figure 2:
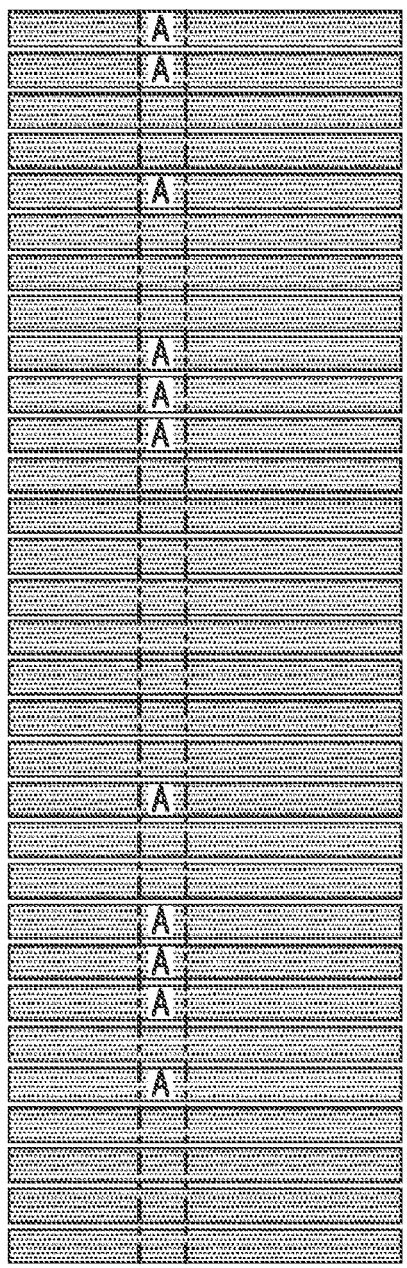
Figure 2:
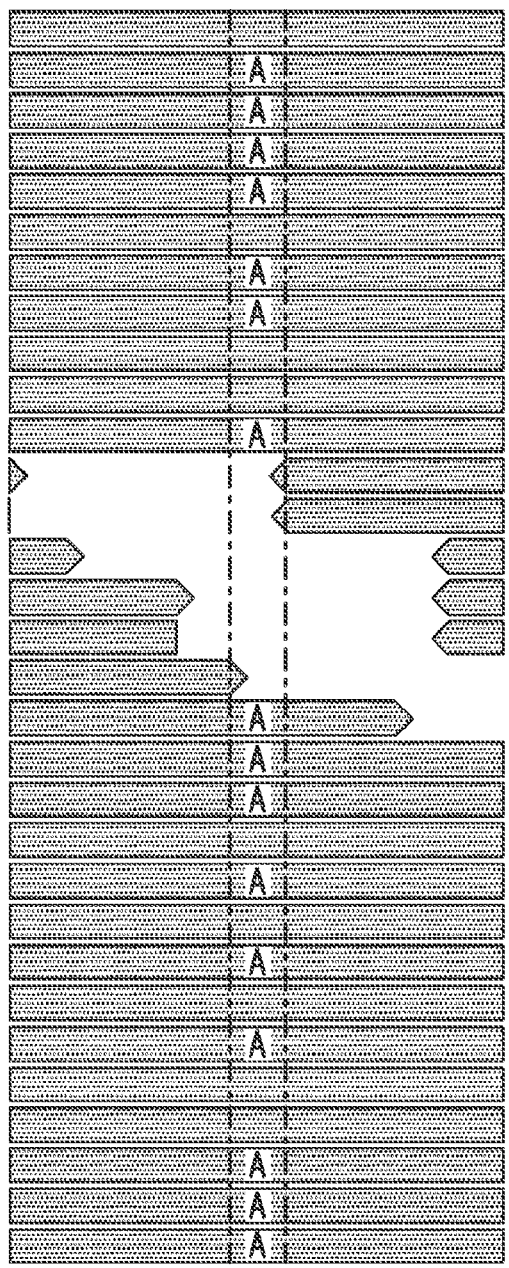

FIG. 2. Sequencing analysis of 21 primary breast cancers identified somatically acquired mutations in tumor-infiltrating leukocytes. (a) Gating scheme for fluorescent-activated cell sorting of CD45-positive hematopoietic cells (Patient #20). DAPI was included as live-dead stain. Cell doublets were excluded prior to gating on PE-Cy7 (not shown). DNA extracted from the CD45-positive fraction was analyzed using three independent sequencing platforms. (b) Representative IGV image showing the presence of acquired mutations. Reads that do not match the reference nucleotide are marked with the substituting nucleobase. Grey bar chart on top displays the read depth. Reference nucleotide and protein sequence are depicted for each mutation. Variant allele frequency (VAF) and the number of altered and total reads are shown (alt|total, VAF).

5. DETAILED DESCRIPTION

The present invention provides methods of treating a nonhematopoietic malignant tumor in a patient and methods of prognosing a nonhematopoietic malignant tumor in a patient. The inventors have discovered that tumor infiltrating leukocytes in some nonhematopoietic malignant tumors have somatically acquired mutations. According to the invention, tumor infiltrating leukocytes are targets in treating a nonhematopoietic malignant tumor and the presence of somatic mutations in tumor infiltrating leukocytes is a prognostic factor in prognosing a nonhematopoietic malignant tumor.

5.1. Methods of Treating a Nonhematopoietic Malignant Tumor

Provided herein are methods of treating a nonhematopoietic malignant tumor in a patient comprising administering to the patient a therapeutically effective amount of an agent (hereinafter "First Agent") that preferentially kills or inhibits proliferation or activity of leukocytes relative to nonhematopoietic cells.

In specific embodiments, the nonhematopoietic malignant tumor is a carcinoma, sarcoma, germ cell tumor, blastoma, or brain tumor. In specific embodiments, the nonhematopoietic malignant tumor is an epithelial tumor, and the First Agent preferentially kills or inhibits proliferation or activity of leukocytes relative to epithelial cells. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor. In a specific embodiment, the nonhematopoietic malignant tumor is a malignant tumor of a particular tissue or organ type, and the First Agent preferentially kills or inhibits proliferation or activity of leukocytes relative to cells of such tissue or organ.

5.1.1. Treatment with the First Agent

The First Agent is any pharmaceutically acceptable agent that preferentially kills or inhibits proliferation or activity of leukocytes relative to nonhematopoietic cells. In various embodiments, the First Agent is an agent that is known or indicated to treat leukemia. In specific embodiments, the First Agent is imatinib, daunorubicin, cytarabine, decitabine, azacitidine, etoposide, mercaptopurine, prednisone, idelalisib, ibrutinib, or ABT-199.

First Agents are any known in the art, or can be identified by known methods. In particular, preferential killing or inhibition of proliferation or activity of leukocytes relative to nonhematopoietic cells can be determined by methods known in the art. As but one example, incubation of leukocytes and nonhematopoietic cells, respectively, with the same amount of candidate First Agent under the same or similar conditions, and detection of the percentage of cell death (or alternatively cell survival) can be carried out to determine whether an agent is a First Agent. Percentage of cell death can be determined, e.g., by use of dyes commonly used to determine cell viability.

In a specific embodiment wherein one or more somatic mutations are present in TET2 in tumor infiltrating leukocytes of the nonhematopoietic malignant tumor, the First Agent is decitabine. In another specific embodiment wherein one or more somatic mutations are present in TET2 in tumor infiltrating leukocytes of the nonhematopoietic malignant tumor, the First Agent is azacitidine. In another specific embodiment wherein one or more somatic mutations are present in IDH2 in tumor infiltrating leukocytes of the nonhematopoietic malignant tumor, the First Agent is decitabine. In another specific embodiment wherein one or more somatic mutations are present in IDH2 in tumor infiltrating leukocytes of the nonhematopoietic malignant tumor, the First Agent is azacitidine.

In various embodiments, the First Agent comprises a leukocyte-specific antibody. In a specific embodiment, the leukocyte-specific antibody is an anti-CD45 antibody. In a specific embodiment, the leukocyte-specific antibody is an anti-CD33 antibody. In a specific embodiment, the leukocyte-specific antibody is an anti-CD20 antibody. In a specific aspect of such an embodiment, the anti-CD20 antibody is rituximab.

In certain embodiments, the leukocyte-specific antibody is conjugated to a cytotoxic drug. In a specific embodiment, the First Agent is an anti-CD33 antibody conjugated to calicheamicin. In a specific aspect of such an embodiment, the anti-CD33 antibody conjugated to calicheamicin is gemtuzumab ozogamicin.

5.1.2. Nonhematopoietic Malignant Tumors Bearing Somatic Mutations in Tumor Infiltrating Leukocytes In various embodiments, the patient has one or more somatic gene mutations present in tumor infiltrating leukocytes of the nonhematopoietic malignant tumor. In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be, but are not limited to, neutrophils, eosinophils, basophils, monocytes, macrophages, and/or lymphocytes.

In specific embodiments, the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, EPHA7, MLL, CYLD, CEBPA, JAK3, ASXL1, KIT, MEF2B, and ERG. In specific embodiments, the one or more somatic gene mutations are present in one or more genes selected from the group consisting of BCOR, NOTCH2, TET2, NF1, EZH2, JAK1, DNMT3A, and TP53. In a specific embodiment, the one or more somatic gene mutations are present in TET2. In a particular embodiment, the one or more somatic gene mutations are present in human TET2, wherein the patient is a human patient. In a specific embodiment, the human TET2 has a wild-type sequence that is SEQ ID NO: 1. In a specific embodiment, the one or more somatic gene mutations are present in IDH2. In a particular embodiment, the one or more somatic gene mutations are present in human IDH2, wherein the patient is a human patient. In a specific embodiment, the human IDH2 has a wild-type sequence that is SEQ ID NO: 2.

In specific embodiments, the one or more somatic gene mutations are in a coding region. In one aspect of such embodiments, the one or more somatic mutations result in an amino acid substitution. In another aspect of such embodiments, the one or more somatic gene mutations result in a premature stop codon. By way of example, in specific embodiments, the one or more somatic mutations result in an amino acid substitution or a premature stop codon as shown in any of Table 4, Table 5, or Table 6.

5.1.3. Combination Therapy

In various embodiments, the method of treating a nonhematopoietic malignant tumor in a patient as described above further comprises administering to the patient another agent (hereinafter "Second Agent"), different from the First Agent, to treat the nonhematopoietic malignant tumor. In certain embodiments, the Second Agent is known or indicated to treat the nonhematopoietic malignant tumor. In a specific embodiment, the second agent preferentially kills or inhibits proliferation or activity of nonhematopoietic cells, e.g., of the same tissue as the nonhematopoietic malignant tumor, relative to leukocytes. In another specific embodiment, the Second Agent kills or inhibits proliferation or activity of leukocytes at about the same potency as it kills or inhibits proliferation or activity of cells of the same tissue as the nonhematopoietic malignant tumor. In specific embodiments, the Second Agent is trastuzumab, lapatinib, fluorouracil, paclitaxel, or a platinum analog. In some embodiments, the Second Agent is an inhibitor of HER2. In a specific aspect of such embodiments, the inhibitor of HER2 is an anti-HER2 antibody (for example, trastuzumab). In another specific aspect of such embodiments, the inhibitor of HER2 is lapatinib.

In specific embodiments, the Second Agent is a broad spectrum cancer treatment. In specific aspects, the broad spectrum cancer treatment is a chemotherapeutic agent. The chemotherapeutic agent can be, but is not limited to, an alkylating agent, an anti-metabolite, an anti-microtubule agent, a topoisomerase inhibitor, a cytotoxic antibiotic, an antibody-drug conjugate, or a combination thereof. In some embodiments, the chemotherapeutic agent is an alkylating agent. In some embodiments, the chemotherapeutic agent is an anti-microtubule agent (for example, an taxane). In some embodiments, the chemotherapeutic agent is a cytotoxic antibiotic (for example, an anthracycline).

In various embodiments, the method of treating a nonhematopoietic malignant tumor in a patient as described above further comprises treating the patient with radiation therapy. In a specific embodiment, the radiation therapy is local radiation therapy. In a specific embodiment, the radiation therapy is involved field radiation therapy.

In various embodiments, the method of treating a nonhematopoietic malignant tumor in a patient as described above further comprises treating the patient by surgically resecting the nonhematopoietic malignant tumor.

5.1.4. Routes of Administration and Dosage

Agents as described above (e.g., First Agent and Second Agent) may be administered to patients by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray.

Furthermore, one may administer the agent(s) described herein or a pharmaceutical composition thereof in a targeted drug delivery system, for example, in a liposome coated with an antibody specific for leukocytes. The liposomes will be targeted to and taken up selectively by the leukocytes.

The amount of agent described herein or a pharmaceutical composition thereof which will be effective in the treatment of the nonhematopoietic tumor will depend on the nature of the disease and the condition of the patient, and can be determined by standard clinical techniques and the knowledge of the physician.

The precise dose and regime to be employed in a composition will also depend on the route of administration, and the seriousness of the tumor, and should be decided according to the judgment of the physician and each patient's circumstance.

5.1.5. Methods of Detecting Somatic Mutations in Tumor Infiltrating Leukocytes.

In various embodiments wherein the patient has one or more somatic gene mutations present in tumor infiltrating leukocytes of the nonhematopoietic malignant tumor, the method of treating a nonhematopoietic malignant tumor in the patient as described above further comprises prior to the administering step a step of determining that the one or more somatic gene mutations are present in the tumor infiltrating leukocytes.

In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be neutrophils, eosinophils, basophils, monocytes, macrophages, and/or lymphocytes. The one or more somatic gene mutations can be present in locations as described above in Sections 5.1.2.

In certain embodiments, the step of determining comprises comparing the DNA sequence of the tumor infiltrating leukocytes with the DNA sequence of non-cancerous cells. In some embodiments, the step of determining further comprises generating a report that indicates the presence of one or more somatic gene mutations in the tumor infiltrating leukocytes. In a specific aspect of such embodiments, the report further indicates the prognosis of the patient based upon the presence of one or more somatic gene mutations in the tumor infiltrating leukocytes. In some embodiments, the step of determining further comprises communicating the presence of one or more somatic gene mutations in the tumor infiltrating leukocytes. In some embodiments, the step of determining further comprises communicating (i) the presence of one or more somatic gene mutations in the tumor infiltrating leukocytes, and (ii) that the First Agent is a selected or indicated therapy for the patient. In some embodiments, the step of determining further comprises obtaining the tumor infiltrating leukocytes from the tissue of the nonhematopoietic malignant tumor. In some embodiments, the step of determining further comprises extracting DNA from the tumor infiltrating leukocytes. In some embodiments, the step of determining further comprises sequencing the DNA of the tumor infiltrating leukocytes.

The tissue of the nonhematopoietic malignant tumor can be obtained by any method known in the art, for example, biopsy or surgical resection.

Obtaining tumor infiltrating leukocytes from the tissue of the nonhematopoietic malignant tumor can be performed by any method known in the art, for example, Fluorescence-Activated Cell Sorting (FACS) to isolate CD45+ cells from a sample(s) of the nonhematopoietic malignant tumor, as described in Example Section 6.1.2.

Extracting DNA from tumor infiltrating leukocytes can be performed by any method known in the art. Non-limiting exemplary methods for extracting DNA include salting-out methods, organic extraction methods, cesium chloride density gradient methods, anion-exchange methods, and silica-based methods (Green, M. R. and Sambrook J., 2012, Molecular Cloning (4th ed.), Cold Spring Harbor, N.Y.: Cold Spring Harbor Laboratory Press; Carpi F. M., et al., 2011, Recent Pat DNA Gene Seq, 5:1-7; Tan, S. C. and Yiap, B. C, 2009, J Biomed Biotechnol, Article ID 574398).

Sequencing the DNA of the tumor infiltrating leukocytes can be performed by any sequencing technologies known in the art. Non-limiting exemplary methods for sequencing of DNA include SOLiD sequencing (Shendure, J., et al., 2005, Science, 309: 1728-1732; McKeman, K. J., et al., 2009, Genome Res, 19: 1527-1541; Berglund, E. G., et al., 2011, Investig Genet, 2: 23; see also the Applied Biosystems website for a complete description of the technology), 454 sequencing (King, C. and Scott-Horton, T., 2008, J Vis Exp, (11): 630; Wheeler, D. A., et al., 2008, Nature, 452: 872-876; Berglund, E. C., et al., 2011, Investig Genet, 2: 23; see also the 454.com website for a complete description of the technology), Illumina (Solexa) sequencing (Bentley, D. R., et al., 2008, Nature, 456: 53-59; Balasubramanian, S., 2011, Chem Commun, 47: 7281-7286; Berglund, E. C., et al., 2011, Investig Genet, 2: 23; see also the Illumina website for a complete description of the technology), Ion Torrent semiconductor sequencing (Rusk, N., 2011, Nat Meth, 8: 44-44), DNA Nanoball sequencing (Porreca, G. J., 2010, Nat Biotechnol, 28: 43-44), Heliscope single molecule sequencing (Thompson, J. F. and Steinmann, K. E., 2010, Curr Protoc Mol Biol, Chapter 7: Unit 7), and single molecule real time (SMRT) sequencing (Eid, J, et al., 2009, Science, 323: 133-138). By way of example, in some embodiments, the step of sequencing the DNA of the tumor infiltrating leukocytes can be performed by whole exome sequencing, target capture sequencing, or a combination thereof, as shown in Example Section 6.1.5. In a specific embodiment, the step of determining further comprises sequencing the DNA of a non-tumorous sample (for example, a buccal swab sample) from the patient to provide a matched germline DNA sequence control, to identify somatic gene mutation(s) in the tumor infiltrating leukocytes.

Generating a report can be manually performed or computer-implemented using a computer system or computer-readable medium. In specific embodiments, the report further indicates the prognosis of the patient based upon the presence of one or more somatic gene mutations in the tumor infiltrating leukocytes. In specific embodiments, the report further indicates the name(s) of the gene(s) that are somatically mutated in the tumor infiltrating leukocytes of the patient. In further specific embodiments, the report further indicates the mutation(s) in the gene(s) that are somatically mutated in the tumor infiltrating leukocytes of the patient.

5.2. Methods of Prognosing a Nonhematopoietic Malignant Tumor

Also provided herein are methods of prognosing a nonhematopoietic malignant tumor in a patient comprising determining whether tumor infiltrating leukocytes of the nonhematopoietic malignant tumor have one or more somatic gene mutations, wherein if the tumor infiltrating leukocytes have one or more somatic gene mutations, then the patient is indicated to have a worse prognosis than if the tumor infiltrating leukocytes do not have the one or more somatic gene mutations.

In specific embodiments, the nonhematopoietic malignant tumor is a carcinoma, sarcoma, germ cell tumor, blastoma, or brain tumor. In specific embodiments, the nonhematopoietic malignant tumor is an epithelial tumor. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor.

In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be, but are not limited to, neutrophils, eosinophils, basophils, monocytes, macrophages, and/or lymphocytes. The one or more somatic gene mutations can be present in locations as described above in Sections 5.1.1.

In some embodiments, the method of prognosing the nonhematopoietic malignant tumor further comprises treating the patient with a therapy, wherein the therapy is a more aggressive therapy (for example, greater drug potency or greater frequency of administration) if the tumor infiltrating leukocytes are determined to have the one or more somatic gene mutations, than if the tumor infiltrating leukocytes do not have the one or more somatic gene mutations. The therapy can be any method of treating a nonhematopoietic malignant tumor as described herein.

In certain embodiments, the step of determining whether tumor infiltrating leukocytes of the nonhematopoietic malignant tumor have one or more somatic gene mutations comprises comparing the DNA sequence of the tumor infiltrating leukocytes with the DNA sequence of non-cancerous cells. In some embodiments, the step of determining whether tumor infiltrating leukocytes of the nonhematopoietic malignant tumor have one or more somatic gene mutations further comprises generating a report that indicates the presence or absence of one or more somatic gene mutations in the tumor infiltrating leukocytes. In a specific aspect of such embodiments, the report further indicates the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating (i) the presence or absence of one or more somatic gene mutations in the tumor infiltrating leukocytes, and (ii) the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises obtaining the tumor infiltrating leukocytes from the tissue of the nonhematopoietic malignant tumor. In some embodiments, the step of determining whether tumor infiltrating leukocytes of the nonhematopoietic malignant tumor have one or more somatic gene mutations further comprises extracting DNA from the tumor infiltrating leukocytes. In some embodiments, the step of determining whether tumor infiltrating leukocytes of the nonhematopoietic malignant tumor have one or more somatic gene mutations further comprises sequencing the DNA of the tumor infiltrating leukocytes.

The tissue of the nonhematopoietic malignant tumor can be obtained using methods described in Section 5.1.5.

Obtaining tumor infiltrating leukocytes from the tissue of the nonhematopoietic malignant tumor, extracting DNA from tumor infiltrating leukocytes, sequencing the DNA of the tumor infiltrating leukocytes, and generating a report can be performed using methods described in Section 5.1.5.

5.3. Patients

The patient referred to in this disclosure, can be, but is not limited to, a human or non-human vertebrate such as a wild, domestic or farm animal. In certain embodiments, the patient is a mammal, e.g., a human, a cow, a dog, a cat, a goat, a horse, a sheep, or a pig. In a preferred embodiment, the patient is a human patient.

In various embodiments, the patient has one or more somatic gene mutations present in tumor infiltrating leukocytes of the nonhematopoietic malignant tumor, as described in Section 5.1.2 above.

In specific embodiments, the patient is under the age of 70. In specific embodiments, the patient is under the age of 60. In specific embodiments, the patient is under the age of 55. In specific embodiments, the patient is under the age of 50.

6. EXAMPLE

This following non-limiting example demonstrates that somatic gene mutations, including in known cancer genes, are present in leukocytes infiltrating breast cancers.

6.1. Methods:

6.1.1. Patient Materials.

Breast cancer samples were collected from consecutive patients with primary triple negative breast cancer (TNBC) who underwent surgery at Memorial-Sloan Kettering Cancer Center (MSKCC) between 2012 and 2013 (Table 1). Patients treated with neoadjuvant chemotherapy were excluded from the study. Non-triple negative breast cancers showing prominent lymphocytic infiltrate in core biopsies were also included. All specimens were sectioned and processed for routine pathological examination. Hematoxylin and eosin (H&E) stained slides were reviewed by breast pathologists to establish the diagnoses. Estrogen receptor (ER), progesterone receptor (PR) and human epidermal growth factor receptor 2 (HER2) status was evaluated by immunohistochemistry (IHC). HER2 fluorescence in situ hybridization (FISH) was performed in one case with equivocal results by IHC. Evaluation of tumor infiltrating leukocytes was performed as previously described (Loi, S., et al., 2013, J Clin Oncol, 31: 860-867). Tumor-infiltrating leukocytes were scored as following: extensive ≥50% infiltration of either stromal or intratumoral lymphocytes; moderate=5-10%; minimal ≤5%. Buccal swab samples were collected from each patient. Mononuclear cells and granulocytes were isolated from peripheral blood following a standard Ficoll protocol. A detailed description on clinicopathological features of each patient is listed in Table 1.

TABLE 1

Summary of clinicopathological features

| ID | Age [y] | Type | TILs# | CD45 [%] | Size [cm] | HG | NG | Mitosis | OG | LVI | LN | ER | PR | HER2 | FISH |
|---|---|---|---|---|---|---|---|---|---|---|---|---|---|---|---|
| 1 | 40 | IDC NOS | Moderate | 36.6 | 2 | 3 | 3 | 3 | 3 | No | No | 0 | 0 | 0 | — |
| 2 | 72 | IDC NOS | Moderate | 11.89 | 1.5 | 3 | 3 | 3 | 3 | No | No | 0 | 0 | 0 | — |
| 3+ | 37 | IDC NOS | Extensive | 12.5 | 4.5 | 3 | 3 | 3 | 3 | No | No | <1% | <1% | 1+ to 2+ | 1.3 |
| 4 | 35 | IDC NOS | Moderate | 0.4 | 5 | 2 | 3 | 3 | 3 | Yes | Yes | 95% | 90% | 3+ | — |
| 5 | 64 | ILC (C/P) | Minimal | 5.0 | 1 | 3 | 3 | 1 | 2 | No | No | 99% | 10% | 1+ | — |
| 6 | 62 | Apocrine | Moderate | 0.6 | 3.3 | 2 | 3 | 2 | 2 | Yes | Yes | 0 | 0 | 0 | — |
| 7 | 83 | IDC NOS | Moderate | 1.4 | 3.1 | 3 | 3 | 2 | 3 | Yes | No | 0 | 0 | 0 | — |
| 8 | 35 | IDC NOS | Moderate | 19.1 | 2.3 | 3 | 3 | 3 | 3 | No | No | 0 | 0 | 0 | — |
| 9 | 39 | IDC NOS | Extensive | 40.95 | 3 | 3 | 3 | 3 | 3 | No | No | 0 | 0 | 1+ | — |

TABLE 1-continued

Summary of clinicopathological features

| ID | Age [y] | Type | TILs# | CD45 [%] | Size [cm] | HG | NG | Mitosis | OG | LVI | LN | ER | PR | HER2 | FISH |
|---|---|---|---|---|---|---|---|---|---|---|---|---|---|---|---|
| 10 | 62 | IDC NOS | Moderate | 7.6 | 1.8 | 3 | 3 | 3 | 3 | Yes | No | 0 | 0 | 1+ | — |
| 11++ | 53 | IDC NOS | Minimal | 0.7 | 1.9 | 3 | 3 | 2 | 3 | No | N/A | 0 | 0 | 1+ | — |
| 12 | 36 | IDC NOS | Extensive | 75.9 | 1.1 | 3 | 3 | 2 | 3 | No | No | 0 | 0 | 0 | — |
| 13 | 88 | Mucinous | Moderate | 0.3 | 6.6 | 2 | 1 | 1 | 1 | No | Yes | 95% | 60% | 0 | — |
| 14 | 56 | IDC NOS | Moderate | 1.4 | 2.5 | 3 | 3 | 3 | 3 | Yes | No | 5% | 5% | 3+ | — |
| 15++ | 65 | IDC NOS | Minimal | 1 | 2.1 | 3 | 3 | 3 | 3 | Yes | N/A | 0 | 5% | 1+ | — |
| 16* | 38 | IDC NOS | Moderate | 0.6 | 2.3 | 3 | 3 | 3 | 3 | No | No | 0 | 0 | 0 | — |
| 17 | 72 | IDC NOS | Moderate | 3 | 1.3 | 3 | 3 | 3 | 3 | No | No | 0 | 0 | 0 | — |
| 18 | 48 | IDC NOS | Moderate | 14.7 | 1.4 | 3 | 2 | 3 | 3 | Yes | No | 0 | 0 | 0 | — |
| 19 | 41 | IDC NOS | Moderate | 37 | 2.4 | 3 | 3 | 3 | 3 | No | No | 0 | 0 | 0 | — |
| 20 | 83 | IDC NOS | Extensive | 11.9 | 2.3 | 3 | 3 | 3 | 3 | No | No | 0 | 0 | 1+ | — |
| 21 | 45 | IDC NOS | Extensive | 77.4 | 0.7 | 3 | 3 | 3 | 3 | No | No | <1% | 10% | 0 | — |

Patient with concurrent astrocytoma (WHO III);
++ipsilateral breast cancer recurrence;
*only whole-exome sequencing data available;
scoring criteria for the level of lymphocytic infiltration are defined above in Section 6.1.1. IDC, invasive ductal carcinoma;
NOS, not otherwise specified;
ILC, invasive lobular carcinoma;
HG, histological grade,
NG, nuclear grade, LVI, lymphovascular invasion;
LN, lymphnode involvement;
ER, estrogen receptor;
PR, progesterone receptor;
HER2, human epidermal growth factor receptor 2, FISH, fluorescence in situ hybridization;
N/A, not sampled;
TILs, tumor infiltrating lymphocytes;
y, year.

6.1.2. Isolation and Processing of Tumor-Infiltrating Cells.

All patients included in this study gave informed consent. Fresh tumor cells, stromal cells, and tumor-infiltrating leukocytes were dissociated from the primary tumors by scraping the cutting surface 5-10 times with a surgical scalpel blade. Cell material was collected by rinsing the blade in PBS. Cells were spun down and resuspended in red cell lysis buffer to remove red blood cells prior to staining with an anti-human CD45-PE-Cy7 or CD45-APC-Cy7 conjugated flow antibody in FACS buffer (PBS supplemented with 2% BSA). Cells were stained for 20 min in the dark at room temperature, washed once with FACS buffer, and passed through a filter. DAPI was added before sorting to discriminate live and dead cells. CD45-positive cells were then purified using a FACSAriaIII Cell Sorter (MSKCC Flow Core Facility).

6.1.3. Laser Capture Microdissection of Tumor Cells.

Ten consecutive 8-μm-thick nuclear fast red-stained representative sections of the tumors were subjected to laser-assisted microdissection on a PALM Robot MicroBeam laser microdissection system, as previously described (Westbury, C. B., et al., 2009, J Pathol, 219: 131-140). First, non-neoplastic cells, including inflammatory cells, stroma and normal breast, were ablated. We subsequently microdissected only histologically unequivocal neoplastic cells from each sample under a microscope. Tissue was microdissected directly into extraction buffer, and DNA was extracted using the DNeasy Blood and Tissue Kit (Qiagen, Valencia, Calif.) and quantified with the Qubit Fluorometer (Invitrogen, Life Technologies, Norwalk, Conn.).

6.1.4. DNA Extraction and Whole Genome Amplification.

DNA was extracted using the QiaAmp DNA kit (Qiagen) following the manufacture instructions. Buccal swabs were processed using the QiaAmp DNA Mini kit (Qiagen) following the manufacture instructions. The quality of DNA samples was analyzed with the Agilent Bioanalyzer 2100. Samples with insufficient amount of DNA (<500 ng) were whole genome amplified (WGA) using the REPLI-g Mini kit (Qiagen) prior to further use in downstream applications. QPCR was performed to assess quality of WGA DNA.

6.1.5. Whole Exome Sequencing and Target Capture Sequencing.

DNA extracted from sorted CD45-positive tumor-infiltrating leukocytes and buccal swabs (Table 2) was sheared to an average size of 180 bp+/−80 bp for whole exome sequencing. For DNA library preparation, 200-250 bp fragments were selected and subjected to PCR amplification. The library was then hybridized to the Agilent SureSelect Human All Exon Kit and sequencing was performed on the SOLiD 3plus or SOLiD 4. Targeted sequencing of tumor infiltrating leukocytes and matched germline DNA of each patient was performed as previously described (Welch, J. S., et al., 2012, Cell, 150: 264-278).

TABLE 2

Mean target coverage information

| | | Mean target coverage | | |
|---|---|---|---|---|
| Sample source | Sample | IMPACT | Hem/600 | Exome |
| CD45+ cells | 1 | 99.81 | 91.48 | 39.70 |
| | 2 | 218.98 | 243.69 | 75.16 |
| | 3 | 358.14 | 392.53 | 66.93 |
| | 4 | 379.38 | 388.45 | 158.95 |
| | 5 | 386.30 | 345.25 | 84.95 |
| | 6 | 263.18 | 258.14 | 89.55 |
| | 7 | 417.28 | 413.19 | 123.42 |
| | 8 | 476.70 | 470.42 | 86.71 |
| | 9 | 375.74 | 388.05 | 120.25 |
| | 10 | 484.63 | 472.99 | 145.36 |
| | 11 | 319.04 | 411.89 | 150.99 |
| | 12 | 372.20 | 472.96 | 143.46 |
| | 13 | 457.35 | 530.77 | 176.98 |
| | 14 | 442.33 | 506.16 | 142.88 |

TABLE 2-continued

Mean target coverage information

| Sample source | Sample | IMPACT | Hem/600 | Exome |
|---|---|---|---|---|
| | 15 | 459.61 | 550.16 | 150.23 |
| | 16 | —* | —* | 155.18 |
| | 17 | 431.70 | 515.91 | 159.63 |
| | 18 | 799.54 | 502.30 | —* |
| | 19 | 463.57 | 609.66 | —* |
| | 20 | 778.25 | 595.60 | —* |
| | 21 | 435.52 | 516.34 | —* |
| Germline control | 1 | 219.87 | 354.11 | 110.69 |
| | 2 | 68.86 | 127.06 | —* |
| | 3 | 228.57 | 383.17 | 138.63 |
| | 4 | 182.19 | 273.96 | —* |
| | 5 | 260.48 | 377.91 | 136.01 |
| | 6 | 333.29 | 449.72 | —* |
| | 7 | 59.82 | 28.49 | —* |
| | 8 | 262.09 | 326.85 | 124.31 |
| | 9 | 176.59 | 242.46 | —* |
| | 10 | 283.65 | 274.74 | —* |
| | 11 | 321.25 | 706.71 | —* |
| | 12 | 228.89 | 499.60 | —* |
| | 13† | 2.49 | 3.76 | —* |
| | 14 | 262.84 | 479.45 | 115.57 |
| | 15 | 112.34 | 205.98 | —* |
| | 17 | 283.08 | 553.12 | —* |
| | 18 | 299.22 | 677.35 | —* |
| | 19 | 331.03 | 680.13 | —* |
| | 20 | 307.91 | 458.01 | —* |
| | 21 | 268.68 | 520.76 | —* |

*Samples were not run at the indicated sequencing platform.
†CD45-positive sample of patient #13 was compared against pooled buccal swab samples due to low coverage of the matching germline DNA sample.

6.1.6. 454 Deep Sequencing Analysis.

Sequence reactions were performed on DNA extracted from mononuclear cells, granulocytes, laser capture microdissected tumor cells, and tumor-infiltrating leukocytes. All PCR reactions were performed using amplicon specific fusion primers. Fusion primers contained next to the template specific sequence a directional primer at the 5'-prime end followed by a multiplex identifier for barcode sample identification. Samples from 6-8 different patients were mixed, processed for 454 deep sequencing, and run on a Genome Sequencer FLX instrument. Data was mapped with BWA MEM (ver 0.7.4) to the full human genome. Multiple mapping reads (MAPQ=0) were removed and then the BAM files were processed for base recalibration using the GATK toolkit (ver 3.1). Mutations were called using the Haplotype caller which found only two events. In addition the read pileups were counted at each of the known mutation sites for each sample to compute the actual depth of both the reference and variant allele and to compute the non-reference allele frequency for each site.

6.1.7. Variant Detection.

Paired-end reads were aligned to the human hg19 genome with BWA 0.6.2-r126 (Iyer, G., et al., 2012, Science, 338: 221). Local realignment at indel regions and baseQ raclibration was done using the GATK suite version 2.8-1 and following recommendations of its authors (McKenna, A., et al, 2010, Genome Res, 20: 1297-1303). Variants in the targeted tumor-normal sample pairs were called with MuTect version 1.1.4. Variants passing the MuTect filters were annotated as high confidence (HC). Variants that were detected by the algorithm, but which failed to pass the MuTect filters were annotated as low confidence (LC). For whole-exome sequencing samples, SNPs and indels were called with the HaplotypeCaller from the GATK suite version 2.8-1. Variants that passed the GATK recommended filters and were not reported in any of the two buccal samples that were analyzed through the same pipeline or found in two or more non-somatic databases (non clinical variants from dbSNP, NHLBI exome sequencing project, and our own internal collection of normal tissues) were annotated as HC. Other variants were reported as LC.

6.1.8. Data Analysis.

A summary of the genetic analysis is depicted in FIG. 1. Briefly, for whole-exome sequencing samples, somatic variants (see Section 6.1.7) were further filtered against the Hem-Capture gene panel (Table 3) and IMPACT panel gene list to identify genes previously reported in hematological and epithelial malignancies, respectively. Identified variants occurring with a frequency ≥10% are shown in Table 4. No cut-off filter was applied to variants which were previously described in COSMIC (Catalogue Of Somatic Mutations In Cancer). Variants confirmed by three sequencing platforms were considered as somatic mutations independent of the allele frequency. In contrast, variants detected by two platforms were only considered somatic when occurring with an allele frequency of 10% or higher with the exception of variants previously described in COSMIC (no cut-off applied) (Table 5 and Table 6).

TABLE 3

Genes targeted by Hem-Capture sequencing panel

| Gene | | | | | | |
|---|---|---|---|---|---|---|
| ABL1 | BAALC | CD200 | DCLRE1C | FAM10A4 | HIC1 | IRAK1 |
| AAMP | BAP1 | CD274 | DDX3X | FAM46C | HIST1H1B | IRAK4 |
| ABCA1 | BCL10 | CD36 | DEPDC5 | FAM84B | HIST1H1C | IRF4 |
| ABCA4 | BCL11A | CD58 | DHCR7 | FANCL | HIST1H1E | IRF8 |
| ABCA7 | BCL11B | CD70 | DIS3 | FAS | HIST1H2AG | ITK |
| ABCD2 | BCL2 | CD79A | DLEU1 | FAT2 | HIST1H2AL | ITPKB |
| ACTB | BCL2L10 | CD79NB | DLEU2 | FBXO31 | HIST1H2BC | JAK1 |
| ACTR3 | BCL2L11 | CD99 | DLEU7 | FBXW7 | HIST1H2BE | JAK2 |
| ADAMTSL3 | BCL6 | CDH13 | DMD | FDFT1 | HIST1H2BG | JAK3 |
| ADARB2 | BCL7A | CDK4 | DNM2 | FDX1 | HIST1H2BK | JAKMIP2 |
| AFAP1 | BCOR | CDK6 | DNMT3A | FGA | HIST1H2BO | JMJD1C |
| AGTR1 | BCORL1 | CDKN2A | DOT1L | FGFR3 | HIST1H3B | JMJD4 |
| AIM1 | BCR | CDKN2B | DPYD | FGG | HLA-A | KANK2 |
| AKAP6 | BIRC2 | CDKN2C | DSC3 | FGR | HLA-B | KCNRG |
| AKAP8 | BIRC3 | CEBPA | DTX1 | FHIT | HMCN1 | KDM2B |
| AKT1 | BLK | CHD1 | DUSP2 | FLT3 | HMGB1 | KDM4C |
| ALK | BLNK | CHD2 | DUSP22 | FLYWCH1 | HNF1B | KDM5C |
| ALOX12B | BMI1 | CHD7 | DUSP27 | FOXO1 | HNRNPA1 | KDM6A |
| ANKLE2 | BNC2 | CHD9 | DUSP9 | FOXP1 | HNRNPR | KDSR |

TABLE 3-continued

Genes targeted by Hem-Capture sequencing panel

| Gene | | | | | | |
|---|---|---|---|---|---|---|
| ANKRD11 | BPTF | CIITA | DYRK1A | FREM2 | HRAS | KIF1B |
| ANP32E | BRAF | CKS1B | EAF2 | FRK | hsa-mir-15a | KIT |
| APOBEC2 | BRPF1 | CLEC16A | EBF1 | FUBP1 | hsa-mir-16-1 | KLF2 |
| ARHGAP1 | BRSK1 | CLTC | ECT2L | FYN | HUWE1 | KLHL6 |
| ARHGAP24 | BTG1 | CNOT3 | EED | GABRA1 | HYDIN | KLHL9 |
| ARHGAP32 | BTG2 | CNTN4 | EGFR | GALNTL6 | ID3 | KRAS |
| ARID1A | BTLA | COL4A2 | EGR1 | GATA2 | IDH1 | KRTAP5-5 |
| ARID1B | BTRC | CPS1 | EGR2 | GATA3 | IDH2 | L2HGDH |
| ARMC2 | C12orf35 | CREB1 | EIF3B | GJA3 | IGF2BP3 | LAMA5 |
| ARPP21 | C16orf48 | CREBBP | ELP2 | GNA13 | IGHV | LATS1 |
| ARSB | C20orf94 | CRLF2 | EP300 | GOLGA3 | IGSF3 | LATS2 |
| ASAP1 | C4orf14 | CSF3R | EPHA7 | GPR110 | IKBIP | LCK |
| ASMTL | C9orf53 | CSMD3 | EPOR | GPS2 | IKBKB | LEF1 |
| ASXL1 | CAMTA1 | CTCF | ERAP1 | GRB2 | IKZF1 | LMO2 |
| ASXL2 | CARD11 | CTGF | ERG | GRID1 | IKZF2 | LOC100130503 |
| ASXL3 | CBL | CTNNA1 | ESCO1 | GRIK2 | IKZF3 | LOC400128 |
| ATF7IP | CCBE1 | CTNNA3 | ESCO2 | GTSE1 | IL10RA | LOC440742 |
| ATG5 | CCDC102B | CTNNB1 | ETS1 | H1FOO | IL15 | LOXL2 |
| ATIC | CCDC132 | CUL4A | ETV6 | HACE1 | IL1RAP | LPHN2 |
| ATM | CCDC26 | CYLC2 | EXOSC6 | HCK | IL3RA | LPHN3 |
| ATP10A | CCNC | CYLD | EZH2 | HDAC4 | IL7R | LPP |
| ATRX | CCND1 | D2HGDH | F3 | HDAC7 | IL8 | LRP1B |
| ATXN1 | CCND2 | DCC | F5 | HERC1 | IMMP2L | LRRIQ3 |
| B2M | CCND3 | DCHS1 | FAF1 | HHEX | ING1 | LRRK2 |
| LYN | MTMR8 | PATL2 | RAF1 | SMARCA1 | TCF7L2 | TTLL7 |
| MAF | MTOR | PAX5 | RAG1 | SMARCA4 | TCL1A | TUSC3 |
| MAFB | MUC16 | PCBP1 | RAG2 | SMARCB1 | TDRD6 | TYK2 |
| MAGEC3 | MUC2 | PCDH7 | RAPGEF1 | SMC1A | TENM2 | U2AF1 |
| MAGED1 | MUC4 | PCDHB6 | RASGEF1A | SMC3 | TET1 | U2AF2 |
| MALT1 | MYB | PCLO | RB1 | SMYD1 | TET2 | UBE2A |
| MAP2 | MYBL2 | PDCD11 | RCOR1 | SND1 | TET3 | UNC5C |
| MAP2K2 | MYC | PDCD1LG2 | RDX | SNX25 | TFG | UNC5D |
| MAP3K1 | MYD88 | PDGFC | REL | SOCS1 | TFPI | VPS8 |
| MAP3K14 | MYO18A | PDS5B | RELN | SOCS2 | TGM7 | VRK2 |
| MAP3K2 | MYO1G | PEAK1 | REV3L | SOX4 | THADA | WAC |
| MAP3K7 | MYOM2 | PFAS | RGAG1 | SP100 | TLL2 | WDR7 |
| MAPK1 | NARS | PGAM5 | RGS12 | SPEN | TLR2 | WDR90 |
| MAPK14 | NBPF1 | PHF6 | RHOH | SPG11 | TLR4 | WHAMM |
| MBNL1 | NCOR1 | PI4K2B | RIMS2 | SPI1 | TLR5 | WHSC1 |
| MC4R | NCOR2 | PIGN | RIPK4 | SPIB | TLR6 | WHSC1L1 |
| MCL1 | NDST4 | PIK3C2B | RNASEH2B | SPRED1 | TMEM30A | WT1 |
| MCPH1 | NEB | PIK3CA | RNF213 | SRC | TMSL3 | WWOX |
| MCRS1 | NF1 | PIK3CD | RPL10 | SRCAP | TMX3 | XBP1 |
| MDM2 | NFATC1 | PIK3CG | RPL5 | SRPX | TNF | XPO1 |
| MDM4 | NFKB1 | PIK3R1 | RPS6KA1 | SRSF1 | TNFAIP3 | YY1AP1 |
| MED12L | NFKBIA | PIM1 | RREB1 | SRSF2 | TNFRSF11A | ZEB2 |
| MEF2B | NFKBIE | PKDCC | RUNX1 | SRSF7 | TNFRSF14 | ZFHX3 |
| MEF2C | NFKBIZ | PKHD1L1 | S1PR2 | STAG1 | TNFRSF1A | ZFP36L1 |
| MIR17HG | NIPBL | PLEKHG1 | SAMD9 | STAG2 | TNFSF9 | ZIC4 |
| MK167 | NKX2-1 | PLEKHG5 | SCMH1 | STAT3 | TOP2A | ZMYM2 |
| MKKS | NOTCH1 | PMS1 | SERPINA1 | STAT5A | TOX | ZMYM3 |
| MLL | NOTCH2 | PNRC1 | SESN1 | STAT5B | TP53 | ZNF343 |
| MLL2 | NPM1 | POT1 | SET | STAT6 | TP53INP1 | ZNF521 |
| MLL3 | NR3C1 | POU2F2 | SETBP1 | STIM2 | TP63 | ZNF541 |
| MLL4 | NR3C2 | PPP2R1B | SETD2 | STS | TP73 | ZNF830 |
| MLL5 | NRAS | PPP2R5A | SF1 | SUZ12 | TPM3 | ZNF85 |
| MOB3A | NRXN3 | PRAME | SF3A1 | SWAP70 | TRAF2 | ZRSR2 |
| MOB3B | NUP214 | PRDM1 | SF3B1 | SYK | TRAF3 | ZWILCH |
| MPL | NXF1 | PRDM2 | SGK1 | SYN2 | TRAF5 | |
| MSH6 | OFD1 | PRKCZ | SH2B3 | TACC2 | TRG@ | |
| MSI1 | OR6K3 | PRKDC | SI | TAF1 | TRIM13 | |
| MSI2 | P2RY8 | PROX1 | SIN3A | TAL1 | TRIM69 | |
| MSL2 | PABPC1 | PRPF40B | SLC25A6 | TBL1XR1 | TRO | |
| MSR1 | PABPC4L | PTEN | SLC38A8 | TCF12 | TRRAP | |
| MSRA | PAG1 | PTPN11 | SLC4A10 | TCF3 | TSC22D1 | |
| MTAP | PAPOLG | PTPN2 | SLC8A1 | TCF4 | TTC18 | |
| MTCP1 | PASD1 | RAD21 | SLITRK6 | TCF7 | TTC28 | |

TABLE 4

Discovery variants identified by exome sequencing

| Sample | Gene | Mutation | Allele | Refseq Prot ID |
|---|---|---|---|---|
| 1 | KDM5C | p.A612T | 0.23 | NP 004178 |
| 2 | KDM5C | p.A612T | 0.47 | NP 004178 |
|  | CDK8 | p.V169I | 0.32 | NP 001251 |
|  | MPL | p.E54V | 0.2 | NP 005364 |
|  | ARID1A | p.Q1365K | 0.18 | NP 006006 |
|  | FLT3 | p.Q394* | 0.18 | NP 004110 |
|  | FGFR1 | p.G205D | 0.14 | NP 075598 |
|  | JAK1 | p.S260G | 0.13 | NP 002218 |
|  | GLI1 | p.G162C | 0.11 | NP 005260 |
| 3 | EZH2 | p.A478S | 0.46 | NP 004447 |
|  | EP300 | p.Q2355L | 0.33 | NP 001420 |
|  | EP300 | p.M1972T | 0.24 | NP 001420 |
| 4 | BCOR | p.P1156L | 0.46 | NP 001116857 |
|  | NF1 | p.K1517M | 0.32 | NP 001035957 |
|  | NF1 | p.A1670V | 0.25 | NP 001035957 |
|  | SMARCB1 | p.N154K | 0.14 | NP 003064 |
|  | EPHA10 | p.L80Q | 0.13 | NP 001092909 |
| 5 | IRF4 | p.M146I | 0.73 | NP 002451 |
|  | INSR | p.R162S | 0.53 | NP 000199 |
|  | EPHA2 | p.E302G | 0.2 | NP 004422 |
|  | SMO | p.A379V | 0.2 | NP 005622 |
|  | DUSP27 | p.Q737L | 0.12 | NP 001073895 |
| 6 | NOTCH2 | p.P1101T | 0.26 | NP 077719 |
|  | HNF1A | p.A562V | 0.18 | NP 000536 |
| 7 | MYO18A | p.A958V | 1 | NP 510880 |
|  | MET | p.Q165K | 0.2 | NP 000236 |
| 9 | RPTOR | p.V476M | 0.5 | NP 065812 |
| 10 | NOTCH2 | p.S1708P | 0.73 | NP 077719 |
|  | ATP10A | p.P35A | 0.51 | NP 077816 |
|  | PTCH1 | p.1685M | 0.41 | NP 000255 |
| 11 | IRF4 | p.A370V | 0.43 | NP 002451 |
|  | NF1 | p.N2775S | 0.43 | NP 001035957 |
|  | FGFR1 | p.M731V | 0.34 | NP 075598 |
| 12 | BRCA1 | p.S1613G | 0.99 | NP 009225 |
|  | NCOR2 | p.A1706T | 0.56 | NP 001070729 |
|  | DUSP27 | p.T1124N | 0.46 | NP 001073895 |
|  | PASD1 | p.Q213E | 0.23 | NP 775764 |
|  | BCOR | p.P1648L | 0.41 | NP 001116857 |
| 13 | NEB | p.Y1092C | 0.51 | NP 004534 |
|  | MUC4 | p.A2025V | 0.45 | NP 060876 |
|  | NOTCH2 | p.A21T | 0.35 | NP 077719 |
|  | POU2F2 | p.L459F | 0.25 | NP 002689 |
|  | HLA-A | p.A270S | 0.22 | NP 002107 |
|  | ALK | p.H1030P | 0.19 | NP 004295 |
|  | HLA-A | p.E176V | 0.18 | NP 002107 |
|  | TET2 | p.E1874K | 0.16 | NP 001120680 |
| 14 | HLA-B | p.R155S | 0.8 | NP 005505 |
|  | FGFR4 | p.S776F | 0.56 | NP 002002 |
|  | GATA2 | p.A286P | 0.46 | NP 001139133 |
|  | HLA-A | p.E176V | 0.41 | NP 002107 |
|  | ALK | p.H1030P | 0.16 | NP 004295 |
| 15 | HLA-B | p.R155S | 0.74 | NP 005505 |
|  | FLT1 | p.V1331I | 0.56 | NP 002010 |
|  | ATM | p.R2105S | 0.45 | NP 000042 |
|  | POU2F2 | p.L459F | 0.24 | NP 002689 |
|  | ALK | p.H1030P | 0.17 | NP 004295 |
| 16 | HLA-A | p.E176V | 0.83 | NP 002107 |
|  | HLA-B | p.R155S | 0.52 | NP 005505 |
|  | ITK | p.D510N | 0.48 | NP 005537 |
|  | FREM2 | p.G1608D | 0.45 | NP 997244 |
|  | INPP4B | p.K816E | 0.44 | NP 003857 |
|  | CSF1R | p.R216Q | 0.41 | NP 005202 |
|  | PIGN | p.T569N | 0.38 | NP 789744 |
|  | SOX17 | p.G178R | 0.38 | NP 071899 |
|  | POU2F2 | p.L459F | 0.28 | NP 002689 |
| 17 | HLA-A | p.E176V | 0.6 | NP 002107 |
|  | MLL4 | p.S214P | 0.59 | NP 055542 |
|  | TTC28 | p.K2346Q | 0.54 | NP 001138890 |
|  | TNFSF9 | p.A58S | 0.51 | NP 003802 |
|  | TRRAP | p.S1073G | 0.46 | NP 003487 |
|  | HLA-B | p.R155S | 0.32 | NP 005505 |
|  | NOTCH2 | p.A21T | 0.23 | NP 077719 |
|  | ALK | p.H1030P | 0.18 | NP 004295 |

TABLE 5

Somatic mutations in known cancer genes

| Sample | Gene | Mutation | Frequency | Refseq Prot Id |
|---|---|---|---|---|
| 1 | EP300 | p.G1777C | 0.06 | NP 001420 |
| 2 | DNMT3A | p.Y533C | 0.185 | NP 783328 |
| 3 | EZH2 | p.A483S | 0.46 | NP 004447 |
|  | IDH2 | p.W164L | 0.13 | NP 002159 |
|  | DNMT3A | p.T260N | 0.1 | NP 783328 |
|  | TP53 | p.M1691 | 0.029 | NP 001119585 |
| 4 | BCOR | p.P1156L | 0.49 | NP 001116857 |
|  | EPHA7 | p.G592S | 0.14 | NP 004431 |
|  | WT1 | p.T278I | 0.11 | NP 000369 |
|  | TET2 | p.Q1702* | 0.06 | NP 001120680 |
|  | PNRC1 | p.R97Q | 0.048 | NP 006804 |
|  | EGFR | p.A871E | 0.042 | NP 005219 |
| 5 | ALK | p.R1209Q | 0.21 | NP 004295 |
|  | ETV6 | p.P25S | 0.038 | NP 001978 |
| 6 | IDH2 | p.K205R | 0.245 | NP 002159 |
|  | NOTCH2 | p.P1101T | 0.18 | NP 077719 |
|  | NF1 | p.Q2434H | 0.099 | NP 001035957 |
|  | SMARCA4 | p.D694E | 0.087 | NP 003063 |
| 12 | BCOR | p.P1613L | 0.483 | NP 001116857 |
| 13 | TET2 | p.E1874K | 0.17 | NP 001120680 |

Mutations listed in this table were identified by two or three independent platforms with an allele frequency of ≥10%. Mutations occurring at a lower frequency were included if previously reported in COSMIC.

TABLE 6

Somatic variants identified by at least two platforms

| Sample | Gene | Mutation | Chr | Position | Ref | Alt | IMPACT | Hem | Exome | Refseq_ProtID |
|---|---|---|---|---|---|---|---|---|---|---|
| 1 | EP300 | p.G1777C | chr22 | 41573044 | G | T | 0.024 | 0.06 | — | NP_001420 |
|  | MLL2 | p.E4152K | chr12 | 49425224 | C | T | 0.88 | 0.953 | — | NP_003473.3 |
|  | FLT3 | p.P439S | chr13 | 28610175 | G | A | 0.31 | 0.385 | — | NP_004110 |
|  | MAP3K1 | p.S1002F | chr5 | 56178032 | C | T | 0.67 | 0.563 | — | NP_005912 |
|  | ATM | p.P1564S | chr11 | 108164118 | C | T | 0.57 | 0.524 | — | NP_000042 |
|  | ALOX12B | p.D492N | chr17 | 7979551 | C | T | 0.5 | 0.5 | — | NP_001130 |
| 2 | ARID1A | p.Q1365K | chr1 | 27100381 | C | A | 0.16 | 0.167 | 0.18 | NP_006006 |
|  | KDM5C | p.A612T | chrX | 53231068 | C | T | 0.4 | 0.386 | 0.47 | NP_004178 |
|  | JAK1 | p.S260G | chr1 | 65332761 | T | C | 0.17 | 0.154 | 0.13 | NP_002218 |
|  | MPL | p.E54V | chr1 | 43803851 | A | T | 0.15 | 0.143 | 0.2 | NP_005364 |
|  | FLT3 | p.Q394* | chr13 | 28622437 | G | A | 0.14 | 0.156 | 0.18 | NP_004110 |
|  | TP53 | p.R248L | chr17 | 7577538 | C | A | 0.086 | 0.086 | — | NP_001119585 |
|  | DNMT3A | p.Y533C | chr2 | 25467478 | T | C | 0.18 | 0.185 | — | NP_783328 |

TABLE 6-continued

Somatic variants identified by at least two platforms

| Sample | Gene | Mutation | Chr | Position | Ref | Alt | IMPACT | Hem | Exome | Refseq_ProtID |
|---|---|---|---|---|---|---|---|---|---|---|
| | GLI1 | p.G162C | chr12 | 57858988 | G | T | 0.11 | not targeted | 0.11 | NP_005260 |
| | CDK8 | p.V169I | chr13 | 26956999 | G | A | 0.23 | not targeted | 0.32 | NP_001251 |
| | FGFR1 | p.G205D | chr8 | 38285446 | C | T | 0.17 | not targeted | 0.14 | NP_075598 |
| | ALK | p.A892T | chr2 | 29451891 | C | T | 0.15 | 0.091 | — | NP_004295 |
| | BCL6 | p.K558M | chr3 | 187444554 | T | A | 0.18 | 0.196 | — | NP_001124317 |
| 3 | EP300 | p.M1972T | chr22 | 41573630 | T | C | 0.29 | 0.287 | 0.24 | NP_001420 |
| | EP300 | p.Q2355L | chr22 | 41574779 | A | T | 0.27 | 0.258 | 0.33 | NP_001420 |
| | EZH2 | p.A483S | chr7 | 148513834 | C | A | 0.18 | 0.259 | 0.46 | NP_004447 |
| | TP53 | p.M169I | chr17 | 7578423 | C | T | 0.029 | 0.024 | — | NP_001119585 |
| | IDH2 | p.W164L | chr15 | 90631862 | C | A | 0.13 | 0.108 | — | NP_002159 |
| | DNMT3A | p.T260N | chr2 | 25470982 | G | T | 0.1 | 0.101 | — | NP_783328 |
| | ATM | p.A1211T | chr11 | 108153491 | G | A | 0.15 | 0.112 | — | NP_000042 |
| 4 | NF1 | p.A1670V | chr17 | 29653011 | C | T | 0.25 | 0.238 | 0.25 | NP_001035957 |
| | SMARCB1 | p.N154K | chr22 | 24143230 | C | G | 0.14 | 0.149 | 0.14 | NP_001007469 |
| | BCOR | p.P1156L | chrX | 39923624 | G | A | 0.49 | 0.451 | 0.46 | NP_001116857 |
| | TET2 | p.Q170\* | chr4 | 106196771 | C | T | 0.06 | 0.054 | — | NP_001120680 |
| | WT1 | p.T278I[†] | chr11 | 32449541 | G | A | 0.11 | 0.112 | — | NP_000369 |
| | EPHA7 | p.G592S[†] | chr6 | 93973602 | C | T | 0.14 | 0.129 | — | NP_004431 |
| | EGFR | p.A871E[†] | chr7 | 55259554 | C | A | 0.037 | 0.042 | — | NP_005219 |
| | PNRC1 | p.R97Q | chr6 | 89790903 | G | A | 0.035 | 0.048 | — | NP_006804 |
| | MLL | p.A2061T | chr11 | 118371733 | G | A | 0.17 | 0.157 | — | NP_005924 |
| | CYLD | p.G173C | chr16 | 50785527 | G | T | 0.14 | 0.157 | — | NP_001035877 |
| | CEBPA | p.A79T | chr19 | 33793086 | C | T | 0.15 | 0.141 | — | NP_001272758 |
| | EPHA10 | p.L80Q | chr1 | 38227688 | A | T | 0.11 | not targeted | 0.13 | NP_001092909 |
| | NF1 | p.K1517M | chr17 | 29588764 | A | T | — | 0.121 | 0.32 | NP_001035957 |
| 5 | IRF4 | p.M146I | chr6 | 395881 | G | C | 0.69 | 0.667 | 0.73 | NP_002451 |
| | ETV6 | p.P25S[†] | chr12 | 11905423 | C | T | 0.031 | 0.038 | — | NP_001978 |
| | ALK | p.R1209Q | chr2 | 29443591 | C | T | 0.21 | 0.221 | — | NP_004295 |
| | MLL2 | p.H4930L | chr12 | 49420150 | T | A | 0.18 | 0.149 | — | NP_003473.3. |
| | JAK3 | p.Q1094* | chr19 | 17937647 | G | A | 0.23 | 0.25 | — | NP_000206 |
| | ASXL1 | p.G792D | chr20 | 31022890 | G | A | 0.18 | 0.164 | — | NP_056153 |
| | KIT | p.G126E | chr4 | 55564489 | G | A | 0.36 | 0.237 | — | NP_000213 |
| | EPHA2 | p.E302G | chr1 | 16464844 | T | C | 0.1 | not targeted | 0.2 | NP_004422 |
| | DUSP27 | p.Q737L | chr1 | 167096578 | A | T | not | 0.102 | 0.12 | NP_001073895 |
| | MEF2B | p.P279S | chr19 | 19257149 | G | A | 0.26 | 0.343 | — | NP_001139257 |
| | ALK | p.L1145V | chr2 | 29445400 | G | C | 0.19 | 0.199 | — | NP_004295 |
| | ERG | p.P299L | chr21 | 39762961 | G | A | 0.13 | 0.151 | — | NP_001230357 |
| | SMO | p.A379V | chr7 | 128846206 | T | C | 0.17 | not targeted | 0.2 | NP_005622 |
| | INSR | p.R162S | chr19 | 7267524 | G | T | 0.6 | not targeted | 0.53 | NP_000199 |
| 6 | NOTCH2 | p.P1101T | chr1 | 120480516 | G | T | 0.18 | 0.174 | 0.26 | NP_077719 |
| | NF1 | p.Q2434H | chr17 | 29676250 | G | T | 0.094 | 0.099 | — | NP_001035957 |
| | SMARCA | p.D694E[†] | chr19 | 11118658 | C | A | 0.076 | 0.087 | — | NP_003063 |
| | MLL | p.K3846M | chr11 | 118392035 | A | T | 0.32 | 0.236 | — | NP_005924 |
| | IDH2 | p.K205R | chr15 | 90631655 | T | C | 0.11 | 0.245 | — | NP_002159 |
| | EP300 | p.R1737H | chr22 | 41572925 | G | A | 0.13 | 0.105 | — | NP_001420 |
| | KIT | p.G93S | chr4 | 55561887 | G | A | 0.12 | 0.129 | — | NP_000213 |
| | BCOR | p.V293I | chrX | 39933722 | C | T | 0.15 | 0.147 | — | NP_001116857 |
| | HNF1A | p.A562V | chr12 | 121437347 | C | T | 0.18 | not targeted | 0.18 | NP_000536 |
| | MEF2B | p.P197R | chr19 | 19257636 | G | C | 0.17 | 0.148 | — | NP_001139257 |
| 12 | BCOR | p.P1613L | chrX | 39913172 | G | A | 0.47 | 0.483 | 0.41 | NP_001116857 |
| | NCOR2 | p.A1706T | chr12 | 124826462 | C | T | not | 0.522 | 0.56 | NP_006303 |
| | BRCA1 | p.S1613G | chr17 | 41223094 | T | C | 1 | not targeted | 0.99 | NP_009231 |
| | PASD1 | p.Q213E | chrX | 150817094 | C | G | not | 0.437 | 0.23 | NP_775764 |
| | DUSP27 | p.T1124N | chr1 | 167097739 | C | A | not | 0.494 | 0.46 | NP_001073895 |
| 13 | TET2 | p.E1874K | chr4 | 106197287 | G | A | 0.17 | 0.138 | 0.15 | NP_001120680 |
| 15 | TP53 | p.R283P | chr17 | 7577090 | C | G | 0.055 | 0.065 | — | NP_001119585 |

Variants highlighted in bold were previously described in COSMIC.
[†]Indicates variants altering a codon previously reported in COSMIC, but result in a different substitution of the same amino acid. Not targeted, specific gene not targeted by respective sequencing platform.
Ref, reference nucleotide; alt, altered nucleotide; chr, chromosome. Data from three sequencing platforms (Hem-Capture panel (Hem), IMPACT, and whole-exome sequencing data) are shown.

6.2. Results:

Exome Sequencing of Infiltrating White Blood Cells

Fresh samples of seventeen untreated primary breast cancers were obtained (Table 1) and fluorescent activated cell sorting was performed to separate CD45-positive leukocytes from CD45-negative epithelial cells (FIG. 2a). Non-triple negative breast cancers showing a prominent lymphocytic infiltrate in core biopsies were also included in this study. Patients with neoadjuvant chemotherapy were not studied to exclude the effects of chemotherapy on mutational burden. Of the 17 patients, 13 had triple negative breast cancer, 2 had ER-positive, HER2-positive disease, and 2 had ER-positive, HER2-negative disease (Table 1). Exome sequencing of these CD45-positive tumor-infiltrating leukocytes was performed to investigate for the presence of mutations. Buccal swab samples of five patients (1, 3, 5, 8, and 14) were also analyzed by whole exome sequencing. Samples with insufficient amount of DNA were whole genome amplified (WGA) prior to further downstream applications. HaplotypeCaller (GATK suite version 2.8-1) was used to identify mutations present in tumor-infiltrating leukocytes that have not been reported in germline samples.

Candidate variants called by GATK and which were not present in the buccal samples that were analyzed through the same pipeline and were not annotated as polymorphisms in SNP databases (see Section 6.1) were annotated as high confidence variants. This approach identified candidate mutations in known cancer genes, including in BCOR, NOTCH2, TET2, NF1, EZH2, and JAK1 (FIG. 2b, Table 4). Of importance, mutations in these genes were previously implicated in the pathogenesis of hematologic malignancies. The data suggest that mutations in known cancer genes are present in the white blood cells infiltrating a subset of breast cancers.

Confirmation of Identified Variants Using Targeted Sequencing Platforms

Although exome sequencing identified putative somatic mutations in known cancer genes in a subset of breast cancers, the limited coverage may limit the ability to identify mutations in infiltrating leukocytes. Therefore, in order to obtain coverage for genes with known roles in malignant transformation and to validate putative mutations identified in exome sequencing, capture-based sequencing of 20 paired tumor infiltrating-leukocyte and matched germline (buccal swab) DNA samples (Table 1) was performed. Two capture-based platforms that interrogate genes implicated in hematopoietic malignancies (Table 3 and Section 6.1) and in epithelial malignancies (Iyer, G., et al., 2012, Science, 338: 221) were used. Somatic variants identified by whole exome sequencing were further filtered against the two targeted sequencing panels to ensure the same variants were identified using higher coverage sequencing. All variants confirmed by three sequencing platforms and/or previously described in COSMIC and which were not identified in germline DNA were scored as somatic independent of allele frequency. Further, variants detected by two sequencing platforms and an allele frequency ≥10% and not identified in paired germline DNA were scored as somatic mutations. Following these criteria, we identified somatic mutations in 9 of the 20 patients (45%; Table 5 and Table 6). PCR and high coverage 454 sequencing on laser-capture dissected breast cancer cells was performed, the specific mutations that were detected was analyzed. Two TP53 mutations were present in purified breast cancer cells, suggesting that these mutations originated from the epithelial, malignant clone, and were censored (Table 7). By contrast, all other mutations were not identified in breast cancer cells consistent with their origin in the leukocyte component. These mutations included somatic mutations in known leukemia genes (DNMT3A TET2, BCOR, and TP53) which were present in tumor-infiltrating leukocytes. A subset of specific mutations was validated using original DNA, including mutations in TET2 (Patient 4: TET2 p.Q1702*) and BCOR (Patient 12: BCOR p.P1613L). The two TET2 mutations were likely pathogenic as a nonsense allele (TET2 p.Q1702*) and a mutation in a highly conserved residue in TET2 commonly mutated in myeloid malignancies (TET2 p.E1874K) were identified. Mutations in the transcriptional co-repressor BCOR, which is targeted by somatic mutations in myeloid leukemia, were identified in three patients. It is important to note that most of these mutations were present in at least 5-20% of reads. This suggests that these mutations were present in enriched subclones and were not rare alleles occurring in a minority of hematopoietic stem cells as previously reported in normal donors. A median of 7 mutations/case were identified in the nine patients with somatic mutations (Table 6). Mutations in tumor-infiltrating white blood cells were identified in all breast cancer subtypes and were present irrespective of the extent of leukocyte infiltrate as assessed by histopathologic assessment (Table 1).

TABLE 7

Deep sequencing of breast tumor cells

| Sample | Gene | Mutation | # variant reads | VAF tumor cells [%] | Coverage depth | VAF tumor infiltrating |
|---|---|---|---|---|---|---|
| 1 | EP300 | p.G1777C | 2 | 0.01 | 19460 | 6.0 |
| 2 | DNMT3A | p.Y533C | 1 | 0.01 | 17707 | 18.5 |
|   | TP53 | p.R248L | 6547 | 71.34 | 9177 | 8.6 |
| 3 | EZH2 | p.A483S | 0 | 0.00 | 14518 | 46.0 |
|   | IDH2 | p.W164L | 8 | 0.00 | 20529 | 13.0 |
|   | DNMT3A | p.T260N | 0 | 0.00 | 20135 | 10.1 |
|   | TP53 | p.M169I | 0 | 0.04 | 21792 | 2.9 |
| 4 | BCOR | p.P1156L | 4 | 0.05 | 8521 | 49.0 |
|   | EPHA7 | p.G592S | 1 | 0.01 | 9060 | 14.0 |
|   | WT1 | p.T278I | —* | —* | N/A | 11.0 |
|   | TET2 | p.Q1702* | 54 | 0.26 | 20909 | 6.0 |
|   | PNRC1 | p.R97Q | 9 | 0.16 | 5526 | 4.8 |
|   | EGFR | p.A871E | 0 | 0.00 | 5844 | 4.2 |
| 5 | ALK | p.R1209Q | 14 | 0.15 | 9426 | 21.0 |
|   | ETV6 | p.P25S | 0 | 0.00 | 3136 | 3.8 |
| 6 | IDH2 | p.K205R | 0 | 0.00 | 4758 | 24.5 |
|   | NOTCH2 | p.P1101T | —* | —* | —* | 18.0 |
|   | NF1 | p.Q2434H | 2 | 0.04 | 5361 | 9.9 |
|   | SMARCA4 | p.D694E | —* | —* | N/A | 8.7 |
| 12 | BCOR | p.P1613L | —+ | —+ | N/A | 48.3 |
| 13 | TET2 | p.E1874K | 356 | 2.03 | 17567 | 17.0 |
| 15 | TP53 | p.R283P | 21327 | 88.48 | 24104 | 6.5 |

VAF, variant allele frequency;
+no tumor sample obtainable;
*not sequenced; N/A, not applicable.

Sequencing Analysis of Circulating Leukocytes

Sequencing of circulating leukocytes from these patients was next performed. Peripheral blood samples were prospectively obtained in a HIPAA-compliant and IRB-approved manner from 8 of the 10 patients in which somatic mutations had been identified in their tumor-infiltrating leukocytes. Two mutations (Patient 2: DNMT3A p.Y533C, Patient 12: BCOR p.P1613L) were detectable in circulating leukocytes (both mononuclear cells and granulocytes). The remaining 19 mutations were not detectable by sequencing in circulating leukocytes due to the limits of the sequencing coverage. Of note, the mutation in DNMT3A was present at 25-fold reduced variant allele frequency compared to tumor-infiltrating leukocytes (Table 8). It cannot be excluded that these other mutations were present in circulating cells at low allele burden, or alternatively or additionally, in stem/progenitor cells in the bone marrow from these patients. However, these data demonstrate that somatic mutations are highly enriched in tumor infiltrating leukocytes compared to the overall hematopoietic compartment.

TABLE 8

Deep sequencing of peripheral blood cells from breast cancer patients

| Sample | Gene | Mutation | # variant reads | VAF MNC [%] | Coverage depth | # variant reads | VAF Granulocytes [%] | Coverage depth | VAF tumor infiltrating leukocytes [%] |
|---|---|---|---|---|---|---|---|---|---|
| 1 | EP300 | p.G1777C | 3 | 0.01 | 44363 | 3 | 0.01 | 45130 | 6.0 |
| 2 | DNMT3A | p.Y533C | 363 | 0.73 | 50062 | 669 | 1.34 | 50046 | 18.5 |
|   | TP53 | p.R248L | 0 | 0.00 | 50013 | 3 | 0.01 | 50003 | 8.6 |
| 3 | EZH2 | p.A483S | 0 | 0.00 | 30057 | 0 | 0.00 | 23722 | 46.0 |
|   | IDH2 | p.W164L | 0 | 0.00 | 33870 | 0 | 0.00 | 30853 | 13.0 |
|   | DNMT3A | p.T260N | 0 | 0.00 | 38347 | 0 | 0.00 | 27035 | 10.1 |
|   | TP53 | p.M169I | 7 | 0.02 | 41638 | 4 | 0.01 | 38776 | 2.9 |
| 4 | BCOR | p.P1156L | 19 | 0.04 | 50003 | 10 | 0.02 | 49992 | 49.0 |
|   | EPHA7 | p.G592S | 10 | 0.02 | 50063 | 7 | 0.01 | 50045 | 14.0 |
|   | WT1 | p.T278I | 13 | 0.03 | 47802 | 14 | 0.03 | 41982 | 11.0 |
|   | TET2 | p.Q1702* | 20 | 0.04 | 49539 | 29 | 0.07 | 41051 | 6.0 |
|   | PNRC1 | p.R97Q | 20 | 0.04 | 50054 | 34 | 0.07 | 45952 | 4.8 |
|   | EGFR | p.A871E | 0 | 0.00 | 50069 | 1 | 0.00 | 50076 | 4.2 |
| 5 | ALK | p.R1209Q | 18 | 0.04 | 49999 | 20 | 0.04 | 49991 | 21.0 |
|   | ETV6 | p.P25S | 18 | 0.06 | 29627 | 33 | 0.08 | 42677 | 3.8 |
| 6 | IDH2 | p.K205R | 50 | 0.10 | 50021 | 51 | 0.10 | 50050 | 24.5 |
|   | NOTCH2* | p.P1101T | — | — | — | — | — | — | 18.0 |
|   | NF1 | p.Q2434H | 0 | 0.00 | 50039 | 0 | 0.00 | 50040 | 9.9 |
|   | SMARCA4 | p.D694E | 1 | 0.00 | 50057 | 0 | 0.00 | 50051 | 8.7 |
| 12 | BCOR | p.P1613L | 21665 | 43.36 | 49967 | 20650 | 41.31 | 49983 | 48.3 |
| 13 | TET2* | p.E1874K | — | — | N/A | — | — | N/A | 17.0 |
| 15 | TP53 | p.R283P | 160 | 0.36 | 44534 | 132 | 0.31 | 42507 | 6.5 |

PB, peripheral blood;
MNC, mononuclear cells, depth, number of total reads;
N/A, not applicable.
*not sequenced.

In this study, high throughput, next generation sequencing data were used to demonstrate that leukocytes with somatic mutations in known cancer genes infiltrate many primary cancers. Somatic mutations were identified and validated in ten of twenty patients, including in known leukemia genes (DNTM3A, TET2, and BCOR). In two cases, two mutations observed in the tumor-infiltrating leukocytes were also detected in the circulating leukocytes of the same patients but at a significantly lower frequency.

The data demonstrate that some nonhematopoietic cancers are characterized by infiltrating leukocytes with somatic mutations in known cancer genes.

7. INCORPORATION BY REFERENCE

Various publications are cited herein, the disclosures of which are hereby incorporated by reference herein in their entireties.

---

What is claimed is:

1. A method of treating mutant tumor-infiltrating leukocytes comprising:
   determining that a patient having a nonhematopoietic malignant tumor comprising a breast tumor has one or more somatic gene mutations present in tumor-infiltrating leukocytes of the breast tumor, wherein the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, EPHA7, MEL, CYLD, CEBPA, JAK3, ASXL1, KIT, MEF2B, and ERG; are in a coding region, and result in an amino acid substitution or a premature stop codon; and are not identified in neoplastic cells of the breast tumor itself; and
   administering to the patient determined to have the one or more somatic gene mutations present in the tumor-infiltrating leukocytes of the breast tumor an agent that preferentially kills or inhibits proliferation or activity of leukocytes relative to nonhematopoietic cells, wherein the agent is known or indicated to treat leukemia and comprises a leukocyte-specific antibody.

2. The method of claim 1, wherein the one or more somatic gene mutations are present in one or more genes selected from the group consisting of BCOR, NOTCH2, TET2, NF1, EZH2, JAK1, DNMT3A, and TP53.

3. The method of claim 1, wherein the one or more somatic gene mutations are present in TET2, DNMT3A, or ASXL1.

4. The method of claim 1, wherein the determining comprises comparing the DNA sequence of the tumor-infiltrating leukocytes with the DNA sequence of non-cancerous cells.

5. The method of claim 1, wherein the determining further comprises generating a report that indicates the presence of one or more somatic gene mutations in the tumor-infiltrating leukocytes.

6. The method of claim 1, wherein the determining further comprises communicating the presence of one or more somatic gene mutations in the tumor-infiltrating leukocytes.

7. The method of claim 1, wherein the determining further comprises communicating (i) the presence of one or more somatic gene mutations in the tumor-infiltrating leukocytes, and (ii) that the first agent is a selected or indicated therapy for the patient.

8. The method of claim 1, wherein the determining further comprises obtaining a sample of tissue from the breast tumor; and isolating the tumor-infiltrating leukocytes from the tissue of the breast tumor.

9. The method of claim 8, wherein the determining further comprises extracting DNA from the tumor-infiltrating leukocytes.

10. The method of claim 9, wherein the determining further comprises sequencing the DNA of the tumor-infiltrating leukocytes.

11. The method of claim 1, wherein the tumor-infiltrating leukocytes are neutrophils, eosinophils, basophils, monocytes, macrophages, and/or lymphocytes.

12. The method of claim 1, wherein the leukocyte-specific antibody is an anti-CD45 antibody.

13. The method of claim 1, wherein the leukocyte-specific antibody is an anti-CD33 antibody.

14. The method of claim 1, wherein the leukocyte-specific antibody is an anti-CD20 antibody.

15. The method of claim 14, wherein the anti-CD20 antibody is rituximab.

16. The method of claim 1, wherein the leukocyte-specific antibody is conjugated to a cytotoxic drug.

17. The method of claim 1, wherein the leukocyte-specific antibody is an anti-CD33 antibody conjugated to calicheamicin.

18. The method of claim 17, wherein the anti-CD33 antibody conjugated to calicheamicin is gemtuzumab ozogamicin.

19. The method of claim 1, wherein the patient is a human patient.

20. The method of claim 1, wherein the patient has not had neoadjuvant chemotherapy.

21. The method of claim 1, wherein the tumor-infiltrating leukocytes are CD45+ cells.

22. The method of claim 1, wherein the one or more somatic gene mutations are selected from the group consisting of ALK p.A892T, ALK p.H1030P, ALK p.L1145V, ALK p.R1209Q, ALOX12B p.D492N, ARIMA p.Q1365K, ASXL1 p.G792D, ATM p.A1211T, ATM p.P1564S, ATM p.R2105S, ATP10A p.P35A, BCL6 p.K558M, BCOR p.P1156L, BCOR p.P1613L, BCOR p.P1648L, BCOR p.V293I, BRCA1 p.S1613G, CDK8 p.V169I, CEBPA p.A79T, CSF1R p.R216Q, CYLD p.G173C, DNMT3A p.T260N, DNMT3A p.Y533C, DUSP27 p.Q737L, DUSP27 p.T1124N, EGFR p.A871E, EP300 p.G1777C, EP300 p.M1972T, EP300 p.Q2355L, EP300 p.R1737H, EPHA2 p.E302G, EPHA7 p.G592S, EPHA10 p.L80Q, ERG p.P299L, ETV6 p.P25S, EZH2 p.A478S, EZH2 p.A483S, FGFR1 p.G205D, FGFR1 p.M731V, FGFR4 p.S776F, FLT1 p.V1331I, FLT3 p.P439S, FLT3 p.Q394*, FREM2 p.G1608D, GATA2 p.A286P, GLI1 p.G162C, HLA-A p.A270S, HLA-A p.E176V, HLA-B p.R155S, HNF1A p.A562V, IDH2 p.K205R, IDH2 p.W164L, INPP4B p.K816E, INSR p.R162S, IRF4 p.A370V, IRF4 p.M146I, ITK p.D510N, JAK1 p.S260G, JAK3 p.Q1094*, KDM5C p.A612T, KIT p.G126E, KIT p.G93S, MAP3K1 p.S1002F, MEF2B p.P197R, MEF2B p.P279S, MET p.Q165K, MLL p.A2061T, MLL p.K3846M, MLL2 p.E4152K, MLL2 p.H4930L, MLL4 p.S214P, MPL p.E54V, MUC4 p.A2025V, MYO18A p.A958V, NCOR2 p.A1706T, NEB p.Y1092C, NF1 p.A1670V, NF1 p.K1517M, NF1 p.N2775S, NF1 p.Q2434H, NOTCH2 p.A21T, NOTCH2 p.P1101T, NOTCH2 p.S1708P, PASD1 p.Q213E, PIGN p.T569N, PNRC1 p.R97Q, POU2F2 p.L459F, PTCH1 p.I685M, RPTOR p.V476M, SMARCA4 p.D694E, SMARCB1 p.N154K, SMO p.A379V, SOX17 p.G178R, TET2 p.E1874K, TET2 p.Q1702*, TNFSF9 p.A58S, TP53 p.M169I, TRRAP p.S1073G, TTC28 p.K2346Q, and WT1 p.T278I.

* * * * *

SEQUENCE LISTING

```
<160> NUMBER OF SEQ ID NOS: 2

<210> SEQ ID NO 1
<211> LENGTH: 135142
<212> TYPE: DNA
<213> ORGANISM: Homo sapiens

<400> SEQUENCE: 1
aaattagggc ttcgctttta aaaaaaatta cagaccaaaa aaagtgtggt tacacaatat         60
aactagtatt gacttaaggg tactgtgatc accatgcagt gatcccataa aagatgtgac        120
caaaataccc acttaaaatt tgaacgtcag tcatgtaaga acatgtaaaa gatgaaggga        180
atatttcaaa aacgactatc tgacgtaata tgatacttac tatgactcat atgggctttg        240
ttcttcatct catcttcaaa taaaaagttg atgattagaa aaaggagcat tagaaggggg        300
aagtaacact actcggcaat agagaaaaac tccggtcaaa ggaagagcat agttacagag        360
ctccgaatgt cagggaaaat caagcatccg tcattcggaa ttagctctgt atcggtcggt        420
ttcttcatta cttaattgta cggggggaaa ctacttcaaa gtaagggctc ttacgagagg        480
caacttaagc atttgaaagt gcaggtttat ttcctcctag cgagaagtag ggggtcacta        540
```

```
gtgagaaacc tatttcaatc tgtgagacgc ccccttctac tcagcccacg tggctaaagt    600
aaacagaagg tgggccgggg cggggagaaa cagaactcgg tcaatttccc agtttgtcgg    660
gtctttaaaa atacaggccc ctaaagcact aagggcatgc cctcggtgaa acaggggagc    720
gcttctgctg aatgagatta aagcgacaga aagggaaag gagagcgcgg gcaacgggat     780
ctaaagggag atagagacgc gggcctctga gggtaaggtg ggcgcaagcg gaggtgtggt    840
gcggggagag gtgccagtgg gtggaggcgg gggccagagc gagggcacgt gcgggtacac    900
tccggaggag gtgggtgcgc gcggggggcgt gtgcgcggga cctcgaagtg gtggtggagt   960
gcagaccagc aaaaagtttc aagggaaat cttagatgtc acgtctttgt ccaggcaccc    1020
gtgccatccc aacctcccac ctcgccccca accttcgcgc ttgctctgct tcttctccca   1080
ggggtggaga cccgccgagg tcccgggggt tcccgagggc tgcacccttc cccgcgctcg   1140
ccagccctgg cccctactcc gcgctggtcc gggcgcacca ctcccccgc gccactgcac    1200 ggcgtgaggg cagcccaggt ctccactgcg cgccccgctg tacggcccca ggtgccgccg   1260
gcctttgtgc tggacgcccg gtgcgggggg ctaattccct gggagccggg gctgagggcc   1320
ccagggcggc ggcgcaggcc ggggcggagc gggaggaggc cggggcggag caggaggagg   1380
cccgggcgga ggaggagagc cggccggtagc ggcagtggca gcggcgagag cttgggcggc   1440
cgccgccgcc tcctcgcgag cgccgcgcgc ccgggtcccg ctcgcatgca agtcacgtcc    1500
gccccctcgg cgcggccgcc ccgagacgcc ggccccgctg agtgatgaga acagacgtca   1560
aactgcctta tgaatattga tgcggaggct aggctgcttt cgtagagaag cagaaggaag   1620
caagatggct gcccttttagg atttgttaga aaggagaccc gactgcaact gctggattgc   1680
tgcaaggctg agggacgaga acgaggtcag agcgcttctc ttatgccgcg aaactctccc   1740
tttcttctcc ccttcgctttt ttctcggct tccaggggact ggggagcaaa ccctgtagtg   1800
tcacccacaa ataccaagag ggaagaggga agcttcacaa attactggag cctcttcaac   1860
atggctgaca aatatagttt taattccctc tacccctttt aaacctgtag ttctgtgttc   1920
tcttctctcc tcctaatgct cgtcccctca tctcccagaa aacttacctt tgtgcctccg   1980
acgagccggt ttcccggcct ttttaatcc tcagaaaagt gattttaaaa tttgctttcc    2040
tttctaaaat agttcagctt tggggcact actttttccct ttaatcctct tccctgtttt    2100
ctttcgtgta agtgaaacga gtctcccgtt tatcctgaac aacctcagag agaacactga   2160
tagggtgttt ttcgacccctt ttatcagctg tagggtctgg gtctgggttt gtgtctgcct   2220
cctcctacct tcttatcccc ctttaggggg ctgtacgaag tgaatgtcac agggagtgga   2280
attggagtac actgagtggg ttttttttttt ccttaagtcc gcgcgttttg ttagcggcgc   2340
tgagtgaaag aggaaagaat agtttctctg gttccccaaa caagaccaga actcactttt   2400
ctcaaggtac ataagtcagc gctgggctga gccttccagc ctggggaatg tatgtaagag   2460
aatttatgga caaatctgtg tcccggcttt gtgcttctcc cgaatcagct tcgtttggtt   2520
ccttggtaag tgacaggcag acacaaaggc aggcgcaggc ccggggaggg ggcgggaggg   2580
ggtggggagc gcagcgttgg agttgcaaga ctgcaaggtc aggggcgcct aaagaaatga   2640
aacccaatcc cagcaaagaa gtgaagagca gatttataac agtcccatcc aaatttctct   2700
ttggcttctc tctttggtct ttcatctctc tgcctttctc tctgtgtctc ctctctactc   2760 ttctcttctct ctctctcata cacatacaca cacacacaca cacacacacc tcactcgcat   2820
cttgctgaat cttttcactg ggactgcttg tctagttttta ttaagctaat agggtttgta    2880
tggagagttt tctacctatg acataatgaa gtgtggcctg gatagactcc tggaaaggcc   2940
```

```
gaaaatgaaa tataagtgtt atttgctggt tattccctc atgatatact tttaattaca    3000
ttgagggagt tctcccttct tcatctaatg tttaagaatt gagaaaaggc ttattttcca    3060
gcggtaaaat ttagtgcata aaatttagtg aaatatttat atatttacgt gtctagggag    3120
tggaatacat tcatgaattt aatatctcaa atcacacatt gtgcttttc cccttcagtc    3180
agggattata atgggaaacc caaattcaaa gatattcatc aacaaatgat ccatcatagg    3240
aataagattg tatcttaagg gaagttggga ttcacagaga aaagacattg gtttggtttg    3300
gtgtgatact gtgggtattg ttgcctggct aatgaaatca ttacatttgc attttaatgg    3360
aaagttgaaa tactaagggg agttatgttc ttttacatgt ttgtatgtgt gcttaataat    3420
gtttggaata gaatataaat ttaaacacaa taaatattga ttttttttaaa tgttaataag    3480
cagagaacgg ttaatgaagt gttggataat caaactgaag tttagaagac aatttatagg    3540
attaaaaaat ggatagaagg aaaaacacaa taatagatat ttctccataa gtcgaatttc    3600
caaaactatt tgtcctcgat agttcacttt gtaactttct attttgatct ttgttaattt    3660
aatgtagttt gctttaatca ttgatacgtg gggttctttc acatgattac aagggagaag    3720
cattactcat ctctgtggaa tagaaacggt tcattggtta gttcttattt gccctaaaat    3780
taaaacaaaa attaggattt taccattaat gctgttcatg gtaaactatc gagaaaacta    3840
tggttaatta ttccagcaat tcagaattaa aaacaattcc ttttgctaac aaactaatat    3900
ttactttttg gggacaactt ttcaaatgtt gtggtatata ctgtcttcag gctactcaac    3960
taataataga tacaacattt tccactcaat aaataagaat aactcacattg gttaataatt    4020
ttgaatacaa ctatgaaggc ttgttttttc ctgtcatcaa atttagattc ttgttatttt    4080
gtgcatccta cttttatact gaaaatagct gctaattaat actgtataaa gtatttcagt    4140
gattataagg aagagatgtg tatgttagtc actttatcct ttgttggaaa agagaaatta    4200
ttttaataag tatggggtag tttacaataa aagacataac ctcagttctt tctttaccat    4260
atatgtgatc atactaccta ggtgctccaa aaattccata ggactgtctt gggttattga    4320
attttaggaa catgataatg gacaataaca agatagatag cttttcttaa ctatgacatt    4380
gttttgctta ttttcttatt gaactaatca tcaatgagaa attaagttgc agtgagagaa    4440
atcccttgct ttgtttaaat tgtcatattt gccaaactct tcttaaggct ttaattaggt    4500
ctgatgtgcc agtttatgcc agaagccgga ggaattgata tgattttgag gcagtggcac    4560
atggtcctac tagacattgg caagtgaata tcacttccag aacaagtgaa gtgcacctgc    4620
caaggagttg ttatgaaaga attccaaagt cottattggg cactggtctt gtattaggta    4680
acaacaactg gagttaatgt tttagtttca cttgttgaag ttaaaagttc cctatcaatt    4740
cttctaagac tccaccccca aacaatgttg taagtcaaat gtcactattg aaatgtattt    4800
ccttaattac tgacctcatt aagaagccct tcttatgatt cataggcaca cctcacagaa    4860
actctatttt ccatcctgcc caaagtctga gtaggtaaat tcttatgaat tcttatgaaa    4920
ttaccttgaa ataaaatatc ttcaaaagtt acggatgcta gacattgtat aatgtcaata    4980
ttttagaata tctaatattt agaaaatctt agatctactt tttatgcttt aattgcttct    5040
aatgcaagtt aaattgtttt tgttgttatt gttttaatag aatttcatag tcttatctag    5100
caatttcaaa tcgctggaaa gagtcatctt tgttatataa ataaccatgt agactgtttt    5160
aatgttattg tttcctacct tgggaacagg ctaaaacttt ggaccagctg tcagtatttg    5220
ttcatcagaa taacactttg tcaatgatta ttctaccatt gcacagtagt tcttaaggat    5280
```

```
agtaatggta ccaaagccag cagcaataga atatctccca agccaacttt acaattggag    5340
ccttcactgt gggaaagacc agttgccaag tagagctggt ggttatctgg gaaactgtgc    5400
tgaagaacac aaccacaaat gattttgcca aatatacagt atttacttgg tctagatctc    5460
caatttctat ttctactcac tgccaaaact gagtgaatac tgtgacatta ttgaaggagg    5520
ttatgcagta catctgttgg tttggtatat agtaggagag aagggttcca ggagggaaag    5580
gggaaagtca gagcatgtga atcactgtga ctacaatcca aaaagaatta tgtatgtctg    5640
ctatttccag cattattttt gtcctatatt gtacattgca gagacttgct gacttaaaat    5700
agatatataa tcttttttctc aaaagaatag atatttggtt gtccattcca ataacaaat    5760 tttggatggg cgtggtgact catgcctgta atcctagcac tttgggaggc caaggtgaga    5820
gatcacttga ggccaggagt ttgaaaccac cctgggcaac acagtcaggc ccagtctct    5880 acaaaaaatt taaaaagtta gtggggcatg gtggtacatt cctgtagtcc cagctactca    5940
ggagactgag ataggaggat ggattgagct caagtgttct aacttatagt gagctctgat    6000
cacaccactg cgctccagcc caggcaagag ggagagaccc tatctcaaac agcgacaaca    6060
acaaaaccaa acaaacaaaa aagcacattc tatcagcttt gatttatgtt ttcttcattt    6120
gtaatgacat gtagttaaat gtgtcatact tcaaaaagaa gaaacagata gtaggtggat    6180
tttcaatata atatatatta gatatagata atatatatt tcaatatata atatatgtaa    6240
aaataaattc agtgataata tcatcctacc tgcagtttta agaattcaga actcaggcca    6300
ggtgtggtgg ctcattctgg gaggggaagg caggaggatc acttgaggcc agaagttcta    6360
gaccagcctg gcaacatag tgagatacct gtctctattc aataaaaata aaaataaaaa    6420
taattcagaa ctcaatgctt tatactcact gaaagttgtt cctctaaact gacttgaaat    6480
catgttccaa ataaactgag aattaaagta agagacgagg ccggttgtgg tggctcatgc    6540
ctgtaatccc agcactttgg gacgacaagg caggtggatg acctgaggtc aggagtttga    6600
gaccagcctg gccaacatgg tgaaaccctg tctctactaa aaatacaaaa attagccggg    6660
catggtggca cacaccagta atcccagcta ctcaggaggc tgaggccga gaatcacttg    6720 agcctgggca tggtggctca tacctataat cccagcactt tggaggccg aggcaggtgg    6780 atcacctgac gtcaggaatt cgagaccagt ctggccaaca tggtgaaacc ccatctccac    6840
taaacataca aaattagctg ggtgtggtgg cacatgcctg tagtctcagc tattctggag    6900
gctgatacag gagaattgct tgaaccctcc cgggaggcag aggctgcggt gagccgagat    6960
ggctctgctg cactccagcc tgggcgaggc agagagactc tgcctcaaaa aaagaaaat    7020 aataataata aataggagat gaataaattg gataaagtg tttttgaagg acagtctagg    7080
atataaaatg aactggttgt ttgactaaaa atactacaaa tgtttctttc aaattacatt    7140 tctttttgt ctattggaag gtaggcactg atttctatgt ctttctattc cctaatagaa    7200
cctactgttg acctctcagt caatatttaa tggatgatat agaactagtg aaaaaccatg    7260
caatttaact agaaaaaaaa agtataatct attttctttt ccttttcctt tctttctttc    7320 tttcttttttt ttttttttt tgagacggta tcttgctctg tcacctaggc tggagtgcag    7380
tggtgtgatc tcggctcact gcaacctctg ccttccaggt tcaagtgatt ctcttttctca    7440 gcccccagag tagctgggac taggagcgtg ccccaccaca cctggctaat tttctatttt   7500
ttattagaga cagggtttca ccatgttggc caggctgatc tcgtactcct ggtctcaggt   7560
gatctgcctg cccgggtctc ccaaagtgct gggattacag gcatgagcca ctgcacctgg   7620
tctaatctat tttcaatgta taagagaaaa atagtgttaa gtgtcttggt gatggtgatg   7680
```

```
atggtaggag taatggtgtg ttttccttac atttaatttc tacaggctat ggcaattgcc    7740
ctataaaagc cacccatttt aagcacaaaa gtgaatggtt tttagtaaac ttatatggga    7800
tcatatattt ttaattgaaa tattttttga gttaattata gattcatatg ccattgtatg    7860
aaataataca gagagattcc acgtatactt gctcaatttc ccccagtggc aacactttgc    7920
aaaactataa tatcatatca catcacatgc aaaactataa tatcatatca caaccatgat    7980
actgacattg atgtggccta ctaatcttat tcagatgtcc tcagtttaac ttgtactcat    8040
ttgtgtgtgt tttgttttat accatttagt cacatgatca catattttta aacctttttt    8100
tctcaaaaca gagaagttta gcacaaaagt ttagcaattt atcaatcttg tgattgtgct    8160
gttatgccat attaaaatgt gtgtcagaat gtaagttttt gttttcttaa aagtccttt     8220
tttgatagaa tggcctttat gttaaaaata ttttaagttg ttttgtgaca gtgtaagtcg    8280
atgtcattta attctcatca caaccctaga gataggtatt attcttatcc ctatttatga    8340
gtgaggaaac tgaagcccag tgaggttaaa taacttcctt aagttcatac agcctataca    8400
tggcttaggc ttagccagca tttgagttaa gcagtctgtc tctagtgcca aatctttaa     8460
tcactatatt atacttcatc attatcattg atagctgtaa aagtgtataa tgtggactat    8520
gtagagaaag tcataaaagg agatttaaaa tgcatacagt tgttcacatg aaaacttgta    8580
gccaaatgtt cattacagca ttattaataa tggtaaaaaa tggaaacaac ccagatgtct    8640
atcatgtcat gagtgaataa acaaattgtg gtatatccat acagtgaaat attattaagt    8700
agtataaagg aatggattat tgataaatgc tgtcacatag gtgaatctga gaggcacaag    8760
aaaggccaca tatgatatgc tttcaatttt aagtaacgtc cagaataggc aaatctaagg    8820
agacagaaag ttggctagtt attactaggg gctagggatg ggagggaggt gactcctaat    8880
aagtatgaga tttctttttgg tgatgatgaa aatgttctat aattagatag taatgattgc    8940
ccaactcttt gaatatgctg aaacccactg aattatatgc tttaaaagga tgaatttatt    9000
gtatgtgaat tatatttcaa aaagctgttg ttataaaaat gaatgtagtt gagttatttg    9060
gtttatttta tgtcagaaaa tgtcttacat ctcatgcaaa agaaatgcag gaactatttg    9120
gattgaatga ggctaagcat atcttttctag gaagatggca tcaaggagtt ttattatgcc    9180
tgtaatcctg gcactttggg aggccaaggc gggagaccag aagtttgaga ttagtctggg    9240
caacatcctc ttatagatga gaaggatact taatcactca aaagttggca ttgtgttttg    9300
tgataacaat agcctttaga gctcatatgg gaagattcaa tagatagtga taggttatat    9360
gacttggtaa agagggctta atgtataggt gcaagaaact ttctcagatg tctttagtta    9420
cctagccatt cagttcagga gatgtaaccc aagtgttaaa aggaatgtga ctgggtgcgg    9480
tggctcacac ctgtaatccc agcactttgc gaggcggaag tgggtgggtc tcttgagctc    9540
aggagttgga gacaagcctg gcaacatgg caaaccccca tccctacaaa aaatgcacaa     9600
attagctggg tgtggtggca catccctgta gttccaggta cttgtgggc tgaggcggga     9660
ggatggctcg agcctgggaa gttgaggctg cagtgagcca tgttggtgcc cccacacttc    9720
agcctgggtg acaaaatgag accctctctc tcaaaaaaaa actataaaaa ttgctgttct    9780
tgtttaaatt actacaaagt gcagtttaat ctagaaataa taacaaatta ctagatttgg    9840
ggggttatta atgtcttatc tatgtgaaaa cagaagggca atgcagggca gagaataaac    9900
ttcaaaactt tgagtttgtt aactgtttat atctccactt gtcatgtttc agattttaaa    9960
gttaaaatga caaagtatct catagggttt aaacaagtga ctctttttcct gttaactgat   10020
```

```
actgtggcat gttgaagatg taaaataagg ttgaaaagga aattgctttg cagcagtctt    10080
cataatgcca ggacaaagtg agaaacaggg tcagaatgat gatggctctc catctttgct    10140
acacatggct gcaagtattt acaaatacca gcagaacttc tacaaaccac ttacaggtaa    10200
aatgagtgca gatttttaac actagtccct atggaactat gacttgtagt tttggacaca    10260
cagggtgaat tacttggggt tgattgtatt tgaatttcta accttatgta attctagata    10320
ccagacattc ttgttgtgca atgcttctct ccctttttat tctcatgaga atgctgggtt    10380
gcagccggtt ggatcccata ccttgggacc atgactgata actggagtgg agaaaattca    10440
ctgatctgga aaggttgagc tttagggttc agagacttat ttaaggtaca catgtgattg    10500
tacccaataa ggaagtatat tggctttata taattgttat gatcacttgt tcaatgagta    10560
actatagaat tttactttt aagagtatga tcatagcatc tacttgtagg tttgttgagt    10620
atgtttgaca agcccaagat agatgctcat gttagaccca ttaagaagtt ggtgtagtga    10680
tggttatgga aagcagtaag atagaattta ggttctgttc tccttactgg agaaatgact    10740
agcttacttg tcttcactct ctcttgtttc tctcaaaact ttgtgaacca cctcagctga    10800
ctataaattt ttgtactagt atctccaataa ttttaaaaaa gttgttcaca agtttgagtg    10860
tagtacttca tctttgcttt ttaatgcact tccaaaaaat gtaaatctgt tctcgcatat    10920
taggaacatt ttgatttgtt gtttatttt agctttgctt tttataagta atttatacag    10980
aaggtacacc atattcaaaa gaagaaaaat gggctgtgaa ttttgctga tgtactactc    11040 tcttcaaagg gaattgccta tgttcaggca tagaaatgca ggcagtctga catttaggta    11100
tgccatacag agtattgata ttttaattt gctactttta acattttgag atttgtcaca    11160
gtttgttctg tgggtgggta aaagtaatgg taattttaat tacagttgtc gtgcctcatt    11220
agccattgct aaaacctgcc ttaccaaatc acttattttc ttgatgcagt gttaaatcta    11280
gcttctatgt ccaggttata cattaatgag aacattcacc catctctcaa atgggttatt    11340
atagtatttt ctcctgaaat agatgatgca taaaaaaaag taaaaaagct tcaatagggga    11400 taatgaaagc cagataacat agcatggtat atgagttatt cctcccgttt ttcttacctg    11460
tctgcactaa gaagggcacc cattaaatac cataattatt agttgtgctg cctctgaagt    11520
agagcaccag aatgtgagag taatacaatg agaccacacc cagattctat ccataacata    11580
ctgtcctggt cttattaatt tttttaacct gtttgttctt ttagcacttt tcctgctttt    11640
gtttgaagtc tcttgctttg aagttataga attttttatat ttgccattgg ctgtaaagtt    11700
atctcagctc ttttataact tttcattata tttgcattaa aaggatcact ttgagcaccc    11760
tgtaattaat tcagatgatt attagctttt ttgtttgttc tactgtgcac tctcctatat    11820
acattataac agaagaaaaa accatttcta caaatacagt gtctgatagt tcatcaaatc    11880
agaatgagca tcttaaaaag tgaattatta aaatattaat tcatttacat tcctattta    11940 atgtaccaaa tgtaactgat gaaagaaga ataccataaa tgggtacctt tcaaaaatga    12000
aggaaaaaaa aatctcacaa ctaaagattc ttaccatata aattatttat tttagtaaat    12060
aattatttta gtacaaacag atacatttta gcaggaaaaa acacactttt aaccttgttt    12120
tatagatttt atctttcttc caatctagcc actgaaatgg ttttttctcc agtgaagtta    12180
tattatctac ataagttgaa tttaaaacaa ggttgtattt taattttgca gttgtctgcc    12240
acattacgct tgtggaaaaa cactggcaga aagcaaagct aatagacatt ttgctgttgg    12300 ctcacccttat taatggctaa gatttaatta tgtatttcta ctgaaaagca aacttgaaaa    12360
agacgtttgg ttactaactg tgggaactaa aaattttat ttatttttat tttttatttt    12420
```

```
ttggtagagt ctcactctct tgcccaggct ggagtgcagt ggcatgatct tggctcactg    12480
cagcctcctc cttctgggtt caagcgattc tcctgtctca gcctcccgag tagctgggat    12540
tataggcacc agccaccatg cctggctaat ttttgcattt ttagtagaaa cagcgtttcg    12600
ccatgtaggc taggctggtc tcgaactcct gacctctagt gatccacccc cttctgcttc    12660
ctaaagtgct gggattacag gcatgagcca tcggcctggc caacttattt actgttacaa    12720
cttacttact ttgaaacaac ttatttactg ttaaaaaatg tggttcttat ttcaaataag    12780
attttatgga catcaactaa ttttttaaac atatattgta attttaaaac attttttacca   12840 acattttttca agagcatggg aaatctaggg tatggcattt taaagtgact ttaaagacac   12900
ttcttgggtt ttgttgaagt cagaatattt ttaaaaatac aatgagttta atttactact   12960
gacagatttt cttaattttt ttttgcattg ttataattag tcatgcctta atcctcgggg   13020 ttttttgggaa actatattta ggggttaaaa acttagttat tgacattgta attttttctca  13080 gtattggtaa gaattcaggt gtttaaggaa tggagtttac ttgttttctg ttcacaaacc    13140
cattgtaaaa gatataatga atgtagatga aggtgaaatc cgagatagga agagaggtaa    13200
aatgctactt ttttttcctt cacccaagga aagccattga atactgaatg ggtcatgttg    13260
taatttaatt gggtgtaaat tataactttg taaatcattt gcctacttag tgtatatctc    13320
tggtttttat gtaattcatc tcccataata tctcagttta cactgaagta aataagcaag    13380
caggaataag tcctgcaaat agaggaagta gaaagtgcat tcagaatgca ttgctgaaat    13440
tgtaaaactg atcctaaatt gaattaggta gagcagttaa tttagattac aagaaatgca    13500
acaggaaaaa aatattacag ttcttcctct tttttggaaa aaaaaaaaga aagaaaagac    13560 aaataaaatca cccttagtta gtgataaattc cttgacatct gtatgctcat ttttagggcc   13620
aaaaaatagt aggcttctct ttggaaattg tagacgcttt ctctccttcc agttacacgc    13680
ggtcacatca acatttgaca cgtgggtacc gtgcacgtgg cagcagtatt tacaaacacc    13740
atcctaggat tccagagact cttatgtaac agtggagaga gtaagctttg agtgtctgtg    13800
ggcggaggaa tcaacacagt ttaattcatt gtccgggagc ccttgtctgg ctctgatagg    13860
gtcatgaacc aaagatcaag gtgtttaggt caggatattc cctaacgcat ggttttccta    13920
ccaaagcctc aaaagctgtg cctaaataca agattaatct ttttctttct ttctttcttt    13980
tttttttttt ttttgagac ggagtttcgc tcttgctgcc aaggtggag tgcagtggcg    14040 ccgcgatctc ggctcactgc aacctccgcc tcaccggttc aagcgattct ccagcctcag    14100
acacccaagt agctgggatt ataggcatgc gccaccacgc ccggctaatt ttgtattttt    14160
agtacagacg ggtttctcc atgttggtca gcctggtgtt gaactcccga cttaaggtga    14220
tccgcttgct tcggcccccc aaagtgctgg gattacaggc ttgagccacc gcgcccagct    14280
aagattaatc tttttatgcc ctgcagcaaa caactagtca tgccaaacca tttttgtgat    14340
ttggggaaac atgagcagat gatgcttttgg atctgattat aattcacagt gctcttgtaa    14400
tttacgtgag atttgcatac ctgcctccca gcctcacaaa atgcctttaa aaaattacat    14460
cttggccagg atggctcacg cctgtaatcc cggcattttg ggaggccaag gcgggtggca    14520
agagatcgag atcatcctgg ccaacacggt gaaaacccgt ctctgctaaa aatacaaaaa    14580
ttagctgggc gtggtggcgg gcgcctgtaa tcccagctac ttgggagact gtggcaggag    14640
aatcgcttga ccccgggagg cggaggttgc agtgagccga tcgcgcca ctgcactcca    14700 gcctggcgac agaacgagac tccgtctcag aaaaaaaaaa aatcttgata tttgtatgca    14760
```

```
tcttaaaaag caagagaatt catgattgac ttcccaaact aaacggtctg accagaaaac   14820
actcaagaaa actcttggtt aatcatgctc cttagtatac cattatacct gcctctcccc   14880
tttccccatc ctctgtaaat tctctcaacc ttctctcatt tttaatttca taccaagacc   14940
tagagctaaa acaacaacaa caaagcttta agtctctata tttagggaat gtgcctccta   15000
tcccaaattg attttttagag cttttcattt atttttatca atacaaagca agttgaaata   15060
aaaaaaaagg catcaaaaat ttaaatgtct aaccacgtat atttggtata tgtatactgg   15120
tgctatgtat tagctgtaag cagactggtt tgaatattta aaatatgaac agaatttgag   15180 ttcttttttgt attgcatcta aggatcattt gagatggatg tcatcattta tcatccaaaa   15240
tagaagcctt cttgcctaac aaagaattgt aattagatca tcaaagatga aatttatagt   15300
aattgaaaag ttagctcatt tgactgcttc tttcatagac tgtgttttttg taattacact   15360 acctttctaa agataggaaa aatcagagtc tctgaaatgt aatactataa gtgaaatatg   15420 tatttttttaa aataaaggat cttttcccaa gagctaaacc aagcaccaaa tctgtttttt   15480
gggggttttt tggtttgttg gtttgtttgt ttgtttgttt ttgacagagt ctccctctgt   15540
cgcccaggct ggagtgaagc ggagcgatct gggctcaccg caacctccgc ctcctgggtt   15600
ccagcaattc tctgcctcag gcttcggagt agctgggatt acaggcactc gccaccacgc   15660
ccggctaatt tttgtatttt tagtagaggc ggggttttac catcttggtc aggctggttt   15720
tgaactcctg acctggtgat ccactcgcct cagcctccca aagtgctggg attacaggtg   15780
ttttctttta agtaatactt ggtataagag aactttatat ctggaataat ttaaatatta   15840
tctgaccgaa tctattattc acatatagaa actcaggttt tagccatttta acatctaaag   15900 ctgttctcat ttagaggaaa ttaccaaaag agtgacttat ttaactaaca ataaaatcta   15960
aggatagata ttttttcatt ctgttgcaga gcaaaagcag ccttctggat atgaaaagat   16020
attacttctt tagtgtttat tacttataat ttattgtaca tttctgatac actgaattaa   16080
gatgcgatga gagtaggttg tagatttttta aaagttctta tttgcgtgat ttatctactt   16140
gcttttttag tgtcggacta taaatgatgt atttctctca attatcctcg gcctaaatag   16200
taaaagcttg ggtgaaatta cttatgagta tacttttcct gcacagagca gagccattac   16260
tgaacactct cgagctttaa caaaaatcat cctatccttat attagaatat taatatttttc   16320 cctcttctc ggacctttgt ttcacagtaa atcatatatg gatataagct gcaagtgctc   16380
agaatttgat taaggctata agttaatttc tactaaaaaa gggattcaaa tagaactttc   16440
atttggctgt actgtagttt cacttgaagg ggcaagcatg caataaacat tgacttattc   16500
aatgcatagg ctgtcttcat aaagatgaga ctgagtgaca gttgtctgtg tattataaaa   16560
tatcagaatg gtagattgaa tctgatgcat accaaggagc aatgtggaaa ttttaggctg   16620
ttcgtctttt ttcagttact actaagtgtg tgtatgtggt gtgtatgtgt tttgaacttt   16680
tcatatttaa gctgaatcct cttttggtaga aatggttaaa tagactatag taaaagtttc   16740
tgtctataaa tataaaatga aaaaatactg atatcttgca ttttccctaa tatgttgaaa   16800
gtgcacagaa tccttggggt cttttgtata aactgttttt atatggttcc tgtagaagac   16860
agctgaggca ccaaacacac acacaaaaca aacagcttgc ttggtgatga taacattcgt   16920
gcaagggagt tctctcttgc ataggagtcc caggttaccc taatgccttc ccacatggtc   16980
aaacacatgg agctttcata tttacacaca gctccagaat tctgaagcct gcagttgttt   17040
atcagtggga tacagggaga aagagtggtg tctatcttac taactgttta atgacctgga   17100
tcatgaatac tgatacagaa taagaaagca ctggcctgac tgcaggggaa acatggtaga   17160
```

```
tgcctaaagg aggcttttcc ctgccccaca ctgtttattt taaactatca ttatcacctg   17220
aaaggagctt ttcactttga acttaaaata gtagctttta accctgacaa gcaagtaggc   17280
actttagtat tcaagaactg aaggtgacaa gccctgagga gtgttactct ctttcataac   17340
caagctgact caaactcttt tagaagctag tgtagtaact taaccatctc taataatgtt   17400
gctgcatgcc ttcatagaaa cagttggagc aagagctgca ttttcttttt tttaagtgtt   17460
tattatttac atttattttt tgaaaacatg ccattcctat tacatataga aatacttccc   17520
aaaatcactg tttgtataga actattttgc ttaacattag gattctattg aagagcctat   17580
atctgcaata atacggggag aaaatcccct tttgtgtgat agattaatga taaagagaaa   17640
gaaaaggtga gaagtaattt tgggaaatat gcaatgataa actagtggta tttattgaac   17700
taaacaccag cagctgtgct tagcatggat aattgcctaa aaggatgaga aaaaaagta   17760 aaaatcagga gactataaat ttttcagtga agaataaatt ttctgtcaca aattatgaac   17820 atttttaaata tgtattttaa acttttttcct acttgtaaca aattatcaga cttttttaatc   17880 taccttttttt gagcttttca tctttttccc tgaattatag atttaattct gtgtatgtat   17940
gtgtgtgttt gaatatattt ttatatttta gatctagatt tgtaaactag agctgtttct   18000
aactgcttat aagacattgc cacctggatt gccaccactt tcactccagt atttcaataa   18060
acacttcatc aaaaacatag tttattttca aacatagaat catggattgc tacaagctga   18120
aaggacttta gagactcagt aaccccattc cttgcattta cagatgagaa aatggaggca   18180
tgggaaagta aagtcagttg cctcaaatag cgtaacaagc tatgtatatt tctaataata   18240
gctactattg attaagttct tatgttgggt taagtaccat gctaagcact ttccaaagat   18300
tatctaattc ttatgtcatc tatattttg ttggtgctat tactctcctc actttactaa   18360
ggaagaaacc aagacatggg gttaaataac ttccctataa attttgaatt atctttggca   18420
tcatctccct atttgcaaat ctccattgtc tctttgttcg taatcaatgt aaatcaactc   18480
ttaaacagtt ggatgccaac aagcagtctg gtgtttggag ctcgaaagtt tcgagagaga   18540
gagagagaga gagagagaga gagagagaga gagagagaga gtgtgtgtgt gtgtgtgtgt   18600
gtgtgtgtgt gtgttccagc tttgttgagg tataattgac aagtaaacag tccacaaaac   18660
tgtacacatt taagagatac agtgtgatgt tttaatatac attgtgaagt gattattact   18720
atcaggctaa ttcacatgtc catcacctct cagtcatttt ttgtgtttac ggtgagaaca   18780
cttaagagct actcaaatgt agtcaaggat accatacagt actaactgta gtcaccatgc   18840
tgtacattag atctccagaa tgtattaaat attcatctgg cataactgaa actgtgtatc   18900
ctttgacaaa cctatttccc ctactaccca gcccatggca accaccatgt tactctctgc   18960
gtttatgagt tcgacttctt tagattccac atataagtga gatcatgcaa taggaagatc   19020
taatttagca tcctgacttt ccttttttatt agctgtgtat gtcatattca ggttgcctta   19080
gcatttgtga atctgcttct ctacctgtaa aatgagaaca actaataatt cttatctcat   19140
ggattactga gaggatcaga tgaagtaaca taaataaaac atccagcatg ttacttggca   19200
aaattgtagt gattgaataa atatttgttt attcttcaag catgtgttga gcatctatgt   19260
atcaggcaag aagagagcca tcatctttac ccttctggaa tatacaggct cataggaaat   19320
aatcaatgct ttgatctttt tttaaagcat aatgagatga aaattatagg actcatagac   19380
tggtcagttg aggaatttcc caggatgctt ccagcctctg ctcaaaaggt gtgaattccc   19440
agttgcctga ataggcgcca gagttggcat agctttctca gtattgggac ctgacaggga   19500
```

```
gattgcacaa gtgtaacagc acagcctctg aagattggct caaggggaa gagatgaagg    19560 attacttcca tcccttttat tgtttcaatc aagatatata ttatgagctc atagtaccat    19620
cctttcatga tcatccttta ttgtctttat tagatacaat gaaaagatac aaatttgtcc    19680
atagaaatat taaatgatag caggcatgat ttaaaaagta ctaaggacta tagatattac    19740 tgttttcct  ctattttgta tcatattttc aggaagaaga gacaacattt tggcatacct    19800
tgcttaaaga tagatgatag ccgggtgtgg tggctcagac ctgtaattcc agcactttgg    19860
gaggccgagg cgggcagatc acctgaggtc aggagtttga aaccaacctg gccaacgtag    19920
agaaaccccg tctgtaccaa aaaatacaaa aattagccag gcgtggtggt gggcgcctgt    19980
aattccagcc actcaggaga ctgaggcacg agaatcactt gaacccagga ggcagaggtt    20040
gcagtgagct gagatcgtgc cattgcactc cagcctgggt gacagaggga gacttcgtct    20100
cccaaaaaat aaaaataaaa aataattgtc ttggtgtgct aatcaggagc ttcctgtgag    20160
agtggaaatt ccttacatgg cagtgtcatg aaattttagg cccatgtgaa agatgttttt    20220
gagtgtctca aaatagttaa cggtttaaaa atacattatt tatgtgtcag aaactgcttt    20280
cattgaaatt gaagtttctt tgagaactag gatcatatca tgtatatcta ttgaatttcc    20340
cacaacaatt atcacgcaag caaatgaata gcagaccctc aataacactt actgatgatt    20400
attgccatgt ataagttggg atactcttga gtacctttct aagtctgcat ttagggaaat    20460
acagaacaca aaatgaaatg tttgattggt tgcttagttt ccacagtgac ttttcaaaat    20520
gtataggagc atggtaacaa aactatttta aatactacaa tcttaagtat gcctttatta    20580
ttcttaccca caataatgca ttgctttaaa aaattgttta tcagtgtcag accatacctt    20640
tctgagtctc tactatgtaa gatgtgaaag ttaatattct tcaattccag ctacttttct    20700
tttcctgcct tctgtcaact cctgtattcc atatcattac ttcttattgc taaatttata    20760
atatttatat tctggtttgc atctatagtt aattctcttg tgcttcattt ctcagtgcta    20820
attgaaaaag aaaacacatc acttacaatg ccatgattgt aataaataaa attcactgta    20880
acacctagca gtatggttga acatgtagaa aaggaaaaag tgatcctgtg acactaaaat    20940
ttagcttgtt ctaaggatgc tactttaagc attagggtaa aatggattcc cttttgctaa    21000
attctttcag ttcctcaaaa ttatgccaca ttttttgttc tttcacattt ggacttagat    21060
tttcctgtaa gcattcaatt tttcttgaaa attttaattg cattttttta ttcttgttga    21120
cagaagaaac attttcatca tatcacaatt ttttttcaga tttcttaatt ataccatttg    21180
atgaatgaaa tacactttct tcttgaagtc tgattttct  gttctaattt agagtttctt    21240
ctcatttttc tcctggctat gtctattatt gctttagtct catgtctttg tatttgatta    21300
ttatttttct ttttactact gttttctctt ttacagaaaa aaaaagaaaa aaaaacaggg    21360 gttttttacaa atattgtgct gagtctttac atgtccaaaa tgccttatat ttttccttat    21420
agtacattca taaattattg tgattagaac cataaattca aagtaatttt ctctcagagc    21480
ttgggaaaca ttggtacgtt gttacccttc atctaggatt gcttatgaga tagatatctg    21540
atgccagtct gattctgtct tttttagata acttttttcc ctattcatat gtttattagg    21600
atctttatct tttcacttct gaaattcctc cagatatggc tctgttaaaa tgtattcttc    21660
tcagcacttg atgattctgt acaatctgga aacaactgcc tttatttagc ttaaggtact    21720
tttcttccat tgtacctttg attatttctt ccttcttttt ttcaccctat ctttatgaaa    21780
ctcatgttaa tggtgcatta gaacttgtga actgattttt cttatttatt aaattccatc    21840 acatatttt  catctgttta tctctgtata ttttattttc tcaacttttg atattttgt     21900
```

```
taattgaaat ttaatttcca agaagtccat tttctattct ctgattgatt cttttaatg    21960 gtagcctatt tcgtggctca aatcatataa aatgtattaa attttgtggg aaaattaggc    22020
aaacaaagaa aattaaattt tacctaacta tatctaaaaa caatacaact aaacttaaga    22080
aaagtgcgta tatgtgtaca catatacata tgcgtgtata tgtgtacaca tatgctacat    22140
atacatgtat atgtagtata tgtacatgta gtatatgtgt gtatgtatgt atatacacat    22200
gtagtatatc tatatacatg tatatgtaca aagaaaaaat atgtatataa tagtttcact    22260
gtactttatt tgctcccctt ttaaaaataa cagtgctaga gttcatgact gactaatttt    22320
cagaacttgg tgtgtatggt tgtttattaa gccctcaata ataatgcttt agtattacag    22380
tgcccaggca tagtcagtga ctgtgctaat agtcctagca gtagcagttc atcctgtaca    22440
gatctaaggt gtaactattt tcatttctgg gcccttggag attctttggt tgtcttcata    22500
tcttttacct atcttgctgt tcaataacag gtaatagaaa aggagataaa acttaaatgt    22560
catcatttcc cactgcttaa cagtctttaa aaataaatgt gaaacccgta aggacgtaat    22620
cttgcctagc tttaaggaat gaaggaaaca ctagaaacaa cagagagaaa aggaataact    22680
gatcctccaa catgttctgt tgactctacc tgtaaagtat attcaggatc tgactacttc    22740
acaccatttc accaatttcc atctccattc aaaccaccct catgtgttac tttgaaaagt    22800
gcagtttccc tgtcatgggt ttccctgttt ctagctttgc tccccttct tacctcaccg    22860 tgggttttta cccaaacaaa aattcaagtg atcatttaaa aattaagtca ggtcatgcct    22920
ctcctctgct taaaaccatt aatgggtctc tgtttcactc agaatataag ccaaagccct    22980
tttcatgacc caccagtcct caagtgaatt ggctgctatt tgtgtttctg attccatttc    23040
ttgccactat tctccctcat tctattctaa tttccttggt tttcttgctg tcctggcaac    23100
aagaagagca tcctttttcc tccaggcctt tgcacttgct gttccctctt cctggagcac    23160
ccttccttca gagagccaca ggtattgttt ctatctttcc ttctaatctc tccttgagtg    23220
ttactttttc agagataaat tccctaacca ttctatctaa cagaactctg actattgacc    23280
ttgctttatt ttctctcttt ttttttaaaa ttttattttt ttattcccat aggttattgg    23340
ggaacaggtg gtatttggtt acatgggtaa gttctttagt ggtgatttgt gagatcttgg    23400
tgcacctatc acccgagcag tatacacttc accctattcg tagtctttta ttcctcaccc    23460
ccttcccacc cttttcccct gagtcccctag agtccattgt gtcattctta tgcctttgca    23520
tcctcatagc gtagctccca cttatgagtg agaacatatg atgtttggtt ttccatccct    23580
gagttacttc acttagaata atagtctcca gtccttatcca ggtcactgca aatgccatta    23640
attcattcct ttttatggct gagtagtatt ccatcttata aatataccac agtttctta    23700 actactcacc gattgacgag catttgggtt ggttccacat ttttgcaatt gcaaattgtg    23760
ctgctataaa tgtgtgtgca agtatctttt tcatataatg acttttttcc tctgggtaga    23820
tacccagtag tgggattgct ggatcaaatg gtagttgtac ttttagttat ttaaggaatc    23880
tccacactgt tttccatagt ggctgtacta gtttacattc ccaccagcag tgtagaagtg    23940
ttctctgttc accatatcca tgccaacgtc tactattttt tgattttta ttgccgttct    24000 tgcaggagta aagtattgca ttgtggtttt gatttgcatt tccctgatca ttagtgatat    24060
tgaacatttt ctcatatgtt tgttggtcat ttgtatatct tcttttaaa attgtctatt    24120 catgtcctta gcccactttt tgataggatt gtttgttttt ttccttgcta atttgttgga    24180
gttccttgta gattctagat attagtccctt tgccggatgc atagattgtg aagattttct    24240
```

```
cccactctgt gggttgtctg tttacgctgc tgactgttcc tattgctgtg cagaggctct   24300
tttgtttaat taagtctcac ctatttatct ttgttttttgt tgcatttgct tttgggttct   24360
tggtcatgaa gtctttacct aagccaatgt ctagaagggt ttttctgatg ttatcttcta   24420 gaattttttat agtttcagca cgtagattta agttttttgat ccatcttgag ttgattttta   24480
tataaggtga gagatgagga tctagtttca ttcttctata tgtggcttac cagctatccc   24540
agcaccattt gttgaatagg gtgtccttta cctactaatt tatgttttttg tttgctttgt   24600 caaaggtcag ttggctgtaa gtatgtgggt ttctttcttg gttctctatc cccccattgg   24660
tctctgtacc tattttttata ccagtaccat gctgttttgg tgtctatggc cttctagtat   24720
aaagtcaggt aatgtgattc tgcccaattt gttctttgtg cttagttttg ctttggctct   24780
gtgggttctt ttttgttttc atatgaattt taaaattgtt tttcctaatt ctgtgaagaa   24840
tgatggtggt attttgatgg gaattgcata gtttatcaac ccttggcaaa gtgtttctgc   24900
ttttcttaaa caatttttat tgtctgcttt ctccagtaga tgtgagttct atgagatgag   24960
gaacattgtt tgggtcactg acatgtattg tcagcatacc aaacagtggc tagcacatgg   25020
tgagcactca ataaatattt ggtgaaagtt gcagtgaatg aaaatggttt ctaaaatggc   25080
aatgactata gtcccagcta ctctgaaggc tgaggcagga agattgcctg agtctcaaaa   25140
gtttggggtt gtagtgcact atgattgtgc ctgtgaatag ctgctgcatt gtagcctggt   25200
caacacagtg agaacccatc tcttaaaaa aatggcaatg aaataatctt attttttactg   25260 cttttctctt taaggctgcc agtgttgtct tttctctgct gatttatcct cattggaaat   25320
tgaagataga taaaatatcc attgattatt tataggtgaa attaggcttt tggatccatg   25380
aggaatagct gagacaatct tccaggagct tctggagccg aggaaacatt ggtcactaaa   25440
ataccattta tattggcaac tgtactcttt tccgatgcta gtgtttcaat tacattgtgc   25500
atttaaaagg ctgttgcggc tacctcaaaa tataaacatg atgtgcgaca ctacttgtta   25560
gttttgaaca actgatttat aaatagactt agggtgctca agcctcctgc aagatgagca   25620
ctgcctgtgt tcttccttct gcttccttta tttcagctgt gtgtctacca acttcctcct   25680
ccttctacac taggagaaat tgcactgttt ccaatatctt taacatctgc tatcatgatg   25740
agaaaatatc ttttctggat ttgaaatacc ttcttcattc ttttttttta aatggcggaa   25800
ataaattcat agtgttttga gtgcagtttt cttcctgctg ttattgctgg ctcaaaatcc   25860
aggagcattt cagtgttatt tctgagctcc atgatgggag ttccatttct gttttattca   25920
aagtgttatc tccagtgtct agcacagtgc ctggcacatt ataagcctat aatgtttatc   25980
tagtggatgt agaccaatac tattaaagaa ttatcattgc aaagatttag tggcatgaaa   26040
aaatgataat gattaatgct ctactccatg ctaaggaaat gaagtgcaaa tcgttctttta   26100 tttttcttcc aagtatagag aactttctga aattaaagaa gcattgatta ataagtttta   26160
atatatgtta ttgatcataa taatatgtaa tcatataacc aaataagata acacaggcca   26220 tctttttgttc tttaaaaaat gacaggaaga ttagaataag agaaaaaatt agaggtcaaa   26280
acagttttct tcaaaccagt agtgtaactt actgagatat cttctgtaat ccttaaattc   26340
tgtattgatg ctaccaagat gcaactcttg agctacaact gcctcttgat aaaggatgct   26400
ggtccctgct gccagtgtaa tgtttgctca tttacagtgg aatgtacaat atagtacctg   26460
ggatggtgaa gaaggtgaag caacaaattt aaaatagctg tgggtaaacc tacagaaaca   26520
gactattctc tttcttccag attgcattat tcatttttcat atgcctgcct ttatctgctt   26580
tggaagccta tttcctaatc ttccaagatt tatcatcacc ttcatatgtc catagcatgc   26640
```

```
atttctcaga caggtaagat agaattggta tatatttggt atagcaaaaa gtcaaggttg   26700
tctttagatt atatccttgg tttttcatgt ggtactgggg agaaagccta ctgtttcttc   26760
atctataaaa tgaaggacct gggcaagata acattctgtg aaatttcact gaactttgag   26820
ctcagcaaag tagggatgcg tgtgtgtgtg tctatttgca atgcatcaca gaccttaaat   26880
aaatacagtt gacccttgaa taacatggag gttaagagca ccaaccccct gcactgtcaa   26940
aaatccacat gtaattttg actccccaaa aacttaacta ctaatagcct gctgttgtct    27000
ggaggccctg ctgataacac acacagttga ctaacacata ttttctatga tatgtattgt   27060
gtactatatt cttacaataa actaagctag agaaaagaaa ctgttattaa gaaaatcgta   27120
aggtaaagaa aatatattta ctatttatta aatggaagta gatcatcata aagatcttca   27180
tcctttgttg tcttcacctt gagtatgctg aagaagagga ggaaaaggat gggttggtct   27240
tgctgttcca ggggtggcag aagtggaaga aaattcacat ataagcagtc catgcagttc   27300
aaacctgtat tttaaggtca acggtatttg ttacattgca ttttgtaagt gaccttgtta   27360
atttttttca atgaaaaaaa tagtgttcca ttcaaatgcc tgtatgttta tgagaaacat   27420
ttcagaacta tgaaagttga attcaaggtt cttgcagat tgtttgtata ctttctgtaa    27480
tgtttgtcat ataatgagaa tactaatggt cttacaactt gaaactgatt aactgattaa   27540
ctctttaagc aacttaaaaa gaaaatcttt cagtgaggaa agagtattca tcagaagtat   27600
tctagtagat gacatatttt tggtaatgaa attgatatgg gcaattaaca gcttttttcca  27660 agttggctat gctgctactc tcttattata caatgatact attttttcaga gcagaaagca  27720 aattagttttt atttttataa accaaatttt aaatatccct ttagagaata gaaaatatga  27780 aaaagtatttt gcttctcaga cctctcaaca atataaattt tcttcttaag aggaaattta  27840
ttcttgcatg ccaacacaaa ggataaaaag tttacctatc cttagttttct aagaggaaaa  27900 tgtgcataaa atttccatct gctgtgtgcc agttaccaaa acgataagtt ccaactcaat   27960
cttggttggg tgtggtggct cacgcctgtg atcccggcac tttgggaggc cgaggtgggc   28020
agatcacgag ctcaggagtt tgagaccagc ctggccaata tggtgaaaac ccgtctctac   28080
taaaaataca aaaaaaaaa aaaacaaaac tagcccggca tggtggtgtg ctcccgtagt    28140
cccagctact tgggaggctg aggcaggaga tcgattgaa cccaggaggt ggaggttgca    28200
gtgagccaag attgcaccac tgcactccag cctgggcaaa agaggagac tctctctcaa    28260 acaaacaaaa aagactcaat cttactaaaa aactgcagag aagaatgagt cattttagtc   28320
aataaaggaa ataagaaat tctagttttg aaaatgacat aatttgctac aagaatgcaa    28380
aggtgatgac atgaggaaaa aagggggtttg ctgatttgtt ttctctacta ctcagcaaat   28440
gcaggccagg aacccatttta ttcaaatatt tattacatgg taaattaaaa catttataaa   28500
attaggctca tattcttaga attcctgtta acaaagtgac atataaacaa gattataatc   28560
taatggagat taatattggt tgagaaaaat cttgagactt ctttaagact tcagtttaat   28620
aaaatattga cttaggtaga tatatgtgag gaaatatata ttttacccat gcatgcaaaa   28680
atgatgtatg tatttcttaa aagagtaggt agcaatgact tcaaaggacc atagctgtcc   28740
ctatcaacat atatattaac aaaacaatta gaaacatgag cttagtatgc taattatatt   28800
tctacccaaa gcctcaattt gttctatagc tatactgttc atatataagt aaaattttag   28860
gggtatcaga gagagttaga aaagagcaaa tacatgtatg aatttgataa gcctatccct   28920
taatttgata gatcttaaaa gatattttat cactgcattc ttctaaagaa atgtatttgt   28980
```

```
acattgcaaa caacccttt ttgagaagta gactatgatc acagattttc ttgccactag    29040
tatttcctaa gatttatttg aatagaaga tcgatatttt tctgggatga catatggtta    29100
aaaagtaaaa aacaaaacaa aacaaaaaac tctttaaaaa cacaacaagt aaaaagctga    29160
atgaattgga aaattaacga atcttcttag atctgtcaga aaaatgagat tatagggcaa    29220
accactgcat caaatattag agaagcagac aggtagatag aaagaatcac aacttagtgg    29280
ggcaaaaacc tacaaggaaa atttttgtgg gaaccggtgc caggtaggaa aacatgaact    29340
gtaattgaaa aattgttcag tgtgggcggt tgttcagtgt ggcaagtctg agggttaaaa    29400
actccaggag gactcactta cggaagggcc tgtacttttg tgagtttaac ctccaggagt    29460
gttcacagtg actactggag aaaattccct aaggggagaa gaaaaggaac catcttgaaa    29520
tatgtcagag cattttgttg gactcaagcc tgctctcaag tgaaactatt ttaccagagc    29580
ctaaactttt gggattttat aagagtgtaa cctcccaaag ggaagggaaa tacctaagtt    29640
cagccccctt ttagctttcc acatagggaa aggaaaatat ataactctgg acaactcaaa    29700
ccatcctgtc cacgttaggg ggcctagggg aactgagaaa actggtgaag ttcatagtcc    29760
atgggtacag tttcaccaaa gagggagacc aaattataag gctacagaat gcttcccttt    29820
cccacacctt ttactatcat attactaaaa gcctatttgc agcagtttct tttactgagt    29880
atatcatgtc tgtcattcaa ccaaaaaatt ataaggcatg ctaaaaggca ggaaatgcag    29940
tttgaagaca ctgaataagc atcagaagca gagtcaaata tggcagtgac attggaatta    30000
tcagaccaga aactttataa aaaactatgg ttaatatggt gagggattaa aaaaatgaca    30060
tacaagaaca gatggataat gtaaatatag agacggaaat tttaggaaag aaccaaagag    30120
aaatgccaag tatcaagcat agtgtacaga aatgattaaa atgtctttga taggctcata    30180
agtagattga acatagccga ggaaaaaatc tttgaagtta aggatatgat aataggaact    30240
tcaaaactaa aatgcaaaga gaaaaaagac tgtgaaaaaa acagaagaga ttattcaaga    30300
actgcaggag aactacaaaa ggtataatgt acgtgcaatg ggcatactag aaaaagaaag    30360
aaaggattag atgcaatatt tgaagaaata gtgtgtgaaa atctccccca attaatgtca    30420
gacaccaaac tacttctcca gagagctcaa agaacaccaa gcaggataaa tgtcccaaaa    30480
ctactcatgg gcatattata ttcaaacttc agaaaatcaa agattaaaaa aatatcgaaa    30540
gaatccagaa ggaaaaaaca cctatagagg agcaaaaata ataaatttta tctgacatat    30600
cctcataaac catacaaata agagagtaga gtgagacatt taagatgttg aaagaaaaat    30660
ccggcagtgt acgattctgg accttgcaaa attgtccttc agaagttaag aaataaagtc    30720
tgtcttaaag aaacaaaaat ttcaggaatt tgttgccagt ggaccaccct tgcaaaaaat    30780
gtttaaagtt ctttagagag aggtaaaatg atacaggtta gaaactcaga tccacataag    30840
gaaaataaaa ttagggatat agtagtattc cccaacttga taaagaaaat acacaaaaaa    30900
cctacagttt acatcatact taatttttag aaactcaaag cttttcctgct aagatcaaga    30960
acaagacaaa ggtgtctcct cttaccactt tgtttcctac tggaagtgct acctaatgca    31020
ataagacaaa ggaaagaaaa tgaaaagcat acagattccg gaggaagaaa tcaaactgtc    31080
tttgttcacg gatgacagtt gtttatatgg aatatccaaa ggatcagaaa aagaaaact    31140
ggaactaata aatgattatt gtaaggttac agaatacaaa cttaatataa agaaagccaa    31200
tcactttcct gtataccagc aataaacaag tgtaatttga attaaaaaca cattaccatt    31260
tacattagca ccccaagaaa tgaaatactt ttgtataaat ctaacagaat atgtacatga    31320
tctatatgaa gaaaactaca aaagtgtaat gaaaaatacc agtgaactaa ataatgaaga    31380
```

```
gatgttacat gttcattgtc aagatgtcag ttcttcccaa cttgatctat agattcagtg    31440
caatgccatt aaaaaacaca gcacgatatt ttatggatat caacaaaagg attctaaagt    31500
ttatatggag aggcaaaaga gcagaatagc caactcagta tttgaggaga acaacaaagt    31560
cagaggactg acactacctg gctttaaagc ttactataaa gctcagataa tcaatgtagt    31620
gggtactggt gaaagaatat tcaaatagac caatggaata gaataaagag cccaaacaaa    31680
cccatgtaaa tataatcaaa tgatctttga caagggagca aaggcaatac aatggagcaa    31740
agatggtctt ttcaacaaat aatgctggaa aaactacaca ttaacataca acaacaaaaa    31800
ttttttaaat ccaaattgag tgtaaacaca gatcttatac cctttgcaaa aattaacttg    31860
aatcatagac ctaaatgtaa aatgcagaac tataaaactc ccagaagata acacaggaaa    31920
aatcctagat gactttggta tggcagtggc attttttaga tacagctcca aaggcacgat    31980
acatgaagga aatgattgac aagctggact taactaaaat ttaaaacttc tgctctgtga    32040
aagacaatat taagagaatg agaagacaag ccacagatgg aaaaattatt tgcaaaagat    32100
acttctcata aaggactatt gttcacaatg tgcaaacaac tcttacaact caacagtttg    32160
aaaatgaaca actcaactta aaaaatgagc aaaaaacctg aacagacaac tcaccaaaga    32220
agatacacaa gtgtcaagaa agcataggaa aagatgttaa acatcatagt cattagggta    32280
ttgaaaatta aaacaacaat gagataccgc tacatacctg ttagaatggc tgaagtcaga    32340
acactgatga aaccaagtgc tggtgagaat gtggagcaac aggaaccttc attcattgct    32400
ggtaagaatt caaatggca tagtcacttt ggaagacagt ttggcagttt cttacaaaat    32460
aaacatactc ttcccatatg attcagcaat agcgctcctt ggtatggact tgaaaactta    32520
tgtcctggcc gggcacagta gctcacgcct gtaattgcag cactttggga ggcccaggca    32580
ggtggatcat ttgaggtcag gagttcaaga ccagcctggt gaaatccat ggtgaaaccc    32640 cagctctact aaagatacaa aaaagtagcc gggtgtggca gtgtgcgcct gtaatctcag    32700
ctactaggga ggctgaggca ggagaatcac ttgagcccag gaggcggagg ttgcagtgag    32760
ctgagatcat gccattgcac tccagcctga gtgacagagc aaaactccat ctcaaaaaaa    32820
aaagcaaaaa caaaacaaa caaacaaaac ttatctccac ataaaaacct gcacacattg    32880
tttaacagct ttacataatt gccaaaactt gggtgcaatc aagatatcct ttaatatttg    32940
agtggataaa ctgtggtaca tccagatgta agaatattat tcagcactaa gaaatgagct    33000
atcacatcat aaaacgacat ggatgaaact taaatgcata ttataaagtg aaagaagcta    33060
atccgaaaag gctaaatact gtatgattcc aactatatga cattccggaa aagccaaaat    33120
tatggagaca gtaaaagag cagtgttttc cagagggagg aatgtatagg caaattttta    33180
gtgcagtgaa atgaatctat gtaatactat agtggtggat ccatgtcatt atacatttgt    33240
ccaaacacgt aggatgtaac caccaatagt gaaccctaat gtaaactatg gggtttgggt    33300
atcaaaatgc atcaatgtag gtttatcagt tgtaacaaat ataccactct ggtatggat    33360 gttgataatg gggaaggttg tgggtctgtg gggacagggg tatatgggaa ctttctactg    33420
ttttactgtg aatcaatttt actgtaaagt ttattaatgt taaaaatttt aatgcacatg    33480
taccctaaaa cttaaagtat aataataata aaataaattt aggcaatctg aaaaaatgtt    33540
aataaaaaag aaaataaact agttgaatgt atcagttcat tttcatactg ctataaagta    33600
ctgcctgaga ctgagtaatt tataaaggaa agagatttaa ttgactcaca gtttagcatg    33660
gctggggagg tctcaggaaa cttaacagtc atggcaggtg acttcacaaa gtggcaggaa    33720
```

```
ggagaaatga acgcagaagc aactaccaaa cacttataaa accatcagat ctcatgagaa   33780
ctcactccct atgatgagaa cagcatgggg gcaactgccc ccatgatcca attacttcca   33840
cctggtctct gccttgacac atgggtatta tggagattat ggggattata attcaagatg   33900
agatttgggt ggggacacaa agcctaacca tatcagtgat aaaactatgt cttttctttt   33960
atggggtgct atagtgtttc atttcaagtt gtcttttttga cctccatttt ccaatttctg   34020
gttaggaaaa ataactttgt ctcctcctta attgacccac aaccttgttt gcaatgaaga   34080
atcaacacaa atctttcatt aaaagaaata ggggaggtga tggggatat ccatgagtgt   34140 ccatgggcat aattcagttg ccttcattca atgccaatga tactgcaaag cctacaaggc   34200
aaattcatgt acctacagac agactccatc cttttctca aactattcaa gataaaaat   34260 cttgtttcat tttatgtgag gatttttttc accatctatc ctcaaaaat gaaaatatc   34320 ctcttcattt gggaaatgag tgcttataat agaaagtaat ttgtagtcag ctgttacact   34380
tagatgattt gtgtcacctc tgacctgctt tctgataatg catgacttca ttcatggctc   34440
tctaggtgac ctgtgtaccc tgacctggca taaaccacta gagtattaag tcatttcagt   34500
ggcacatgtt tgagggaaga ttgacatccc actggaagac tatctacagt gagatcctct   34560
aaagcagctg cattcctagt gaggcatgat taagtttatc ccactattag gttctggagt   34620
attacttgtc atgcccaaga ggaaagtttt tctagcatgc agagtatctg gtttttaatg   34680
gctactgagc tgaaataaaa tgtgcctact aagggttgtt catttgtctg tctcccttct   34740
ttcactgttt ttttttcttgg aggttacagt agttatgcct ttctggtcag ctggctgttg   34800
acctatcata gaaatgacac tttcacatct tcaagtgtaa ggaattagat gttccagcct   34860
tcactttgtt tctcatccaa aatcaatgac aaaactttca gtattgattt ctcatggcct   34920
atgaacctga gtcaacttgg cataaaggac ttttcagaca agcttctcta aatgcagagt   34980
cagtggcttc tttttgccaa actccacttt gctcagtgat aacattaaaa tggtgatttg   35040
attcattcct agtctaaaaa tacttcctca tattccaaaa tctcagtcat taatacatgg   35100
aggaaaatac aaattattac atgcctgtgc ttctcggctg ttgtagatag ataaaatata   35160
tacaattgtg ttctataatt attgagttct tttaagtttt atcttttttt gttttaccag   35220
gaagcaaaat tatgtttatt tcagagctta tttactgcat ttagaatctc atgacactta   35280 aaaaacctttt ctaaaacgta atattctcc atgatctcca tggtcacaaa cagtatttca   35340
cgttctaatt gatattgcca ttttatcatt tttttttttt tcttggagac agtctcactc   35400
tgttgcccag gctgggatgc agaagcacga tcttgcctca ctgcaacctc cacctcctga   35460
gttcaagcga ttctcctgcc tcagcctgcc gggtagctag aattacaggc atgtgccacc   35520
acacctggct aattctgtat ttttagtaga gacagggttt cacgatgttg gccagactgg   35580
tcttgaactc ctgacctcag gtgatccacc caccgcagcc tcccaaagtg ctggaattac   35640
aggcgtgagg cactgcatct ggcccttta tctttctttt aactcaaatc ctcaaatata   35700
tccctccatg tgaagttgcc ttccctaatt atgtactgtc ctagtttaat cttcattcct   35760
tgtttgcctc tataaaacca agtttaaaaa tagtctctga ttctgtaaat catcactctt   35820
atgctcattt atatttctat ctagaatatt ttaaatcctt tgtaacaaag tttctactat   35880
gcagtctacc tttctcagct acgatctata tactccttgg ccatgtcttt tgttattgtg   35940
tgtgtttgtc tttgtgtgtg tctgtatagt agtggtttgt aaattctcca tttagtcaca   36000
atatgctttt tgaggatttt ccttttcctg ggaattctt gatgattttt attttgtcat   36060
gtgatgaaga atgtatgtca aagcaccact gcagaaatag tgcttttcta tttacttgca   36120
```

```
ctcttccatc ttagaagagc tggtgataga caaccgactc ttcttttatc ttggtttcta    36180
caacacagag gttgctaagc gactttaatc ccttttaaca caggacaatc aacaacaaat    36240
tccttctttc tttagattca gatatttcac ttagaaaatc tagcaaataa aaaatggttt    36300
aaaacttctt taaaatgtgt aattctgtac aatctcctac atctgtaacc cctgccccaa    36360
atatttttta cttatgctat ttcttgagca ttatgatatg cttattcata ggcaatcaac    36420
ttgtaagtag caatagtgta gccccttcta ggaaatcgaa gatgtgaaaa tccagtttaa    36480
tgtgataatg agttactttg atgaaaaata ctatgtcaca atttgttata aaaatactca    36540
tttggatttc tgattcactt atattaccct ccaaccttaa gtatgattga atttatagct    36600
ttttatacta ctttctttat ttagggagga gtgtatttaa attctgttat ctcggttatt    36660
acttgaaagt tcaacctcat actttcattt ttatataatt ttaatattat gaaaatattt    36720
tatgtaattt tatgtataat tcgaaaacat ttttaaatat tgcatcttta aatttttatt    36780
tcttttatca aatttttccct atcatttgtt ctctggctac aaccaaagtt aatagttaca    36840 ttttttttcca gtgacaaatg gtaatttgca aagacttgta acagttgctt aatactttt    36900 tatcccttat ttaagaatca tgcaaacaac cagagctgat aggcagcagg tgcacatgag    36960
tgtggctgtg ctgatggtta ctgaaagatt tccaaggtag ctagtaattc tgctacccta    37020
agccactata gctccttccc cattactccc tgggtctacc caccatcctg cagctagaat    37080
aataaatggc atgtaggttc ctctaggatc ctcctccagc actatgtctc atgcctggac    37140
atatgagctg ttaaatattt tgattatcac tcctgtgtgg taagggagac gtctacttgt    37200
cgtaacttga tgtttactaa actactttta agattaccttt atgataaaag tagacacttg    37260
caattttgca gaatgcatag tttgttttta acaaaccagg taaacataac tgcagagttt    37320
tcctatacgt tttgaaatct ttaaaaaagt attttttatt tgcctttcta ttagaaatag    37380
attagataaa aatttccttg tttcaatttt tagaatgaac attagagaat attgttactg    37440
aaggaatttt tttaaaaata gtgactgatc aaatgtcagc agctttatac tatagtgtaa    37500
aattttattt tgtagtttgc catcccatta agcattagaa ttttttataat tgatcctttg    37560 atgtttatat tcatgatatt aatgtaatgt ctttaaacct tagctcatat aggtcatatg    37620
acttaaagca tccttagatg aagatatttg ggctataaat aatttatgac ataagtgatt    37680
taaaaattca ttctttccat ccattttgaa gaaattgtaa ggtagggttc atgtatacct    37740
aatacttatc cccccaaaat acgaaaaata aaatcatttt taaaatatct gggttaatgc    37800
tatagattgg aagcagtttt taaaaagcac ttaaagtcta ccagtttatt gatcctcaat    37860
ctgtggctgt tttaaatgga tgcaattagc agttcagtct aagagaacca tggtagtaga    37920
ctcattactc cccagaaacc attacatcat tttgtaatat taaattacta aatataagga    37980
atagaatata tattgtaaaa attgctttgg aatcaataat aagtattgtg gctatcaatt    38040
atagttatat attacaatgt aagggatatc cttttataaa cttaatatca cacaagtaga    38100
cttagaataa ttccattaat ataattttgc ttgtgttttt atacctattc atttcaataa    38160 ctcttttttcc tatatatatt ttttatctca aattcgatag tatctaaatc atggaatcat    38220
aaaaccttaa agctgggttg gaacagaaat aatacaattt aacatcttat aggctctcta    38280
gtcctcagtt tccctaagtg atcggctcaa gatcatgaat ttatggagga ttagagtcag    38340
aattagaacc caagattaat ttatactttg ttatctcttc tacagcctac ccccttagtt    38400
tgcctgtggg tttatggaag ttacaggaga gacattctga gattcagcta aaaacctagc    38460
```

```
tcccaataga attattgccc tgtagtcagc cgcgcaaata caatcacaaa tacctgaagt    38520
tccttgtgtg aagaaaaaga aaatgactat taaagcatca aaatcaatgc aagttacctt    38580
tctttgcccc tttcttcccc tttcactcct ttcttctcct atactacttg aaatttctag    38640
cggggatctc taaaatgcct ggatgttagg aatggtaagt ctattgtaga gaattatatt    38700
ttctatttta gtggatgaaa aataaaccat acccttaaga ggcttttcaa agttaagatt    38760
ttgagcacat ccttcattgg cccagtctct gaccagtgag gtcaagtatt agccagtgtc    38820
agaatgtcgt gaaaagtttg tgtttcagat gcagaatttt ttttttgcatt ttctgtgtga    38880 tgtttatagg gtattttctt ctgaaatgtt ttccatcttg gttttttaaaa atatctatta    38940 ttttaaaaaa tattccctca taacttcttt ttattttcgg aaactatata aattgatctg    39000
ataatctata cacaatgcct tgtgaattta tacctgtacc tctcatgttc cagtgtttgg    39060
ttcttaaata atcactttgt ataatggaaa tactatgtta aattgtttat aactggtggt    39120
tgatatttca gccttgtttg gctatcgtag ttatataaag actgttaatt agaaacaacc    39180
tcatatggtg tatgcttgtt tttatcttca tggaatttgt tctgcaaaca ctgagttctt    39240
tactgggagt caccactttg tctatgttag gaggagcagg aagtgaatac atttaaggtc    39300
tttaattttc ttcttaaaac tttgactact gtagtggttt tttaaagcat taacaggaga    39360
atagccatca ctgccaagta gctgacattc tgaaatagca cttccccttta ggcactgtac    39420 agttggaatc atttacttgc agagaggtgt gtgtgtgtgt gtgtgtatttt atgtgtgtac    39480 tcatgtgtat aagaatagga gaaacacttt gtgggcatat cctgctgagg tgagtaacgt    39540
gctgattagt gaactccagt ctcatcccat ttaaacctgg aggagaacca catcaagcac    39600
agaagcagcc aaagcagcat ttcaacagga aggaaacatc tattactggg gctttgaaga    39660
aacatgccat gaaggtgtac taatatcaca aagggaaggg aaggactaaa ttcagcatga    39720
taaacaaagt ccctttttttg taacggaagt gtttgatgat gtttgatcaa tggtggatct    39780
atctcttgaa aggaaaatgc atttaaaccc caaatggagg attcttatat aaggtgccta    39840
gcttgtaatg atatattcat gtttataggt agagtgactg gttttttagag aagaggtttt    39900 ttttttttcct tcattttttga acgaaaactt gtctgtctct aggctttgaa atgtagaatt    39960
atttaccttt ccccaaaatg aaatgtttca ctgaatctcc tacaagcttg tggaggccat    40020
gaagcatgtt gaataagagc acaggctctg gaggccctgc cacccacaaa gggtgtgcta    40080
aggtaaacaa ctgatagtat tttgaaaatt agatgactta gaatccattc aataaatttt    40140
agctattttt attgtcttttt ttttctaaat ctatttggaa aatattgcag ataaagtaga    40200 taatacccttt ctaaaacaca gtgagaccag gcgcagtggc tcatgcctgt aatcccagca    40260
ctttcggagg ccgaggtatg cggatcacga ggtcaggaga tcgagaccat cctggctaac    40320
acggtgaaat cccgtctcta ctaaaaatac aaaaattagc caggcgtggg ggcatgcgcc    40380
tgtaatccca gctactcagg aggctgaggc aggagaatgg cgtgaaccgg ggaggcggag    40440
cttgcagtga gccaagatcg caccactgca ctccagcctg ggctacagag caagactctg    40500
tctctaaaaa ataaaaaata aaatagaaac agtgaatagt ttataaagat aaaatagaat    40560
aggcttcaat ttagggaaca aaggaaaata tgtttaggaa tgatattatg ctcaaaatga    40620
ttgcaacttt gatggtgaag tgtatttttat tcaattaaaa atgtagatat ggctgggcgt    40680
ggtggctcac acctgtaatc ccagcacttt ggaaggttga cgcaggtgga tcacttgagg    40740
ttaggagttt gagacctgcc tggcaacat agtgagacct catctctaca aaaataaac    40800 aaaaaatgtg ctgggtgtgg tggtacatgc ctgtagtcct agccacttgg gagactgaga    40860
```

```
tggaaggata gcttgagtct gggaggtcag tgctgcagtg agccgagatc gtgccactgc    40920
acttgagcct gggtgacaga gcaagaccct gtctcaagaa acaaacaaa aaaacaaaaa      40980 caacagtaga tatgtgtgtg ggaatgagaa catttaaatg tgctcatcgg cttagatttt    41040
tctttaaccc ccttcatggc ccttatctta acctctgtct tcagcactac ccttcatatg    41100
tttgttccgt tttatcttct aagtgatttt tttataactc tcaatgtatc atggcagaag    41160
gaaaactcag tgtataagct gactgtattt tgcatttct tttttttttt ttttttttg       41220 agatggagtc tcactctgtc acccaggctg gagtgcagtg gtgcgatctc agcttattgc    41280
aacctccgcc tcctggaggc gattctcccg cctcagcctc cccagtagct gggactacag    41340
gcttgcacca ccatgcctgg ataattttta tattttagt agagacgggg tttcatcatg      41400
ttgtctaggc aggtctcaaa ctcctgacct caagtgatcc acccaccttg gcctcccaaa    41460
gtgctgggat tgcaggcatg agccaccgcg gcctggcttc atgatccaaa atagcatcat    41520
taagcttctc tttcaaaaca tgtatataag cctgtgagtc atcactgtat ttatcagaat    41580
attatcatat tggagacttt gcaaagctga acaaagccag aattattggc tactgaggaa    41640
ctatattcta gcaagagact attctatttg ttggggatca cctcttttta ctaaagggga    41700
ctgttttggg catataaaac tagaattcat ggtttctcct tgatagtttg ccagcttgat    41760
tcccagtcaa ccagataact gctggtagtg acactcatgt cctccaggac tcccaatctt    41820
gtgccagctc agagagggaa atcccccctag aactgctcac accattccaa gaaccacaag   41880
caccaccttg gtatagttaa aaatgtgata ccaactcaaa ttctgataaa acaagttct     41940 ataaagctta ataaagttat attttttact ttttaagttt tgttttacta ttttaaacag    42000
aaaacagaag gtaaaaactc ctctgccttc ctcagtattt ggtttgtcag ttgctgaact    42060
cagatttaag agtctaatca tatacaggca ataaccctct tctaatctta ataatgtttc    42120
tttgatcatt tctttaaaaa gaaaaatgaa atagcctatt gactccaacc ctgacctcct    42180
gtacttcacc tgcctgatga atatttattt ggaatacata agttttttca aatgcatcat    42240
gtcaagaatt tgtcatttca gattcctttc tagaattatc tatttatctc attagtagca    42300
tcattctttc agacaaccaa actcaaaagc tttatcacta taattgaatt tcttttttct    42360
tcttacattt aaaatgttac taaatgccat tcatttcttt atcagtaata tttctgtttg    42420
atcattttat ttcatttatt ctgccaccct tcattccaa ctattgctta tacttgagta     42480
ctgcaataag ccaatatctt gcatatgatt atttataaca cctaaatctt ctaccacttc    42540
acactcactg ggatggatat aatttttaaa acatacaata acaggtgtta gtgcggtat     42600 ggaaaaattg gaaccctgac acattgctag tggaatgtaa aaaggtgcag ccactttgca    42660
aaacagtttg gcagttcatc aaaagattaa gcatggaact accataagac ccagtagttt    42720
cgctcttagg gattccactc tcaagagaat tgaaaacata tgcccataca aaaacttata    42780
aacattgtat atccatgttt gttgcagcat tattcacaat agcctaaagg tagaagcaac    42840
ccaaatgcct acagatggat gaatggataa acagaatgtg gtatagacat acaatggact    42900
attattcaac cttaaagagg aagaaaattc tgacacatgc tagaaaataa atggatcttg    42960
tatacattct actaagtgga ataagccaat cacacaaaga aaatattat gattccactt      43020 acatgaggta cttagaatag tcaaattaat agaggcatac agtagaataa tgattgccag    43080
gggctgggag gaggagcaaa tgggaagtta ttgtttaatg agtatagaat ttctgtttag    43140
gaagatgaaa aagttctgga gatgggtggc agtgatggtt gcacagcaat gtgaatgtac    43200
```

-continued

```
ttaatgccac agaatagtat acttaaatat ggtttgaatg gcaaactttg ttacatacat    43260
tttatcacaa ttaaaaagtt tgaaatgaat atccaaagaa gcattattta tgaggctaaa    43320
agtggaagta acccaaaagt tcatcattga tagctaaagg aaacatggca tatcaaaaca    43380
gtagaatatt agtcatacaa aggaataaag tacagacaca tgctgcaata cagatgcacc    43440
ttaaaaacat tacactaagt gaaagaaacc agacgtaaaa ggccaaattt tgtatggttt    43500
tatatatata aagtcgttca aaataggaaa acccataaag actgaaagtt gattagtggt    43560
caccaaggcc cgggggagga atgaatgaaa actggctcct aatgggtact gggttttttg    43620
gggcgagggg gacagagtga tgaaaatatt gtagaatttg atagtaatga taggtgagag    43680
tggcataatt ttttttaata tactaaaacc cactgactca tatactttac aaggatgtat    43740
tttatggtat gtgaattata tctcaaaaca cccccttaaat tttaacgtat ggcttttatg    43800
atgccatgtt tctaaagaag caacgtgtcc cagtctcagc ttactatttc taggcatgtg    43860
actttgagaa aaaattaaga gacctcccctt cttactctgt aaaatgggaa taataataat    43920
gatgataatg ataataataa tgatcttacc agatttttt gagtgttaaa tgaggtaaca    43980
tatgtagtgc atctagcata gtgtctggca tttaccaaga accccgggaa cctgagcttc    44040
aactgcttct gatactattc cagatactat ttcaggatat tccaatactg tttccatata    44100
ttcaggacaa tggaccaact cctttagcca ttttatcaaa actctttaga ttctgtttca    44160
aatcggtctt tccaaagtct tcttgtgctc ctttgtagac actcttcagt cagagagagc    44220
tttttaatct cctccaattt gctgcagctg tatctgtgcc tcaaaacaac gctttctccc    44280
cattcctctt ttctctctgc ccttggaact ctgtggactt ctctcatgtt tttaacctac    44340 tccctttat cagtgcatgt catctccact tatttgtagc acccaatatt tttactacat    44400 cttgaccaa ttaagtctta cttgggttat gttttaaag taggtatctt attaggtggt    44460
ccttttaaag tatatgtcca gtctctccag ctaaattaaa acccttgagc acagagacca    44520
catgttataa tgtttaccct tttccatagc acttagcatg ttaccttgac atggcatata    44580
ctgaatgaat gcttgctatt tatgagttta gttagtgcca catctcatga agtacaggga    44640
cttaatgatt ctcaatcctg acttcatctt acagtcacct ggagaataaa gtttcctctt    44700
agctcaacaa gtcagaatct ctgagcaaaa tcctcaactt cttacctagg tgatactctt    44760
gtaagccaca ctgtgaacca ctggattcaa cagatgaagt aatataagcc actggctctt    44820
aagcctcatt gattattgcg gtgaagatgt gaagactaaa gatgctttgg gcatggcaaa    44880
gtgttctaca gatattagaa ttgttattat ggtacatttg agagtgtcat tgctttgaga    44940
aagattctct aagttttta acagccacac tgtaatggaa atatccaatt ataggtatcc    45000 aaaaccttt aaactcttta tatcaggtgt atataccctg ttcctttttg ctaacttaaa    45060
aatgttcaaa ctctgtcttc tctaggctgg caaacattca gcagcacacc ctctcaagat    45120
tgtttacttg cctttgctcc tgttgagtta caacgcttgg aagcaggaga tgggctcagc    45180
agcagccaat aggacatgat ccaggaagag cagtaaggga ctgagctgct ggtaagacag    45240
tggagacagt tgacacttgt ttgtcaagta tgaatttatt cctaatgtaa tggtaatctc    45300
tctcccaaac ttcaacttca agttaccctg caccctctca aatactttc tttattgtct    45360 atgcttagga cacatggatt agattgttaa gatttgtgaa tttactaaag ttgtgtactg    45420
acttatgtat agctgtattt ttctggagaa agatagattt ttatcaattc tcaatgtcta    45480
tggagttttt aaaagaggt aaggattatt caaatgtaac tataaacata agaaaatgtg    45540
atatctataa ccagttgtta gagtatttat cgcctccatt ttgcttcact tgtagccact    45600
```

```
tcgtctcaat cttgttaagg accaaataaa tggtatttgt ggttacttgc tgatctgaaa    45660
agtgagtacc tcctgcacct ggctagtcag tcttgtgaca atttggtgcc atagaactag    45720
cagagaacta aattatggaa tggcagatct caggagcagc tatgtgattt tacatacggt    45780
ttgtttttaa tggatagaga cagagtctgg ctatgttgcc caggctgctc tgaaactcct    45840
gggttcaagc catcatcctg ccttagcctc ttaaggagct gggattacag gtgcatgccc    45900
ccaggcccag ttcatatgat tttctgaaaa tacaaaagaa agagggagat acaaaatact    45960
tttttaatca tgttcttata attatcttaa taaaaatcaa tttgctctga atgccatgac    46020
ctgctgagtg tcccaaccta agggttgtca gaccattttc tcatatatgc atgtatagaa    46080
gtagggaact aatatatttt tgtctaaaat gtttaagatg aagatgagaa tgaattctac    46140
aatatataat tttgcctgaa ctatataaga cagttaaaat tatagagaca ttgcaggaga    46200
gactctggat tagatagaaa aaaggaagaa ttaggctttt ttttgtcta taatccttt    46260 agtaggtaat tcagcttcag tttcactaaa tcttgtttat gcattcagca taacaaatct    46320
tctaataagc ctgtatagct ctaatctctg ccttactgca gacacctgag gatataagta    46380
tccactctgc cacttgatac ttctcagaga ctgttctggt gctgagaaat cctttccagt    46440
gtgtcctcag ttgaactccc atgattcctg gatgttgcca ttttcaagac acagggcaag    46500
cgcatctgtc tagattacct ctctaccttg ggaattttaa gtcactctgt gagggaaaga    46560
gaactcagta tagtagtaac tctcagaatg aaaattttcc ccttgcatgt taatatttt    46620 agagtaatca ttgtcactga aaatagactt cctctttccc ctctcatgct ggaaaatctt    46680
aggtaattat gaataaagca ttctttactt ttcccctcct cccttgatga ttgctttacc    46740
tcactctgtg agaactgtga ctactcattc tgctcttgtc ttttacatga gaactgagag    46800 cgcatttta agatggaatt ttcctcctta atgaagtcat aacattagtc agaagatttt    46860
ctcttcttga acgttaagcc tgggtaagga ataaagtgca gaagtttatg gaaaattata    46920
agataactta aaaaaaaaac gaagacaaca aattaaaata ttagccattg agggaaaagg    46980
ttttacaggt agctctctga ggagttcttc cctcatatct cctcaaaaat cttgttttgc    47040
atttaatttt ttacagttgg ataagctcag cccttgacat attttcaata gcaaataagc    47100
ctagagttta tttttagtac atttattagg aatgtgttct tgggaaaatt attaacctc    47160 tgtaagcct gctttaaatg gcaaagaaga agtaggtaa taatagataa taacaggatt     47220
attttatgca ttacctgtac attgcccaac atatagtaag ttctcaattt tatattggta    47280
tttgttttat tattaaccac ttttattaat gttgctttta gttttgaaa tatgaattca    47340 ttcaaaaata tttcttgagc acctgccaaa taccaggcac tcttctagga actagagtgg   47400
cattaatgag taagaggcaa aaatctcttc ccttgttgag cttagaatcc attagagtaa   47460
gagacagaca catacaaaat aaaatgtata atatagtaaa taccaagaag tgctaagttt    47520
taaaaatgta aagcagaaaa aggaaattga gtggcagggt taggtagtaa ttgaagatat    47580
agtagtcaag taaggcagct tcaagagaag attatgtctt aaataaaaat ctgataaaga    47640
tataaaaaca agccatgaag ttatctgaag gaattgcagg tagtggagaa cagccaaaag    47700
acctggagta gtaaaaggtt ttatgcagag tgatttaaaa agaatcacag tatcttatac    47760
atcagtaaat atttacacat acacttaagt aagtgatatg gacaagaact ttggaagttg    47820
aatagcaagg tccatctgga ctataacaga ggaggcttca caaaggaagg tgacagggca    47880
tggcctggat cctgaaggac aggaagaatt gggatcgata acaaagaatg acatcccagt    47940
```

```
ggagagaagt ggaggggaaa cagcatgaaa tggagtgaaa taagaatgtt ggcctttagg      48000
gcaggaatgg gccaggcaga gggcaagtgg gaagcaggaa aaaggcgacc ttgtataaag      48060
ttcatgttgg caaatagaga gaagatggga aagcagggta aggccaaatt tagtaaaatc      48120
ctaaagtcaa gctaaagatt attgcatgct atcctgaaaa tattggggaa taattagagc      48180
agatgagtag aaaggtgaat tcttgtattt agctatatca ttattttac aaatttaaac       48240 aaataaggaa atggaggcag tagttggagt aatttaggag ataaattgaa aatggatttt      48300
gttaagagag aagggaagat agattttata tattttaagg aaaaatcatg aggatttatt      48360
tgctgactgc acgtaagaga taaagagag gagtcaaaga tttctctaaa attttcaaaa       48420
tgattaatta cgtgttggta ttaaaagaaa tagggaagtt gggacatatg agtttgaatt      48480
cagcatgagt cagttaagac aatcagatgc agatattctt aaggcaacta aagttcattt      48540
gatatttgtc atataggctg aattaagttt ctaagagctg ttttactat gcattaaatc       48600 cgtgtaatac taacatagta caaagttgt ttgctatcca aattttgtat ttttataata      48660
agttggagag acagagaatc aaaaaattat tgatttggaa ccattagaca tcagctagtc      48720
caattagttc attttgtgga aggaaaaagg atcccagag atgttacatg actttatagc       48780
catgcctcta gctagtatct aacttggtct agcccaggtc tccatactga gactctcctc      48840
ctgctaataa aaaaataata aaaaagtatt agtggtttgt attttgctgg cttgcttgtg      48900
gagaatagga ttagaaggtt tgacttgcct gttagcactc tcttgtagcc attttctaa      48960 ttaacataca cattttaccc tttctcatga aacagatcta acttgtttag aagcttcagt      49020
cttcttgatt taattaatca ctttctccca cctttagtca ttgttgaagt ttcctgattt      49080
acaatgttat cttttatct tttcagtagt ataaggagga atgatatttc tactgttgta      49140 ctattttct gtttatcttt cagaagaaaa atagcttttc ttattggccc aaaaaaccat       49200
caccctacag gaaataaatc acactctttg cttgattttc ctgatctggc tactgatttc      49260
tcttcaaatt taagccaata cttagacttt aagacttcat tgttacttcc ttacaggtca     49320
ttcttatgaa ctaaaatcca tagtcattgt tctagcaagc ctgagcagtt tattctttga      49380
gtcacaggat tataaagaa aaaatagacc ttagagatca taatacagtg ctcttcaaac      49440
tgtactcttc aattttcta ctacttatca gttgttttt attctaataa aatataatta      49500
cctagcaagt gagcagacat gtatttacag tagcttaca attctttata cacttcttta       49560
ctctctccat tacacatgcc acatggtatg atacaagtca taactcaact atgtgaaagc      49620
aaaaccactc ttatacatgg tgtcttgcat atatattaag gcccagagtg gtatcagtag      49680
tctctgtgtc ccaagagact gaattaaaca agactgttga ccttcttgtg gcatttatct      49740
gacaaccttg gcaatcccta aattcacaaa tagctgtata gcattttttg catttaatgc      49800
atatccacat atgatgtgtc ctttgatttt agaacaagta aagcatgcta aaatagactg      49860
caccttatga aagtcatttt cactattctt gtgtttcagt ttcctcatca aaaggtgaaa      49920
tatcagctgc ctctgttgat ctcaggatct tttaagtaga aatggaagag tcttagtgaa      49980
aacagtttgt attctgaaag aaaattgcaa tgtaaataca ggcactaaaa acgtttattc      50040
atctttacag atgttaatct gaccagacat ttttctcaaa atgtgaaaat agtatggatt      50100
ttcttagctc atttaatatt gaaagactag aaaaacaagt aatgatgttc tagaagaatc     50160
tatgatcata taattacagt tgtccttcag tatctgtggg agattggttc caggacccc       50220 catggatatc aaaatctgtg gatcctcaag tctcttatat aaaatagtgc agtatttgca      50280
catgatttac atatacccctc ccatatactt cgaatcatct ctcgattatt tataatacta   50340
```

```
caatgtccat gctatgtaag tagttattac actgtattgt ttagggaata gtgacaagaa   50400
aattaatctg tacatgttca ttacaaacac agcaatccat ttttttttctg agtattttga  50460 tctgtgattg attgaatcca cagatgctgg aatccatgaa tacccatggg gggctgacta  50520
taatgttgtc tatgtgcgta gcaattttgt aattctcaac caaggacacg tatagtcctt  50580
gaatcttggt aggagtcttg gggactttc ttaaaatatt ttgaccatct tctcaagatc   50640
ttgactccta cccccacttg tacacgtgca catacttgtg cacactcaca cacaataccc  50700
ttccttaagt cctgctcacc agcttgcttc ctattgcatt gagagcattc aacctgtaga  50760
ccaagaactt ctaccatatt tttccacctc taccccaaaa cacagtttag acatatccat  50820
tcttttcatt cttcagagtc atctcaccac ttccataaat tatttcctaa ttgttccctc  50880
tgcctctgtt cttttttttt tttctgatga tcagttcaaa gtacctctgt atgcccattc  50940
ttaagtgcaa atctgaccat ctatacccct tcttaatatc ctttctttta tggatacccca  51000 tttcagactt tattaaagga gtggaagctt cccctcccc acctcaccac ttgaagtttt  51060
tgcaattaga atggagttta tttggttaat gcaaaaatag atgtgatgta gaattcttgg  51120
ggacacctac ttatcccctt ttcagagtgg ccctgaatag ctctgtgaac ccaggaatct  51180
gaagaactca gtacagaaaa ccatcagcct acagaaagta gatcaaactc tatgcttgat  51240
attcctgatc tggctcctgg ttactcttca aattcctcct tactatattg tcccttcaga  51300
tttgtaaatc tttaccgtga catcgtattt tacacactga acctttgtac cgctgttcct  51360
ctcctgatga acttcccttt tctcttaact acacagctca gatttctcat aagggaagct  51420
tcatatttgt tgtggcactg ttgttcctca aacatcctac ttactgtagt catttgttta  51480
tgcttgtctc ctttgcagat tctgaaattc ctagggcaaa ggctgcatct tgtcttctta  51540
ttactaatat tttacacagt atctggttac atagtaggca ttcaatcata caatttaaaa  51600
gaagaggttg actttgtgat cttttttcata tgtttttattt ccctctcccc ctactggcaa  51660
cttcttccta cttcttaaaa tagatacagc acttgcccac taagtggagg gaagaggtgt  51720
gggagtcgag tagttggaac ttcaagtgtc aaaacatgat aatctcattt gcaaagttac  51780
attatatcgg agcttgaacc tcagagatac ttaattataa gcaacacttg tggaacattt  51840
gatacctaca ttttttttcac taaagtatcc tatcaaaatt aaatgtgttg cagttgagat  51900
ttgtgaggtt ttagctattt agagacttta gggatatgtt tagtgttcta attctaatag  51960
tattgatgaa tataaatgtt tcactgtaga aagagaagtt tgagagctgt tgtgaatgat  52020
atttgatgtc tattaggtga taatttctga tgactaaaca tgctcaagac cttagtgaga  52080
aatacatgaa tacagaaaat attttgaaaa ttatgagaag tttatcattg attatagatt  52140
ttcttatcca gcagttttttg gttgtgttct gttttttcact gtcagagaag cagaaagtgg  52200
tcagtggact ttagaatgta ggctcttgta ggaggccata tgtttgagag tgctgtccag  52260
gtgctttgtg atgtggctga gaatggatgc aggcttgcag ggaaaaacta atactgtaga  52320
tctctagaga gcatttagg aaagacttct aagctttagg ttccctgacc aaagagtaaa   52380
aagtgattct taatatccat agctatagag gaaagtaaat acacttccca catcaaatgt  52440
agaattaaat atttaggcat ttcaagtgta tttcatttag aacaaaataa atcatatat   52500 tcactaatga aatataaaac cagatggtct ctgaaaggtt tttcccttta ctcactttca  52560
gagtaaggca aggaagagta gttttgtttt taatttata ttttaattgt ccctttctgt   52620
ttttccaaaa gttttatttt ttgaaagtga gtcacctttt agacatttga aaaattagaa  52680
```

-continued

```
ttactatgat gtttatttta ttagtaagtc ttcctagagt agcaacgtag aaaagcatct    52740
ctgaatgcct acatagtaag tatttaataa atgtttttg ggccaggtga ggtagctcac    52800
tcctgtaatc ccagcaattt gggaggccga ggcgggtgga tcacctgagg tcaagagttt    52860
gagaccagcc tgaccagtat ggtgaaaccc catctctact aaaaatgcaa aattagctgg    52920
gggtggtggt gcatgcctat aataccagct actcgggagg ctgaggcagg ggaatcgctt    52980
gaactcagga ggtggaggtt gcagtgagcc gagatcgtgc cgttgcactc cagcctgagc    53040
aacaagagtg aaactctgtc tcaataaata aataaataaa taaatacat aaataaatgc    53100 tttttgattt aacgaaggtg tcattgtcct atgaaaagga aaactatcaa aatatatttt    53160
ttaaaactta gcttttgata atgatatgga agatatttct cttaattaac ctaagtcaga    53220
aactaaaata tgttataaaa tgctaacatc aaatatttga gaccagttaa aggagacaga    53280
aggaagttat ggagaaagaa gcagtagcca gaaaataagg gcaagaaaat gttttctaaa    53340
tttatgagaa tcagaatgtt tacaaaattg ctattattat catctggaaa aaatatgcct    53400
tgtaggctga aaaaatgaac attccctttc cataccatgc aggaaccttc tttactgcat    53460
tcctaagagg actagtctag cacctaattg gatacttgtg gtaatatttg gaactcact    53520 gatctggtac atcagtgtgg gagtcgagta gtcagaactt caagtgtcaa aacatgatag    53580
tctcatttgc gaagttacac tatattagag cttgaacctc agagatactt aattataatt    53640
aacacttgca gaacatttga tacttacatt ttttttttcac taaagtgtcc taccaaaatt    53700
aaatgtgttg cagttgagag ttgtgaggtt ttagctattt ggaaactta gggatatgtt    53760 tagtgttcta attccaatag tattgatgaa cataaatgtt ttactgtaga aagagaagtt    53820
tgagagcaag ttgagcaaga atctgtcact ctaggtcttc tactctttat taaagaatgt    53880
tggattcatt tataacttac tggtcccttta aatattaaag tttggtgttt ggtatcttaa    53940
acatgattac atccttatag ggctctcttc taattgcctg gatactgcac atctattaat    54000
acagtctcaa agcacacttg ctttttttgat agtaagagcg tacgatttaa tcacattgaa    54060
gttagtccgc aaaggttttt gtctttttt caggcaagca gctgatgaat gaatctctac    54120
tatccttcac tttgtgactg tgattttcta aataaatgtt ggagatttta acttacaatt    54180
tattaatttc catcttgttt cttcaagtcc ctcctttaag gaaatttatg gaaatctttt    54240
tccataccat caagtggctt attctttttt aactttttc cttaagttca ggagtacacg    54300
tgcaggtttg ttgcataggc aaccttgggt catgggagtt tgttgtacag gttatttcat    54360
cacccaggta ttaagcctag tacccattag ttatttttcc tgatcctctc cctcctccca    54420
ccctccaccc tctgataggc cccggtgtgt gttgttcccc tctgtgtcca tatgtcctca    54480
tcatttagct cccacttata agtgagaaca tgcagtattt ggttttctgt tcctatgtta    54540
gtttgctatg gataatggcc tccagctcca tccatgtcca tgcaaaaaac atgatcttat    54600
tctcttatat ggctgcatgt tattccatgg tgtatatata acacagtttt ttttatccca    54660
gtctattatt ggtgggcatt taggttgatt ccatgtcttt gctattgtga ataggactgc    54720
agtgaaaata tgtgtgcatg tgtctttata atagaataat ttttttttcc tttggtatat    54780
acccagtagt ggggttgctg ggttgaatag tatttctgtc ttgaggtctt tgaggaatcg    54840
ctacactgtc ttccacaatg gttgaactaa tttacattcc caccaatagc atataagtgt    54900
tcctttttct ccgcaacctc actaacgtgt tattttttga cttttaata atagccgtcc    54960 tgactggtgt gagatggtat ctcattgtgg ttttgatttg catttctcta atgatcagtg    55020
atgttgagct ttatttcata tgtttgttgg ccgcatgtat gtcttctttt gtaaagtgtc    55080
```

```
tgttcatgtc ctttgcccac tttttcaatg gggatgtttg tttgtttgtt tgttttcct   55140 gtaaatttaa gatccttata gatgctggat actattgtca gatacataaa ttgcaaaatt   55200
tttctcccat tctgtaggtt gtctgttttc tctgttgata gtttattttg ctatgaagaa   55260
tgtctttagt ttaattagat cccatttgtg aattttgct atgaactgga tctgatataa   55320
gcatatgttt aatttaact cccaggtcac actgtttttt tttgtttgtt ttgttttgt   55380 ttttgttttt gttttgttt ttttggagat ggagtctcac gctgtcacca gtctggagtg   55440
tggtgataca atcttggctc attgcaacct ccacattccg ggttcaagca attcttctgc   55500
ctcagcctcc tgagtagctg ggactacagg cacacaccac catgcccagc taattttgt   55560 atttttagta aagatggggt ttcaccatgt tggccaggat ggtctctatc tcttgacttc   55620
atgatctgcc cgcctcagcc tcccaaagtg ctgggattac aggcttgagc caccacacct   55680
ggccccaggt catactttta atcaaaatga aaaaaagat tgacttcact ggagtgctta   55740
tgtcttgttt tatattcaag ttttaaattt atgttcttga gattattaca tcttgagtta   55800
cttgataata ccacggttga aatccatgtt gttgaatcct tcaacccctt gaggactgag   55860
aattcccttt aattatctgt ctgaatcatt aaatacttgt aaatcaagag ttcaatttag   55920
aaatgttata cttgatacat tttttaaagc tggataaatt aacctattaa acaaaattat   55980
ctcttcttca aaaaaaggc atcacttccc ccacaaatgt gtaatttagg aattgttttc   56040
tattggagtg gttcacgctt atatatttta gttgctctaa tgcaaggtgt ttcctaaaaa   56100
gtttaaggaa agtataactt tattttcatg tatgatagta aataatacaa taggggggtgc   56160 atttgtgcta tgcttgtttt tgttcccatt tcagtgctca attactgtag cttctaataa   56220
ataaaattat cagttgctaa catttaaatc aaacagttcc acaagtggaa gtattgctta   56280
tttgtgagag ttgtgttttt ttaaacttaa ccttactgag gggttttaag gactgctaat   56340
tatagattgt actaagcaaa gtataaagta atagaaggtt accaagttga ggctagaatt   56400
caattagtgc caatacagtt aaaatggtat cattaacaga acatcttcat ccaggacctt   56460 ttttttttt ttttttttt ttttcagaca gggtttcact cctgttgccc agactgcggt   56520
gcagtggcct gattgaggct cactgcagcc tcaacttccc aggctcaggt gatcctccca   56580
cctcagcttc cagagtagct gagaccacag gggcatgcca ccacccctgg ctaattttt   56640 gtattttttg tagagacagg gttttgccat gttgcccagg ctgttcgcaa actcctggcc   56700
tcaagcaatc cacctgcctc ggcttcccaa agtgctggaa ttatgggaat gagctgccac   56760
acccagcccc tccggaatct ttagattacc aacttctgtc ttccaggttt ttatgtcctt   56820
ggaaatttat gcatatttt agaggtaaga cccatcctca tcttcttcct aatccttgac   56880
atattgtgaa cacagatata tatacaatta gtagttccc tgagttacaa atatacttaa   56940
atatacttta acttattata gaaggcttac aaaaactgtg gataaataac atatatttat   57000
cttagttaat gaataactga tgctgaaaat aatgtgaatg tcaaattagt tctcttttt   57060 tctagccctc acctttgaaa agcctgagcc tctgagatgt gagatgactg ctgtaaagtg   57120
aagcagcgaa tttctagagg ctgggttcac gcttcaggtc ctctaaatcc taggtcgctt   57180
cccactacta catactaccc taaaaaatct gtaattcgca aatttatttt ttgatctttt   57240
tcataactta ttaaatttt attgaacaaa tacaggaaac agttttaaat tactcattgc   57300
tcttgaatac attggtgatt ttttttcttc tctgaaattc tgttttcctt aaaggcagtc   57360
attttttggt ctcttctaaa tgacacttag tattttagt aacatcataa cttcagtggc   57420
```

```
cacagtgagc cctcattttg caacatatgc ctactttttca tatctggctt gccttttatt    57480
atttataatt taatgaaaag aaagtaccac tctttccata gttttgtaat agaattgctg    57540
tcaacaaagt agtggatgca ctatgttata aagatttcat tgtgaaaaca tgaaatggct    57600
gttaactata catcaggcaa aataaaaaca ggaaatataa acatttcctg aacagggca    57660 gagtatgagt aataaggtat caaatataat tggatacctg accaaatatt tttaaatgtc    57720
ttaagaaatg tcactggaaa gactggagta cttggatttg tctcttattc ttattttgat    57780
tcctaacact gtgcttggca catggtaggt aattaataaa tgtgtgatgg atgaataatg    57840
attgtcattc aattagtgac taagagagtt ggaaagggct atcaatttca aattggttcc    57900
tttaagacat ttttacgtaa gatttgggag aaaagtaaaa gagcaccata tgattatgct    57960
ttactaagag ctgcttccat tcctacattg accatgtgga ctcatatttg cctatataa    58020 ttacattaga ataaacaaag caccaaaagt tggaaaagga agtagtagta ggagagggtt    58080
ttaagctatg tatttactgg gaaaaaaagt catgttttct ttttttaaaaa tgttctaaac    58140 agtactgtaa tcacttggga attgaatgtg ctttgtgtca gacaaaggtc tttgtataca    58200
atacattaca ttttgtatac caatacatta cattacacag aagggagtgc ctggcttttgt    58260 atacaataca ttcattttg tataccaata cattacatta cacagaaggg agtgcctggc    58320
tttgtataca atacattacg ttttgtatac caatacatta cattacacag aagggagtgc    58380
ctggctttgg gaaacacatc tacctaaact cttaacatag cacaatgctg ccatacggta    58440
ggtaatacca agacaaatca gggccgttat taacaacctt gaggaaatgt cttgggaaat    58500
atttaaataa ttttttgttta attataataa ggaatctaca gcctctgtga agtcatccca    58560
aactcttcga ggcaaattta gtctcctccc accctgttt tttaatgttt ctaaaggatg    58620
ttatgtataa tctattagaa aactggccaa gtgcagtggc tcatgcctgt aatcgcagca    58680
ctttgggagg ccaaggcggg tagattacct gaggtcagga gtttgagacc agcctagcca    58740
atatggcgaa accctctcta ctaaaaatac aaaaattagc caggcgtagt ggcaagtgcc    58800
tgtaatccca gctactcagg aggctgaggc aggagaatct cttgaacccg ggaggcgagg    58860
ttgcagtgag ttgagttcgc gtcactgcat tccagcctgg gcgacggagt gagactccgt    58920
ctcaaaaaac aaaaacaaac caaaaaaaaa aaaatatat acacacacac acacacacac    58980
acacacacac acatacat acatacatta gaaaactaat tacattgttt tcttaaaatg    59040
ttttaagcat ctctcttcct caaggacaag aatcttgaat ccttagtgca tatgaggtac    59100
ttaatagata ttttaaatgaa tagtgagcta ctattgccta aaaatattag acatcatgta    59160
atatcaggcc tacagttgat agaaaaagta ttctcaacta agaataattt accaatggag    59220
aaaactgtta gtttttccctt ctttttctttt gctttataaa atttaaatga cattaagagt    59280
tacgtttctt ggaaaattga aagaatatc tgtggcacaa tgggctctgg gtataattgc    59340
aggataattt gaaaagttta aagaatattt tcaataggta taagtttatt taggctctgt    59400
gtctcctctt gagatgactt tagcagtata tatttccctg aacaccatg cactctaggt    59460 tttctaattt attggtttaa aatacatggc attttactac gtaaatattc tctgtatctg    59520
taggtacagc acctctgtgt acactaagtt agtgtatgta ttttttttaaa attgccttag    59580 ttttgctatt cactagatta ttttccaagg aacctactct tagatttatt aagcctacta    59640
tatatatttt gttattaact aattctctta ttttaaaaaa ttacttttcc tttctttgct    59700
taaatttgct ttgttttcct aaattagtga tttggaatac ttaattgttt ttatttttgtt    59760 ttgttttgtc aataaaagag ttttaagact ctagttatac tatagctata gccaatgcat    59820
```

```
tttgagaggt gcttacatat tacaattatt ttcagaaatt ccttatttca aagctttgct    59880
ttctttgaac aaagagttat ttaggaaaag aaaggaataa aaatctcaac ttattctcca    59940
cttgactagc tttattattt gcagtattct gttttttact tgttctaata cttctttata    60000
ttttgttgtg gaattatgtc acctaacaat attttcctta acttcttaat tttagcctgt    60060
tttccaagtt aatcatttat ctgttgtttc aatgaatacc taagaaaatt ttctttgtca    60120
ggataaggca catgaggtct aagatttatt tctagaacag taagcaaatc atttctgaaa    60180
gtgtgttctt ctactattaa gtaacatgtt tattttttgtc ttttagttga agtcccccccc    60240 aacccaatag gtactattct gatttgttct cctattcaca cattcttgaa ggagagctga    60300
tttatctgta cccacaaaat tataatataa ttttctcaga gtattcaaaa cattgtcttt    60360
tttatttttc tttttttttga gttttttcact cttgttgcct aggctggagt gcaatggcag    60420
gatctcagct cactgcaacc tccgcctccc ggtttcaaga gattctcctg cctcagcctc    60480
ccgagtagct gggattatag gcatgcacca ccactcctgg ctaatttttt tctattttta    60540
gtagagacgg agtttctcca tgttggtcag gccggtctca actcccaac ctcaggtgat    60600 ccacctgctt cagcctccta aagtgctagg attacaggcg tgagccacca cacccagccg    60660
aaaacattat cttaatggag catttagaac gttatcactg acaaactttt ttctattgaa    60720
aatactgctt aaaagatcag gtcatgccca ccccacaacc cacacccttt gtatttctct    60780
tttacttgtc ttggcctcta gttcagattt atagtttggt aatgtctgat tttctttgtt    60840
agtgcttcag cccatctggt tggggaacag ctctatccca ctgggacctc tcccttttcct    60900 catgagtgac gccagggtcc tgctgcccat aagcattctg tttgctgagt ttgtatatat    60960 ttccttttccc cagcttcgct gccttttggct gctttgtgat taagtaagac atacccatgt    61020
ttcctaaagc ctccttcgcc tttagtcctt gatgctgggg acctttggt tgggaagaca    61080 gcttccttat gtcagggtga gcctgctaca caggtatgta actcagacag tgacctactg    61140 ttgagttttct gtttagtgtt tctttgtctc cctcaaatgg tacaaacgtg gagggcttca    61200
actgcagtct acctttgtcc tgttagtttt gtctatcaca gcccatgccc tccaaataag    61260
agatgatgga gcagtctgct tattttctgt agcactccac aactgacttt aaaagaggga    61320
ctgggattgg gctcttagtg atgactttta atgtggattc atctgcattt tctctagaaa    61380
ttctttaaac tctctgcctc tcagctggca ctattccatg gtattttagt gctaatgggg    61440 gatctttttct aatttttgtt tttctttgac tgtttaaatc atttactgga aagagggctt    61500
agatatctgc tcatatgctc ctgctagtct acaagtcctc cagcctgatt tgttcatga    61560 acatgatgga aataagcttc ttaaatgcct ttaatattgg atactgcttt caaggaaatt    61620
taaaatagca agcaggcttt caagaagaga gaataaatta tcagccagtc tcgcaagaac    61680
aaaaataagc caagtcatat aaaacaagtt tggagtaaac ttgtttttac atttcaaatt    61740
cgagttgaac tcttcaagtg aagcttcaga gatataaaaa actttaactg ataaagattc    61800
caaacattaa tatatggaaa tgtatgagct cactgaaaat tttacataaa ttttactaga    61860
agaggtgact gaccagttgc ttttataaga ttctcaaaaa gatctcaaat cttagggact    61920
aatattgtaa gtatacgggg aaattaagac aaagatttac tatcttgtga gttttttagtt    61980 tggataatga acttaatttc acaagaaatt gctttagcac aaacatgaaa accttaagca    62040
tgagaactct cctttttgaag tacaaaggga gactaaagtg aataactcaa actggaaatg    62100
tagaaaattg aatttgctat gatttgaagt cctttcagaa tagccaacag attttaaaca    62160
```

```
agagttttat tgcatagttt ctttgggata tacattgaag gagaaaggag gagggagttt   62220
taaaagacaa gtggaaagcc ctttctgctt gttttggcta tggcttccat ttcagtgtct   62280
gtatttaagg gatcataaaa ggaactggaa agactggtca caatggcagc tctgtacctg   62340
tatgatttcg gatgtgaaaa gagtttagcg atttccttgt taacctatac tgctgtggaa   62400
gtcattcatt atgcagttag gcattagcag aacaaataaa gttcacagct ctaggaacca   62460
aatttaactt tatcactctt ctgatttaga atattttcat atgctttcat atgtcctaca   62520
gacgataaga agatagaatc aatacttggt gattgatagg ttattttta aaagggaaga   62580 aagaattaaa catccatggt ttcttcttaa gtaactgggg ggatgatagt atccctcaca   62640
ccaatgggga gtatagatga caggtttgga gtgaaagaca gtgaattcca ttttggataa   62700
gttgaatttg aagtgcctat gggacataca ggtacagatg actaggagac aattgaaaat   62760
ccaaattgtg aactctgctg aagattagaa gtacagatct gagattaaat tgctacttga   62820
gttcatggga ataaaatagg tcattctgca aatggttatc tcaatatctt cctggccatc   62880
tcttgggtca ccttgccaac ttttcattct ctttacaatc tctaaattct catgttttta   62940
aggctctcat cttaggccaa cttatccttg gtcaccttgc taacttttca ttctctttac   63000
agtctctaaa tttgtgcttt taaggcccca ttctcaagct ggcttctctg ttttggtggg   63060
aactggtagc aaacattcat ttgtaaacaa cccaaatggc tagcattgag caggactccc   63120
caacatactc ctctgaatta cattttgagt tatctgaagg atcaatatct caaactagga   63180
aactgtagct ttctcattta ttttcatcat ctaattattt ttcttgcctt taagtataag   63240
ggatagagac ttgattgatt tttatgtaca acaagttaaa aaatttaatt aggcgtcttt   63300
gccatttaat cagtttatac ttcttgaatc ttttccagtc atcaaaaagt tgctgagcat   63360
gcgcagcttt acttactagc ttatagcatg aagaagagta aaataggagt ggataaaggc   63420
acagtggtga gtagtcagtg tttccaatta atctcaaagt ttaggattaa tttagcgtga   63480
attctgttct tttgtgtctt cctgctttt gacgtggtaa cctgccataa caaaaggaaa   63540
cagcaggaaa cttggtacca attaaaacag tcttcttccc ccaaagaacg aactgtcagc   63600
aaacaatctc aaattcaaag tgataagtgt tttagagtga acaaggata aagagacaag   63660 gctattaaat tttaacatct gctggaacac aaagcgcatg ccagtagaat taagtttggc   63720
atttaataag atacaatttg cacatcagaa atgaaataga tgcctcaagg catggtatat   63780
atatatatat atatatatat atatatatat atatatatat atatgtttga gcgaggggca   63840
cttctagcaa aactgaatac actggtataa atgtctgcgt gaaaattttt ttatccattc   63900 actttggtg tgtattccag ctgtgagtta ttcaaccagg ctcactaagt ttgagtctga   63960
ttaataacgt ttaaggtcac atctgattaa cagtatttga agtttgaatt tgttctaaga   64020
tgactcaagc gcaataacat tttctatatc aaaatgaatt tccatccaaa tagggaggaa   64080
atctgaaatt tcagttccag tgttgactga gatgctctgg atgagcctgg actcagagct   64140
caccaacttt ggatctttat gttaagtagt cagtggggtt gacttctaga ctagagatca   64200
aaatgttcta cacctcttga tataggtcag tggctgatgt aatgtgcttc caacaacttt   64260
cttttaacta aaacagtaca tataccaagt tggtttgtca caatgggaac aaaacagaaa   64320
tctgacaaca gatttctcta attttttgtg tgtatgtttc tgaatgggct aaaatacata   64380
attttactct tccttggtga agatgctttt ataagaggac gtgtttaaga aaattaagaa   64440
atgttgtagg tagccatgaa agaattattt taaacagaat tagtatagag gtgtgaagat   64500
ctactgaagg gtgataagta agtgtggaag agatggtgtt cagcattggg cttcagtatg   64560
```

```
aataggtaga agatgagcaa ggcttagaga caagaagttc attcaatagg ctgttgcggt   64620
tatccagcaa tgagatggtg acagcatgag ccatggtagt aaaagtaagg acatggataa   64680
tttgtgggtt ctacagacaa taagaacata gaaccgatag gttatttttt aaacgggaag   64740
aaagaattaa acatccatgg tttcttctta agtaactgcg tggatgatag taccccctcac  64800 actgatgggg aatgtagatg acaggtttgg agtgaaagaa tgaattccat tttggataag   64860
tagagtttga agtgcctatg ggacatacag gtacagatga ctaggagacg attgaaaatc   64920
caaattgtga actctgctga aggttagaag tatagatctg agattgaatt gctacttgag   64980
ttcatgggaa taaaataggt cattcagtaa attgttatct caatatcttc ctggccatct   65040
cttgggtcac cttgttgact tttcattctc tttacaatgt caaaattctg gtgttttaa    65100 ggccccaatc tcaggctggc ttctccaact gtactcttac ttgggatgat cttatctagt   65160 catgggcat  taaataccat tggtaggtta acacagttca caattttctc cagcttagac    65220
cccttgctga tttcctgact tgtacactca actgcctgcc taatataccc actttaatga   65280
taatgtacat ctcaaactga gcttattcga aatagaagcc ttaatttttc tgtcagtcat   65340
attgttccca tttacccatc ctaacaaata gcaccatcat caacctttta gctcaagaca   65400
aaactctagg cattatcttg cttcattcc  tttcatgtac tttctcacat ctaatccatt    65460
accaagttgt tctgtttctg ccttcaaaat gtgtcctaaa tttatccatt tctctgccac   65520
tgctattctc tagttcagga cattctatcc tttctcttgt attactgcgg tctctaaact   65580
tcatgtatct atgtttata  cttttaattc attgtctata cagctaccag agtgatcttt    65640 taaggtcta  aatcagttca tgtcactgct ttatatataa tgcacctatg gcttcccact    65700
ggatttaaat aataatctta acactttact cctccatggc ctttacatac ttctagccgc   65760
acctcaaaac actcctcttg ttcactgaga actaactaga ccagtttctc ttctcctcag   65820
ctatatcatg ctaatttatg cttcagtgcc ttttgtactt tgttccctc  tagctgaatc    65880 attcttccag gtcattctat cattggcttt ttcattcagt tcagatagat atcagcaaat   65940
caagagagtc tttccttacc tgctctatct aaatagtcct gttttagtcc tcttatctc    66000 atcactcaga tttatttccc tcatagcact catcagtctg aaattgtttg tttatttggc   66060
tacttgtttg tctagataaa cttcactggt gaaggaatcc agactatctt gttcatccct   66120
acatccctag aacctagaac aatatgttaa agataaataa ataaatagat gaaagaatgt   66180
tgaagagaag agggtccagt ccagccccct gaggtgacca gcatttaggg aataagccga   66240
ggcagaggag ggccattaag aaggagcaat gagagataga ggaaaactaa gaacaaggtg   66300
tccctaaagt gagagtgtcc taacacaggt ctaaatgaaa ggatagttca gaagagggca   66360
ctgcagctgg ctgaaagaga acaagaaagg ctgtaaggtg gaggtgaatt tttaattgag   66420
ccgtgaaaga tagggaaatt ctgtatgaag gagtaaatgg aggcatagag gcatagaggc   66480
agaagatgca tgcctgtttg gggaatagtc atcccatttg tctttcacat atctcattta   66540
atacttctca tttaatcctt ttagtgttaa tgttgtcact agattaaaaa acaaaggctc   66600
catcaggatc acacagtaaa cagaagaata tggatttaaa tggagatcta tctgactgca   66660
aagactactt actgtaactt aagtcattga gattccttat ggccacctca tattcaccct   66720
gcatataaca gtatgccaat gtaggaatga ggcgtgaata agcagggtaa caatagaaac   66780
atattctcac cttgattatt cctttggtag cttcaaggga aattgagttt gaggataaag   66840
taactcttcc catgtcagca ctttatctgt cctgaaacat gagaaattcc aaatgttcaa   66900
```

```
gccatgcagt ttttatctag tcagatggtt gagaagtcca ggttacccat agttgtaatg   66960
aatacctcct ctttatcttc ttaatgttct gctttgccaa atgatctata aagattactc   67020
agtgtacctt tcagattgag gtccagcaga ctttcagaac actacattta attacagaaa   67080
cccaactaat aaaataataa gctcatgtta gtttcaggtg ttgatttgtt tttaatgtag   67140
tcaataatat ttacatataa tgactggcaa cttaacagag ttataataga ttattcacct   67200
gtatttgcct ttatttgtgg gtatacacac atatatacat gccttaaact agagtaaaat   67260
catttatgca tactaaatca aatttgagag tcccaaaatt ttcaaattgt gtatggctgg   67320
tctatatttt ctaggactgt cctttctggt ttaaatgaaa ttaaaaattg aattaatgat   67380
attagtctct tttaattttc tattttttc atgattaaaa aatattaatt tccagccagg   67440
tgcggtagct cacgcctgta atcccagcac tttgggaggc tgaggcgggt ggatcacctg   67500
aagtcaggag ttcaaaacca gcctggccaa catggtgaaa ccctgtctct actaaaaata   67560
caaaaactag ccaggcatgg tggcacgtgc ctgtagtccc agatacttgg atggctgagg   67620
caggagaatc acttgaaccc aggaggcgga ggttgcagtg agctgagatt gtgccactgc   67680
actctagcct ggtcgacaga gtgagaatct gtctcagagg aaaaaaaaaa attaattttc   67740
cccattcccc cacccaccca ccaaaagact ccattggagt tttattttac aaatgcatct   67800
gctcatctac ttcttttaa gtgcataaac tagttttaca agcttgagtt taaatcttaa   67860
ctcctcaatt cttttctga catagaaata tacaggtgca ttatgaaata gctaatagtg   67920
actattttct agggctgtaa ctcaatattt ataagcataa tgatataacc tgctgaagtt   67980
tgacacgtca gtatagttct tttgttattc taagtcataa aggcagaatt tggaaaaatt   68040
cacagctttt caaatatgca gaagaggaaa aattgagagg aagcatacta aaatttcttt   68100
agccaatttt aatcaaattg agtttgaaac ttacaggatt atgcttcaaa gcttgtaatg   68160
atcgtcaaaa gtagccttat tcaaaatgac acactaattt ctaccacatc tgtattcttc   68220
tcattgtaag atgttacata tacctatgct tgaccaaatg gacttcctgc tattttaaga   68280 tattttctg tgttttaagt cttctacaa attttctcaa gcatttccct ttacctagga   68340
tgttcttctt tcactgcaag tgaagacatt ctaaaaattc ctaaagcaca ctaccaaaag   68400
cccttcattt ggatgaccca ccttcctatg agtctccata gttgcatgtc tgatggcatt   68460 tatttaact ctatgatctg cttctaaatt agataaaagc tctcagagag aactatgacc   68520
aattgtcatt ctgtttccca tggcacctag tacagtactc tgctcacagg ctcaataagt   68580
aatgagttga gctacgtttt tttaaggcag agtctccctc tgtcgcccag ggtggagtac   68640
agtggtgcaa tctctgctca ctgcaacctc tgctgctggg ttcaagtgat tctcctgtct   68700
cagactcccg agtagctggg actataccac catgccacca tgcctggcta acttttagta   68760
gaaacaaggt ttcaccatgt tggccaggct ggtctccaac tcctggcctc aagtgatcca   68820
cctgccttgg cctcataaag tgctaggaca aaagtttgcc attgtcatgt tacgatatat   68880 attggtttt gtccatggtt tctggttcat agctccaata tccctttta cagtcttttg   68940 ttagaatgtg gggtgtgttg gacctcgggg caggccttag aaaacagaat ctctcctgcc   69000
ttcctttcac ttgtccccg agggagattt ttttttttt tttttttttt gagacaagac   69060
ttccctgtgt cacccaggct ggagtgcagt ggtgtgatca tagctcaccg cagcctcagc   69120
ctcctaggtt caagcaatcc tcccatctca gcctcccaag tacctgggac tacaggcaca   69180
tgccaccaca cctggcattt tttttttttt tttttttttt gtagagaggt ttcgccatgt   69240
tgcccagtct ggcctccagc tcctgggctc aagtgatcca cccaccttgg ctcaaaccac   69300
```

```
cacacccaac cctgagggag attctaatct tccccaccct tctgattttg agtcttaaaa   69360
ccccagagaa ggtcccaccc tttgcactgg ggaaaggaat gctgatgatc atgaagcctc   69420
cataaaaact caggaggatt gagtctgggg agcttctgga tagctgaacc agtggaggtt   69480
cctggaaggt ggctcatcca gggaggactt agaagctccg tgcactttcc ttatacttca   69540
ccctaagcat ctcttcatct gtatcctttg ataaaccagc aaatataagt aagtgtttct   69600
tgagttatgt gagctgcttg accaaacgta ttgaacccaa agagggtgtt gtgggaaccc   69660
caactcgaag ctggttggtc agaagttctg gaggcctgga tttgtgactt gtgtctgtgg   69720
caggagcatc ttgggaactg agcgtttaat ctacggggtc tgacactgtc tccgggaatt   69780
aaattggagg acacccagct agtgtctgct gcttgttatt ggggagaaac cctcacacat   69840
ttggtcacaa gagagaagtt ttctgttttg aatattgttg tgatgtgaga gcagaggaaa   69900
aatgcatttt ggagaggttt tttcctacac agccataggc agtgataaga atatgatgct   69960
tttttccaga aaatgctaca tgagaccttt ttataaaatc taattttctt caactgagta   70020
gcatttaaac taaaagaat aggttatttc agtgtctctc tgtaataaca tcttacaatc   70080
acttgtcaga ccatgaaata atgttctaga aaatcagtga aagagctttt taaactttgt   70140
gacatttgac ttatatttat taccaaaaag cctgaattat tattcagcac attataattt   70200
tatttaaaat ttaaattaga gatgaaatac ttgtaaatgt ttataagatt ggtagctgtg   70260
tgggcttcca gagttagaaa tgcctctgag aaaagattta gagttttgaa agtatttga   70320 aaaaagaaac agaaggaat acaacatttt tcccagcact gcttcaataa tgcagtcttc   70380
agcatcatct caaagcaata actgcagtac agatgagatc agccagtttt tttttccccc   70440
ttatctgcag tgattttacc atctcttcat gctacatctt accacaaaga gaacattgaa   70500
acatgggaaa gagtttgctt tgatttcaac cagaatgcca actcatttct ggggttctaa   70560
accataacct tttttagcag agcagtgtag aatttttata cgataccata aatggtcggc   70620
ctgagtaaca ttttaactgt aagtcaatac ctttgaagag acatgtctga caactcagag   70680
ttctattttc tccatgtgtg actaaagtac cttttctatt aagagatcaa ccaccatttc   70740
cttctactct ttgttctccc cttaaataaa gttaattcag cttcaaaata ttttatgatc   70800
ttgattacta actgtgggtc tttagaagac aatgtaaaac atttccatgc tgtgaatatt   70860
agagctagta tacttggagt ttggctagta tttctggggg aggtagaaga ggagacatag   70920
agtacaaatg agtattttta aagccacgct gactaaaaca aaaggaatgt tttatacatg   70980
tttatttcat agtacttctt tgaaacaggt cggggggagg agagttaaaa tattgctttg   71040 aatttaatc aaagttcttt catggaattg ttggtgcttc tggtaataac agttctataa   71100
tctttgtgag ttaatctgaa atgctctttt tcttcatcgt aattcagtgc ttgtcttaac   71160
tggtggactt attttatggt attatgttta taagatggca actaaaatca gattttttat   71220
actcctaaaa gatggatacg atagagggga aaggggtaa gctacaactt ttaggttgtt   71280
ggtgatattt gaagtgttta ttgcttctga tttacattta tatattatat tcaaatataa   71340
actttaaaag taatgatttg ccacaggtta aagcagaaca tttatatgat atttcctaga   71400
tgttttcctc tacaatcctg ttttttgttct atgaaaaatg ccataaactt ggatcattca   71460
ctaattaatt tgaagctgtt ttcaaacaaa aagctaattc atctttagc ggatttagtt   71520 ataatcgtga taacagatgt atagctaagt ctgttggaca aactgttggt cacatcaatc   71580
ttaaatgcat catacagcgt gatgtgaatt tatgatattt cctaggtaat gttaaggtta   71640
```

-continued

```
tatggaaatt tctttgcagg tagttaagtc ttattttgaa ttcaaatgtt attttcaata    71700
catacgtgga agtgtatttt tgtttgtcc taaatgttta gatttttga gtttacaatt      71760 tttttgtgtg ttctttcttt gttcttgccc ctccctgcat tctctatgaa gatacatgtc   71820
agcactatgc aacactaaaa taacaatcaa ccaaattata tcctatgaac agacctttct   71880
cttcatttca aaggcataac ttggatggtc tgtttagctc atggtgaaaa aaaaaagtta   71940
tgattttgta tttgggcaaa gtacaggtga agagcgtgaa tcattagaac agcaatataa   72000
ctggaagaag atagtttagt ttttacaagt taaatttgaa gctaaagcaa aacttgcata   72060
ggtatgtgtc ctttgctctt gaaaatgaac tcagaactct acatctgagt ggttttatga   72120
atttatactc tcctagtcca caggttctca tcagtgcctc aagatctatg cacagattaa   72180
aattacataa gatatcatat actacatctg aattagggtt ttccaaagta tgctattcca   72240
tggaaatact gtttattcag ggtgctccat aaacaatgat cctgtgtttc attatgtcca   72300
ggaaatgcca cacagcacct ttccagacat cctatcatca tattaaagac tttgaggcca   72360
tgcattaaag aaagttttaa attagaaaaa aaataagttt tcttgcttga gcacagaact   72420 ttatttttc tcaggctggt tctccttttt taaaattaca cgttaatatc ccaaagaacc    72480
agtcccatag atagatatca catatgataa gaatctgttt caatggtgtt ggtgtacatg   72540
tgtgttcagg tacctacaca ttaggacaca tctctagttt attaatactg cacttataaa   72600
gagacatggt agagacatca agaagacatc atttagggt ggacaccatt gcctaggacc    72660
tgcttcttaa tgtcaaaaat tcagaaaccc aattttatct ctcccgcaga gttgactcga   72720
gtgaaggaaa ttgagttgtt ttaattaaac tcacatgaga ttgatgttta aacaaaattg   72780
taagtttatc aattaataat caagaattct gattttaat tttcaaaata ttatttatgt    72840
ccactgtcca gggtacttgc tttaagggca cccagtgatt cttgaagatg aagagtctta   72900
ggaatattta ttttctagac ctcaatgaag aaagcttttt aatcatcctg ccccatagaa   72960
gaatttatgt tcctagtgat gtgatcatat tggccaatcc agtgtttctt ttccaaggac   73020
agtactgata aggagcacca aatctacctc tttgtcctga acagatcatc tccatctatt   73080
catagtttgg ctcagaagtt ggacaaggct gcattttata tctacttctt cctcatgtcg   73140
gctatgccat gccgtttcgt tcttttagct tgtttactta tgtgtaaaat gaggtaaaaa   73200 ttacacccctt caaaccgaaa gtggtcttcg tgatgagtta tttaattgaa gccccagtag   73260
atatttatca ttgccagttt tagagaatca tagcatttta gaacacaaga tgaccttaga   73320
tgtaatcatg ttcattcccc tcgtattata aattttaaa aattgagatg tggggtggtt    73380
gtgacttgct cacaaaccca catttagaac caaaactcag cattcttgtt ctgactgtgt   73440
ctatgtcctg taggtatatg tcttgtcttc tcagttaaat aattaaagat tcttaaagat   73500
agagaccata ttttatgcaa cttctggatc ccataaatta tgtttccaga agaacctttt   73560
gtaatgaaaa aatatatata atgtctatat tatatatata gtctattact attttgataa   73620
tctaaaacat gctatataat tttaggcgat cttaacctat ttatcagagc ttttcagatc   73680
aaagaaaatt agagtaatct tcatcatgta tgggaacatt gatgtatttt tctgatgaac   73740
acatggttat atgatactct tttaaagcat ctgtattact cttctttctg atagactggt   73800 tatttttgttt atgttatgaa ataatgttgg cagcttttca ttagaactga tacatattga   73860
aatttcttaa attgatagct catggatgtg cagttggttt aatggcatct ccattattaa   73920
tctttaagaa gatcttcatc ttactctcaa aaataaccgt aatatcctac aaattaacta   73980
aaacatgatc attgctagtt gttccaaaat aggaagaata aaaatgacca gattgttatg   74040
```

```
gtaaccagtt gattaagact agatcaatag gaaaacgaat ttattcaagt ctgtacaaaa    74100
cttctccaaa acatagatgg catgcctttt gaggcaatgg tagggaacaa aatatttttg    74160
agaaggagca gattttaggg atacagtaca gtacataatt gccaaaatgc ttgtgttaca    74220
aggattcctg gtacagagtt tttaaataaa atgctaggta tgtcatgttt gtttcacatt    74280
aatattgtag agtccctgg ggatgtgaca atttagttga ccaactctaa tatagttaat     74340 ttctacctt tgatagcttt gtggggtttt gtttgtttgt ttttgtttt gccattcttg      74400 attttagggc tgaagatatg agacaatgta tcaaacagta aagaattatg cattgattaa    74460
gatcatcttg gtgaattaga tgtttattat ataactcgac tttaagactt tgttcagatc    74520
tcactatctt aatgagattt accctcatta tatagtattt aatagggcaa ccactccccg    74580
atactcttga ttcctcgtta gctgccctat tatttctttg ttttttccctt agcactcaac   74640 attttcttac cacaccacat aatttacttt cttattgtgt ttattgtttt tctcctcatt    74700
agaatatcag gtccaagaag acaggagtat ttatctcttt tgttcagtgg tgtgttactg    74760
gtgactacta gagtgcctga cacatagaat atgttcaata aatattcgtt gcatgaaaga    74820 atgaataccct tgacagatta ttttataac tctaccagtg tcattatata actcactga     74880 atgattatga gccctcctag aaattacata aagttcttat atattattag aacccatttg    74940
ttggccttat gtaatggttc tattggaaaa atcatacctc cgtatataaa aatgaaagta    75000 tttttttct acaattgccc ctcatatata ctattatagt ctccttcacc ccattcagcc     75060
attaatgtct tcttgaccag gtaacataat ttttacagca cctttgggtt attagaacaa    75120
ttttatttgt ctttcaaact cagtcctatt cattttaaaa ctcccaactc aagcctgagt    75180
cagtgttctt ctcccagcac aaacttaaac actggctcca acccttggag ttgaaagtag    75240
gggagcctca ctcctgatac ctcccctccc cctctaccgt gagcaccagt gcctaggaga    75300
ttgggcagga ctgaggaagg atgaaaagga gctcagggct ccttaagcac ctgaacaaga    75360
ctggaggact ttggatgttg ctattttcct gcctggcatt gactggctat tggacgccct    75420
ctgtgaggca ggcatccgaa tactggcttt cttgacatat atggagcgtt ctttagagag    75480
gcctacaagg gctctcactg cacagtaccc tgataggaga gatctgtcct tatttcttct    75540
atcaccatag ctacttcagc tttgcctgct gagtccaccc cacagtctct ttctgctggg    75600
gcatccttgc cctggacaga ttcttagagc atgaccaagc ctaaacaact tctgcaattt    75660
ttctaagtac acttttattt aattgaaagt ttcaagcatt ggataatata aatgtatcct    75720
agacagtgtt ccagtaagga caaccagctc acaattatcc attctaataa tgggagtcaa    75780
ctgaaataga aaatatatag ttttttaaat aatttatgag aaacaaatat ttgtgacaca    75840
gtacatttct aattatgttt atctttatta ttattattat cgtttccttc agtacacact    75900
agtttggtga gacttggaga aaggccagga ataagcccaa attcaaaaaa caattccagg    75960
attaacagat aagtggataa tagagaattg acaaagatc atgctcattt taccaataag     76020
aaactggttg gttaacttgg gttgcaaact gaaagcagat ttatactaaa ctggcaggtg    76080
tctccagatc ttaaatgcag atctctatct ctgagttaat ctgcctctca tcttcaatgg    76140
cattcctctg aattttctc cctcaaataa tctatatatt attaaatttt gtttatactg     76200 ccatttaag aaacagattt taaaacttta aacatgggaa ttaaataggc cctactgagg     76260
attatgaaaa acctgacaaa acctcctatg cacatgattt agattaggag cagtgcacac    76320
gctgtatgtg tatgtgcagc tacttgtcca attaacacct tttcagaaat ggaggaactt    76380
```

-continued

```
tctctgagga ctttgacata tttgtgtgtt cagcagtcct ttttcttttt ttttattttt      76440
tatttttta ttattatact ttaagtttta gggtacatgg gcacaatgtg caggttagtt       76500
acatatgtat acatgtgcca tgctggtgcg ctgcacccac taactcgtca tctagcatta     76560
ggtgtatctc ccaatgctat ccctcccccg tccccccacc ccacaacagt ccccagagtg     76620
tgatgttccc cttcctgtgt ccatgtgttc tcattgttca attcccacct atgagtgaga     76680
atatgcggtg tttggttttt tgttcttgtg atagtttact gagaatgatg atttccaatt    76740
tcatccatgt ccctacaaag gacatgaact catcattttt tatggctgca tagtattcca    76800
tggtgtatat gtgccacatt ttcttaatcc agtctatcat tgttggacat tagggttggt   76860
tccaagtctt tgctattgtg aatagtgccg caataaacat acgtgtgcat gtgtctttat    76920
agcagcatga tttatagtcc tttgggtata aacccagtaa tgggatggct cagtcaaatg   76980
gtatttctag ttctagatcc ctgaggaatc gccacactga cttccacaat ggttgaacta    77040
gtttacagtc ccaccaacag cgtaaaagtg ttcctatttc tccacatcct ctccagcact   77100
tgttgtgtcc tcactttta atgatcgcca ttctaactgg tgtgagatga tatctcattg     77160
tggttttgat tttcatttct ctgatggcca gtgatggtga gcattttttc atgtgtcttt    77220
tggctgcata aatgtcttct tttgagaagt gtctgttcat gtgcttcgcc cacttttga    77280
tgggattgtt tgttttttc ttgtaaattt gtttgagttc tttgtagatt ctggatatta   77340
gcccttgtc agatgagtag gttgcgaaaa ttttctgcca ttttgtgggt tgcctgttca   77400
ctctgatggt agttccttt gctgtgcaga agctctttag tttaattaga tcccatttgt    77460
caattttggc ttttgttgcc attgcttttg gtgtttaga catgaagtcc ttgcccgtgc    77520
ctatgtcgtg aatggtgttg cctaggtttt cttctagggt ttttatggtt ttaggtctaa   77580
cgtttaagtc tttaatccat cttgaattga tttttgtata aggtgtaagg aagggatcca    77640
gtttcagctt tccacatatg gctagccagt tttcccagca ccatttatta aatagggaat   77700
cctttcccca tttcttgttt ttctcaggtt tgtcaaagat cagatagttg tagatatgtg    77760
gccttatttc tgagggctct gttctgttcc attgatctat atctctgttt tggtaccagc     77820
accaggacca tgctcagcag tccttttttca agagatgtga agtacatctt cacagatttt     77880
taaatattta gatagaaagt tcttacagaa tgagaaataa aaagttagct ttgccttaaa    77940
aatattaatt caccttatat tctccatact taatccatat aggaaacatt atattccagg     78000
tctaacatgt ggcttgctta cattaatttt gctgttgaaa aatatatgtt ttggattatg    78060
tttttaaaat tttagcttta atatttaaat attaaataat gttaacttta aattaacgaa    78120
gaatagtttt taatttata agaaatgccc tataaaaaac actttcttta cctcaagagt    78180
gagacttggc aaccatacca atattacata gtaattttaa agtcaaacga aatggagaga    78240
acttaataga tacagaagat aagaatttaa actaacattt tgctcgggat tttagaacac   78300
tatacagagg gaaatttagt agacaataat gaagtccata gcattgcaca catcttgaaa    78360
taagtgtata attgacacaa gctatgtccc atgttgatag gaagaatcca aaatagtttt    78420
ggagaataat gccatctatg caggaggtgt ggccatatac atcatcttta ctcagtgttt   78480
ttcatgtcaa taaatattta attcctaaca ctctgaatta ctaatagagg tgaagcctgt    78540
cagtggaagt gacagagaga tacacagtga ttcccgtaag tttgatcctg aaacacagtg   78600
cctttagcag atatagttcc cataagcaag cagtctgaag tatttaccct cagtaatctg     78660
aatgtataaa taaacaggat tcatgatggt agagtaattt atatatactt gtagtattag     78720
gacatgcaaa acttattttta tggaaaaaaa taatttacta cccttatagta tggcaactat    78780
```

```
acaaatctat aaattgactc ttttgtcccc ttgaaaaaaa gctgacataa aatttaaatg    78840
atgtgtattt tttcttagag caataaaaga tataccccca cctagaaaag caataaacca    78900
aaaaataaaa caaaaacaaa atcaagccct cttcacaaat ttgagcatat ctacagcttt    78960
atgtggtgag agatacagct accattcttg agtaatccga agagtcaaat ggtatggagc    79020
aaaattacag tcctaaatgc atattggtga aatgagatgc tgatccattt gcacactaat    79080
gtgctatttt taagtcatgc atcatagcat cttcaaagag gcctgtcata attatgatgg    79140
attagactgc agagtcagtc ctagatgcag taattgtttc acagatgctg ccaatgcgac    79200
tagaatttat aataaattat tttcagagag gcgggagaag gaacaaaatc aaaggaaaac    79260
tgctgtggct aaaacctgtt ttggtcttag gaaaccaaaa tgttagctag tagtcaaaag    79320
gccagtattt tcaactgaga taaacatgct tcattaatac atgcctctga catagaagat    79380
aaaggttaac ataattgaca tatcagccag tctctctctc tctctctctc tctctctctc    79440
tctctctctc tctgtctcgt agcttatgaa aatttattct ggggcattag ctgaaattat    79500
tgagtggcca tataattgtt gcatgtttct atttatgtta aattgcctgg ttataatttg    79560
acctttagaa tttctgaaaa aaatggtggt atttatagta aatagaaata ttcttttttgg   79620 ttccttggaa gcccatgcat tacaaagaac attagattat tggaataaaa ggatagacat    79680
acataatatg actagtggga tctaaattat aacctttaa aattgtaatt taattagtct    79740
gtcatttagg caaatgataa tttctaaaac tgccttttta gacttaaaaa aataccaaag    79800
ttcttataac tttagcatta tgttttgttc attcttaaag tttaattcac tttgttgcct    79860
ttttggtaaa cctatgaaga aatctcatgc tgcaccatat agtaaaaaat cgtgtgtgtg    79920
tgtgtgtgtg tgtgtgattt gaataatgag ctatgtgtta tattttgata agcaaagata    79980
agtttatagt gaagcagata aacatgccat gtattttcct aggttaaggg ttcaataatc    80040
agaagagctt ctacaactca tttgccttct cactagtttt tttgaaattg cgctctatga    80100
gttttttatg tggtgttctc tgtacttgct gactactgat gcacatttct ccttaggtca    80160
ctggttctcc tccctcagca atgttgtagg tagctttgat gaacattcgt tgtcagcctt    80220
ttacctttga cttagtgttt ttctctcata ctacggcaag aagaaatgaa gttaaatttt    80280
acaagagtga cttgggtggc tgatatgccc acattgacag ggacaagagc tctagtcttc    80340
ccctctcctg tattcccatg gcacttcagt agtctcattg cctcaacata accacagttc    80400
agggcagtag aggatgtttg catctttgtg ttagctccat gccatggcaa ctgcactgag    80460
tgaggattca actcagtgca gcaggactga aaaaataaat gaactaatgt gtcttgagct    80520
ccaattctct gagtgacatt atcaggggag attcataaat catcctcaaa tattctagag    80580
aaaaatcatc agcagtccag cattgcaaag ataatctggg aaggtggcaa agaagggatc    80640
agaataactc tgtggcagct tcaaattcca tgtcctaaaa gtttacgttt tctttttat    80700 tctatcccaa accacataaa gaaatgattt gttggcaaaa gacatgcaaa atgccccttaa   80760 tcatcttaat aattacagac ctacagatac gtagccaaaa tacttgtttt ttaatcctaa    80820
accttaaaaa aaaagcttaa attgttggct aaatgtgaat ttaataacaa aacttactcc    80880
tttaattatg cacttgtctt agtattgtgt ggtgggaaga gctttagaga gctgccagag    80940
tgcttaggcc tagtccctgt gggagcctct gttttggtgc ttcaccatgg gcagattcct    81000
cagttttcac atctttaaaa tgagaaaatg gtactagatc cttgctgcta ctctgaaatg    81060
tttatacatt gttaggacca ttgttacata ttattactta tatttgagtg tcaccttaga    81120
```

```
atttcttagc cgtgtgatat ggtttggttg ttggctcctc taaatctcct gttgaaatat    81180
aatccccagt gttggaggtg ggggcctggt gggaagtgtt tggattattg gggcagatcc    81240
ctcatggcat ggtgctgtcc tcctgatagt gagttctcaa gagatctggt taagggtgtg    81300
tggcacgtcc ccctccctgt ctccttccct ccctctctcc ttccctccct ctgtccttcc    81360
ctccctcttc ctccctcttc ctctctcttt ttctcccact ccagccatgt tagatgcctg    81420 ctccccttt  gctttctgcc atgattataa gttttgtaag gcctcaccca aagcagatgc    81480
cagtgctttg cctcctatac agcctgcaga accatgagcc aattaaacct attttcttat    81540
aaattaccca gacagctatt tctttatagc aactcaaaaa cagcctaaca tacctttcaa    81600
aaggttaaaa tgctatttag tcattccaga agcaagatct ctttgtccag aattctggaa    81660
ataaagatgc caaaataata tggcatgtat ttgatctcag ggaattttca tttttttcaaa   81720 aggaggaaaa aagagtaata taattttta atattttggt agctctaaca gtgcttagaa    81780
ccagttctca agagcacatt gtgaaacttt caggaattgc atgagctgta ggttgataac    81840
atgatgccag ctataaccca taagagcatc tcctgaggaa tatgttaaaa actgtattca    81900
ttcttaaatt ttaactaaat gcaatgagtg aagtattgac atcatgaaaa tcatccctgg    81960
gtaaacaatt agtcactcca ggttttccca aaggttcttc tgtctctgtt cttgtatata    82020
aacttcgtaa ccagtttaac aaccccaaaa aaggccttaa ttttgattgg ccagcatcct    82080
cttaggaaag acattgccat cctccttgtaa agttgcttct cattctaaaa taagaattgt    82140
ttccatctag ggaatgattt ttataggtag aatcttattt ggcatggact cttttgcata    82200
cagtgaatta caatgtgtag accttcaata gcaaggtgtt tgaatattta gttgcacaat    82260
agagcagtat cttaatattg tataccatat taattttgtg ttctctggtg taagaaaaaa    82320
tagaaggatg tttaatttca actaaaaaat caatcatgat aattcaaaat atttctgatg    82380
agtcatttat aagagcagat atgaattaaa attatatttt tgttcttagt ctctgagaag    82440
caaaaatcac acaaataatc tccatagcaa aaatttatat ttatctgaaa acagtttaa    82500 ctttgaaaaa cttttctttg caatcattta aattcataaa aaaaattcat taactctact    82560
ttcactgaat agcaggtgaa tagcaggtca atatctacaa aaattcatct ttgaagattt    82620
ttttatctta cgcaaaaatt attgacttca tgtagacttt ttatgcaagc ttgaaaacac    82680
tgtgtaaatg accccataaa aactacagca tgaaagcttt ttcagtattt ctacaatgag    82740
caaaatgcat aggtctcatt tccttctctt ttattaagca aaataatact ttatcaacat    82800
cagtatgcaa gcactaagag cttgaaagag tactgtgcaa gtgggttact ggatcataat    82860
attccagggt atgtatataa aaagtgtgat ttagcacata ttaaagtaaa agaaaatatt    82920 gcattttct ccttctaaaa tggcagttta ttagtttaaa tttcctgaaa taagatttaa     82980
agaccaataa caaattttcc tcattctaac atataacttt cctgcccttc ttgtgaaaaa    83040
gttaaccatt aaacttttca cacaaatggt tgtataaagg acttgctgtc acagacaaaa    83100
tagttctgta taatgtttaa aaatggccat tgtgtttaaa actccatatt gaaatacatt    83160
tcttttttag tcaccttcat ttcttagtag ctattattat actcaaagga tttgcccttg    83220
acactttaaa gaatgtccaa aattatgtgg aatggattat aataaaagat aatatattaa    83280
atgcttaaaa tattttatac cttagaaagt agaaaaacat gtattatgta cagatcctac    83340
aaattttata taatttatca taaatgtaca catgtatata catgtaaata ccttttgatt    83400
gctctgtata tgaattggtg ttttacagtt accaaaagaa aagtgccttt ttttggtagt    83460
atctggacag gtaattgact ttctttctgc aggatttatt tagatttatg tctatgctcc    83520
```

```
ttaattttg   aaaagtgata   gtgtcctgat   tttggagaag   cctctcatat   caaagactac   83580
aaatcaattt   tcatgatttt   aaaacctaaa   gtttctttat   taggtgttat   tgatgattaa   83640
aagccattgt   ctcacccaaa   ttttctactt   gttcaataga   aacataatgt   aagccacatg   83700
gaattttaca   ttttctagta   ctcacattaa   aacaagtgaa   aaagaaacaa   attgatgata   83760
cgtttgattt   aacccaatac   atttaaaata   gttcaacatg   tattaaatat   tttttgagta   83820
tttttgtgtt   ttttaacac   taaatctttg   aaatccaaac   taaatgtttt   catagatacc   83880
acatctcaat   ttggactaga   cacattttaa   gggctcaata   gctatatgtg   actagtcact   83940
gttggatgat   gtatatctag   accatctctt   aatgtatgga   aggaagtaaa   tctagcagaa   84000
ataaaaacat   cactttgttt   tctttgtcca   atatgagtta   taactttatt   ttttgagac   84060 agagtctcgc   tctgttgcca   ggctggagtg   cagtggcgcg   atctcggctc   actgcaacct   84120
ccgcctcctg   ggttcaaatg   attctcctgc   ctcagcctcc   caagtaactg   ggactacagg   84180
catgcgccac   catgcccagc   tacttttgt   atttttagta   gtggcggtgt   ttgaccacgt   84240
tggccaagat   ggtctcgatc   tcttgacctc   gtgatctgcc   tgcctcagcc   tcccaaagtg   84300
ctgggactac   aggcgtgagc   caccgtgcct   ggccttttat   tttatttatt   aagtaataca   84360
catgcttgga   agttatttaa   aaaaaaaaaa   aaggaatagt   taaagtaat   cccctccca   84420 gtgcttttct   ccagctgccc   cattccttt   cctggaggca   aattattatg   ccagttcat   84480 tatatattct   ccagagatga   ttttttttta   ttttacaaag   gtataggttg   tagcattctt   84540
atataaactg   ttgtgtagct   tcctttattc   catttaatta   ctgggagata   cttccatctg   84600
aaaatataga   gatactaatt   ttaatagcta   catggtatta   tattgtgtgg   ctgtaccata   84660
aattatttaa   cataacccctt   attgatgtag   gttgtttcta   accttttatt   actgcaaaag   84720
attgtgccta   catcatttaa   tgtatatatg   agcatatttg   tcagatatat   atatatatat   84780
tttttgagac   agtgtctcac   tctgtcaccc   aggctggagt   gcagcatcac   aatctcacct   84840
cactgcagtg   tccacctcct   gggttcaggt   gattcttctt   cctcagcctc   caagtaact   84900 gggattacag   gtgcctacca   ccatgccctg   ctaattttg   tatcttttta   ggagagacgg   84960
gatttcacca   tgttggccag   gttggtctag   aactcctggc   ctcaggtgat   ccactggcct   85020
tagcttccca   aagtgctggg   attataggcg   tgagctacca   cacccagcct   gtcagataaa   85080
ttcttaaaag   ggtcaaggaa   agtgtttctg   aaattttata   catattgcca   aattgtcatc   85140
ctacatgata   tttgtggcag   ttttgactct   caaaagccac   atgagagagt   atctgttttc   85200
ccacatgctt   gccaaacata   gtatagtatc   aagcttactg   atcttcacta   attggagaag   85260
agaaaaaaac   tgtaccttgt   tgcagtttta   atttgcattt   cttttatga   gcaatagtag   85320 atatcttctt   aaatacttaa   gagccattca   catttcattt   tctatgaact   gtccatgtcc   85380
cttgtccatt   ttttagtatg   tggttattca   tttatttgta   ggcgtcctat   atgttaagaa   85440 aagtttata   caacttttaa   ctctttttac   atgtttattt   tggcacatat   aaattttagc   85500
aaactttccc   atcttttatg   acttctagat   tttgtttcac   aaaaaaagag   cttagccagt   85560
cattagattt   ttttaagttt   tctcagattg   ttttaactt   tggggggggt   tttatttcct   85620
gtattcaaat   attaaattca   tctagaattt   atcttaaagt   gtaagggaat   gatcccactt   85680
tatcattttt   tcaggagatt   acccagttgt   tctaatatca   agtatgtctt   tgaaatccca   85740
tccttatctt   gtagcatatt   tctgtggttt   gggtctattt   ttgaacattc   tgttttattc   85800
cattgatcat   attaatatta   tatgtgcaaa   cacaaactat   tttaagtata   gtagctttgt   85860
```

```
tgcttttaaa tatcttttaa tttggctact aggccccata caattctttt tcagaatatt    85920
cctggctacc caatttgttt attttttccaa atgaactttg gagtcaactt ccttaattcc   85980
tcaaaatatt ctgcaagtac ttttagtaag agtatattaa gtgaataatt tgacaactat   86040
ctaagaacat attatagctt ttcccttgtt ttgtttttgt acttatatat tagtatagtt   86100
ttaaagttat attaaaatag gtcttccaca ttttaaaaac ttattcctag tgtattaatt   86160
tcttctatta taactacagt atttttattcc agtaaaactt ctgactggtt gatgctctta   86220
taaatcaagg ctataaattt ttcttcagct actttgctga attctcacaa actgtaacca   86280
tttttttactt gattctctag gttgaccagt atataatctt tttatctgta aacaataact   86340
ttagcgttgc tttcaacatc tatattctta ttctatttca tttttcttgt ttatcaagaa   86400
atagctgttt taatagagtt gttttttcgcc caaaagaaa atagtctttc tttttctact   86460
tatatcttta aaataaatgt aatgagaaag actgtgggaa aataaagcag acaccttata   86520
caatggatta attttttttag tgccatttct tctggctttc tctattattg ggactctgaa   86580
atcttcgtta gtactactct caaaaatgtt cgaatgaatg caatcagatt caagggtaca   86640
agtgcaggtt ataggtga attgcatgcc ttggggtttt ggtgtacaga ctattttgtc    86700
acccaggtaa taagcgtagt acttaatagg tagttttttg atcctctccc ttctcccatc   86760
ctcaaagtat ccctgctgtc tgttgttccc cctctttgtg tccatgtgtt cttgctgttt    86820
agctgccact taagagaaca tgtggtattt ttctgttcct ttgttagttt gtttaggata   86880
atggcctcca gctccatcca tgttgctgca cagaacacga ttttgtgttt ctttatggct   86940
gtgtagtatt ccatggtgta tatgtaacac tttcttttatc cagtctacta cttacgaca   87000
tttaggttga ttccatgtct tcgctatcat taatagtgct gtgatgaaca tacgtgtgca   87060
atatgccttt atggtagaat gatttatatc cctttgggta atatgccgaa taatgggatt   87120
gctcggtcag atggcaattc taagtcctct gaaattaccg cactgctttc cacaacagct   87180
gaactagttt acattcccac aagcaataag gggataagtg ttcccttttc tctgcaggaa   87240
tgattaattc ttttagagag tcaaagatgg aatcctaggg aagatgatat ctgaggcagg   87300
tttagagtca ttgggcaaat aaggggatta agaaggcatt ctaggcagac agaaaaccaa   87360
aggcatgaag ctctgaaaca gcttactatg tttggatatt tataagctgt tgttattgtt   87420
ggagtataaa ctgtaagaga gagtaggagg acagaaaaaa cagcctgtat gcggggggaa   87480
gaaaacattt aaacagaaat tctcaaaaga tttgggcagc cagcccctct agagaaaaac    87540
atagaatcac ctagaagggg ttttttcataa agtacacttt tcatcacccc tattctgtca   87600
cctggaatat tgataacact gaagggagtg tgccttatct ctcaggtgta tttggatgaa   87660
atagtttgag aaccatgcag gcaagtttaa gccagtgtgt taaagagaat atgacatcag   87720
atttgcattt tacaatcttc cttttgataa caaagggaac cttaaagggc tggaggggaa   87780
gggcagacgg ggctagggga ggagaacccct tttaaaaagc tactgcaggt ggggtgcggt   87840
ggctcacacc tgtaatccca gcactttggg aggccaaggc aggcagatca cctgaggtca   87900
ggagttcaag accagcctgg ccaacatagt aaaaccccat ctctactaaa aatacaaaaa   87960
ttagctaggc atggtagcag gcacctgtaa tctcagctac ttgggaggct gaggcaggag   88020
aattgcttga acctgggagg cagaggttgc agtgagccaa gattgtgccg ctgcactcca   88080
gcctgggcaa gagagtgaga ctccatctca aaaaaaaaa aaaaaagct actgcagtag   88140
atcaggagga ggcacagtga taagagaag atctgagcta tgaagtggca gtcaagatga   88200
ttaaaggaat atataggaag tacagttgat agaacttagc aagtgattag gtaaatgaag   88260
```

```
tgctagagaa aataaagggg atatttttca attgttttta gcattttggc aaaaaattat   88320
ttaggaatga aattgatgct agtaactaag agtatgaact ccccacatta gctggtaatt   88380
ttgatcaccc ttgttctcca tgaccataaa tattttagag ttgctatgaa gacaagaatg   88440
tttatttcct gagtagctgt cagttgtcac tatgaaacat gaaataaat atcagtttgc   88500 tatgtctagg tattccgata tttatccaca attattcctt aagatatatt agtatttta   88560 tagatagata gatagataga tagaaataaa cacatttaa tttttgtttc catgctcttt   88620
agaattcaac tagagggcag ccttgtggat ggccccgaag caagcctgat ggaacaggat   88680
agaaccaacc atgttgaggg caacagacta agtccattcc tgataccatc acctcccatt   88740
tgccagacag aacctctggc tacaaagctc cagaatggaa gcccactgcc tgagagagct   88800
catccagaag taaatggaga caccaagtgg cactcttca aaagtattta tggaataccc   88860
tgtatgaagg gaagccagaa tagtcgtgtg agtcctgact ttacacaaga aagtagaggg   88920
tattccaagt gtttgcaaaa tggaggaata aaacgcacag ttagtgaacc ttctctctct   88980
gggctccttc agatcaagaa attgaaacaa gaccaaaagg ctaatggaga aagacgtaac   89040
ttcggggtaa gccaagaaag aaatccaggt gaaagcagtc aaccaaatgt ctccgatttg   89100
agtgataaga aagaatctgt gagttctgta gcccaagaaa atgcagttaa agatttcacc   89160
agtttttcaa cacataactg cagtgggcct gaaaatccag agcttcagat tctgaatgag   89220
caggagggga aaagtgctaa ttaccatgac aagaacattg tattacttaa aaacaaggca   89280
gtgctaatgc ctaatggtgc tacagtttct gcctcttccg tggaacacac acatggtgaa   89340
ctcctggaaa aaacactgtc tcaatattat ccagattgtg tttccattgc ggtgcagaaa   89400
accacatctc acataaatgc cattaacagt caggctacta atgagttgtc ctgtgagatc   89460
actcacccat cgcatacctc agggcagatc aattccgcac agacctctaa ctctgagctg   89520
cctccaaagc cagctgcagt ggtgagtgag gcctgtgatg ctgatgatgc tgataatgcc   89580
agtaaactag ctgcaatgct aaatacctgt tcctttcaga aaccagaaca actacaacaa   89640
caaaaatcag tttttgagat atgcccatct cctgcagaaa ataacatcca gggaaccaca   89700
aagctagcgt ctggtgaaga attctgttca ggttccagca gcaatttgca agctcctggt   89760
ggcagctctg aacggtattt aaaacaaaat gaaatgaatg gtgcttactt caagcaaagc   89820
tcagtgttca ctaaggattc cttttctgcc actaccacac caccaccacc atcacaattg   89880
cttctttctc cccctcctcc tcttccacag gttcctcagc ttccttcaga aggaaaaagc   89940
actctgaatg gtggagtttt agaagaacac caccactacc ccaaccaaag taacacaaca   90000
cttttaaggg aagtgaaaat agagggtaaa cctgaggcac caccttccca gagtcctaat   90060
ccatctacac atgtatgcag cccttctccg atgctttctg aaaggcctca gaataattgt   90120
gtgaacagga atgacataca gactgcaggg acaatgactg ttccattgtg ttctgagaaa   90180
acaagaccaa tgtcagaaca cctcaagcat aacccaccaa ttttttggtag cagtggagag   90240 ctacaggaca actgccagca gttgatgaga aacaaagagc aagagattct gaagggtcga   90300
gacaaggagc aaaacacgaga tcttgtgccc ccaacacagc actatctgaa accaggatgg   90360
attgaattga aggcccctcg ttttcaccaa gcggaatccc atctaaaacg taatgaggca   90420
tcactgccat caattcttca gtatcaaccc aatctctcca atcaaatgac ctccaaacaa   90480
tacactggaa attccaacat gcctgggggg ctcccaaggc aagcttacac ccagaaaaca   90540
acacagctgg agcacaagtc acaaatgtac caagttgaaa tgaatcaagg gcagtcccaa   90600
```

```
ggtacagtgg accaacatct ccagttccaa aaaccctcac accaggtgca cttctccaaa    90660
acagaccatt taccaaaagc tcatgtgcag tcactgtgtg gcactagatt tcattttcaa    90720
caaagagcag attcccaaac tgaaaaactt atgtcccag tgttgaaaca gcacttgaat     90780
caacaggctt cagagactga gccatttca aactcacacc ttttgcaaca taagcctcat     90840
aaacaggcag cacaaacaca accatcccag agttcacatc tccctcaaaa ccagcaacag    90900
cagcaaaaat tacaaataaa gaataaagag gaaatactcc agacttttcc tcaccccaa    90960 agcaacaatg atcagcaaag agaaggatca ttctttggcc agactaaagt ggaagaatgt    91020
tttcatggtg aaaatcagta ttcaaaatca agcgagttcg agactcataa tgtccaaatg    91080
ggactggagg aagtacagaa tataaatcgt agaaattccc cttatagtca gaccatgaaa    91140
tcaagtgcat gcaaaataca ggtttcttgt tcaaacaata cacacctagt ttcagagaat    91200
aaagaacaga ctacacatcc tgaactttt gcaggaaaca agacccaaaa cttgcatcac    91260
atgcaatatt ttccaaataa tgtgatccca aagcaagatc ttcttcacag gtgctttcaa    91320
gaacaggagc agaagtcaca acaagcttca gttctacagg gatataaaaa tagaaaccaa    91380
gatatgtctg gtcaacaagc tgcgcaactt gctcagcaaa ggtacttgat acataaccat    91440
gcaaatgttt ttcctgtgcc tgaccaggga ggaagtcaca ctcagacccc tccccagaag    91500
gacactcaaa agcatgctgc tctaaggtgg catctcttac agaagcaaga acagcagcaa    91560
acacagcaac cccaaactga gtcttgccat agtcagatgc acaggccaat taaggtgaa    91620 cctggatgca agccacatgc ctgtatgcac acagcaccac cagaaaacaa acatggaaa    91680 aagtaacta agcaagagaa tccacctgca agctgtgata tgtgcagca aaagagcatc     91740 attgagacca tggagcagca tctgaagcag tttcacgcca agtcgttatt tgaccataag    91800
gctcttactc tcaaatcaca gaagcaagta aaagttgaaa tgtcagggcc agtcacagtt    91860
ttgactagac aaaccactgc tgcagaactt gatagccaca ccccagcttt agagcagcaa    91920
acaacttctt cagaaaagac accaaccaaa agaacagctg cttctgttct caataattt     91980 atagagtcac cttccaaatt actagatact cctataaaaa atttattgga tacacctgtc    92040
aagactcaat atgatttccc atcttgcaga tgtgtaggta agtgccagaa atgtactgag    92100
acacatggcg tttatccaga attagcaaat ttatcttcag atatgggatt ttccttcttt    92160
ttttaaatct tgagtctggc agcaatttgt aaaggctcat aaaaatctga agcttacatt    92220
ttttgtcaag ttaccgatgc ttgtgtcttg tgaaagagaa cttcacttac atgcagtttt    92280
tccaaaagaa ttaaataatc gtgcatgttt attttcct ctcttcagat cctgtaaaat     92340
ttgaatgtat ctgtttaga tcaattcgcc tatttagctc tttgtatatt atctcctgga     92400
gagacagcta ggcagcaaaa aaacaatcta ttaaaatgag aaaataacga ccataggcag    92460
tctaatgtac gaactttaaa tatttttaa ttcaaggtaa aatatattag tttcacaaga     92520
tttctggcta atagggaaat tattatcttc agtcttcatg agttgggga aatgataatg      92580 ctgacactct tagtgctcct aaagtttcct ttctccatt tatacatttg gaatgttgtg     92640
atttatattc atttttgatc cctttctct aaaatttcat cttttgatt aaaaaatatg      92700 atacaggcat acctcagaga tattgtgggt ttggctccat accacaataa aatgaatatt    92760
acaataaagc aagttgtaag gacttttgg tttctcactg tatgtaaaag ttatttatat     92820
actatactgt aacatactaa gtgtgcaata gcattgtgtc taaaaatat atactttaaa     92880 aataatttat tgttaaaaaa atgccaacaa ttatctgggc ctttagtgag tgctaatctt    92940
tttgctggtg gagggtcgtg cttcagtatt gatcgctgtg gactgatcat ggtggtagtt    93000
```

```
gctgaaggtt gctgggatgg ctgtgtgtgt ggcaatttct taaaataaga caacagtgaa  93060
gtgctgtatc aattgatttt tccattcaca aaagatttct ctgtagcatg caatgctgtt  93120
tgatagcatt taacccacag cagaatttct ttgaaaattg gactcagtcc tctcaaactg  93180
tgctgctgct ttatcaacta agttttttgta attttctgaa tcctttgttg tcatttcagc  93240
agtttacagc atcttcattg gaagtatatt ccatctcaaa cattctttgt tcatccataa  93300
gaagcaactt cttatcaagt tttttcatga cattgcagta actcagcccc atcttcaggc  93360
tctacttcta attctggttc tcttgctaca tctccctcat ctgcagtgac ctctccacgg  93420
aagtcttgaa ctcctcaaag taatccatga gggttggaat caacttctaa actcctgtta  93480
atgttgatat attgaccccc tcccatgaat tatgaatgtt cttaataact tctaaatggt  93540
gatacctttc cagaaggctt tcaatgtact ttgcccggat ccatcagaag actatcttgg  93600
cagctgtaga ctaacaatat atttcttaaa tgataagact tgaaagtcaa aagtactcct  93660
taatccatag gctgcagaat caatgttgta ttaacaggca cgaaaacagc attaatcttg  93720
tgcatctcca tcggagctct tgggtgacta ggtgccttga gcagtaatat tttgaaagga  93780
ggttttggtt ttgttttttg ttttttttttt ttgtttttta gcagtaagtc tcaacactgg  93840
gcttaaaata ttcagtaaac tatgttgtaa aaagatgtgt tatcatccag actttgttgt  93900
tccattactc tacacaagca gggtacactt agcataattc ttaagggcct tggaattttc  93960
agaatggtaa atgagtatgg gcttcaactt aaaatcatca actgcattag cctgtaacaa  94020
gagagtcagc ctgtcctttg aagcaaggca ttgacttcta tctatgaaag tcttagatgg  94080
caccttgttt caatagtagg ctgtttagta cagccaccttt catcagtgat cttagctaga  94140
tcttctgcat aacttgctgc agcttctaca tcagcacttg ctgcctcacc ttgtcctttt  94200
atgttataga gacagctgcg cttcttaaac tttataaacc aacttctgct agcttccaac  94260
ttctcttctg cagcttcctc attctcttca tagaactgaa gggagtcaag gccttgctct  94320
ggattaagct ttggcttaag gaatgttgtg gctgacgtga tcttctatcc agaccactaa  94380
agcgctctcc atatcagcaa taaggccgtt ttgctttctt acctttcatg tgttcactgg  94440
agtaatttcc ttcaagaatt ttttccttac attcacaact tggctaactg gcatgcaagg  94500 cctagcttc agcctgtctt ggcttttgac atgccttcct cacttagctc gtcatatcta  94560
gcttttgatt taaagtggca ggcatacaac tcttcctttc acttgaacac ttagaggcca  94620
ctgtagggtt attaattggc ctaatttcaa tattgttgtg ttttagggaa tagagaggcc  94680
cagggagagg gagagagccc aaacggctgg ttgatagagc aggcagaatg cacacaacat  94740
ttatcagatt atgtttgcac catttaccag attatgggta cggtttgtgg cacccccccaa  94800 aaattagaat agtaacatca aagatcactg atcacagatc gccataacat aaataataat  94860
aaactttaaa atactgtgag aattaccaaa atgtgataca gagacatgaa gtgagcacat  94920
gctgttgaaa aaaatgacac tgatagacat acttaacacg tgggattgcc acaaaccttc  94980
agtttgtaaa agtcacagta actgtgactc acaaaagaac aaagcacaat aaaacgaggt  95040
atgcctgtat ttttaaaaaa agcttttttgt taaaattcag gatatgtaat aggtctgtag  95100
gaatagtgaa atatttttgc tgatggatgt agatatatac gtggatagag atgaagatct  95160
taattatagc tatgcagcat agatttagtc aaagacatttt gaaaagacaa atgttaaatt  95220
agtgtggcta atgacctacc cgtgccatgt tttccctctt gcaatgagat accccacact  95280
gtgtagaagg atggagggag gactcctact gtccctcttt gcgtgtggtt attaagttgc  95340
```

| | |
|---|---|
| ctcactgggc taaaacacca cacatctcat agataatatt tggtaagttg taatcgtctt | 95400 |
| cactcttctc ttatcaccca cccctatctt cccactttc catctttgtt ggtttgcaac | 95460 |
| agccccttct ttttgcctga ctctccagga ttttctctca tcataaattg ttctaaagta | 95520 |
| catactaata tgggtctgga ttgactattc ttatttgcaa aacagcaatt aaatgttata | 95580 |
| gggaagtagg aagaaaaagg ggtatccttg acaataaacc aagcaatatt ctggggtgg | 95640 |
| gatagagcag gaaattttat ttttaatctt ttaaaatcca agtaataggt aggcttccag | 95700 |
| ttagctttaa atgttttttt tttccagctc aaaaaattgg attgtagttg atactacata | 95760 |
| taatacattc taattccctc actgtattct ttgtttagtt tcatttattt ggtttaaaat | 95820 |
| aatttttat cccatatctg aaatgtaata tattttatc caacaaccag catgtacata | 95880 |
| tacttaatta tgtggcacat tttctaatag atcagtccat caatctactc attttaaaga | 95940 |
| aaaaaaatt ttaaagtcac ttttagagcc cttaatgtgt agttgggggt taagctttgt | 96000 |
| ggatgtagcc tttatattta gtaaattga ggtctaaaat aataatcttc tattatctca | 96060 |
| acagagcaaa ttattgaaaa agatgaaggt cctttttata cccatctagg agcaggtcct | 96120 |
| aatgtggcag ctattagaga aatcatggaa gaaaggtaat taacgcaaag gcacagggca | 96180 |
| gattaacgtt tatcctttg tatatgtcag aattttcca gccttcacac acaaagcagt | 96240 |
| aaacaattgt aaattgagta attattagta ggcttagcta ttctagggtt gccaacacta | 96300 |
| cacactgtgc tattcaccag agagtcacaa tatttgacag gactaatagt ctgctagctg | 96360 |
| gcacaggctg cccactttgc gatggatgcc agaaaaccca ggcatgaaca ggaatcggcc | 96420 |
| agccaggctg ccagccacaa ggtactggca caggctccaa cgagaggtcc cactctggct | 96480 |
| ttcccacctg ataataaagt gtcaaagcag aaagactggt aaagtgtggt ataagaaaag | 96540 |
| aaccactgaa ttaaattcac ctagtgttgc aaatgagtac ttatctctaa gttttctttt | 96600 |
| accataaaaa gagagcaagt gtgatatgtt gaatagaaag agaaacatac tatttacagc | 96660 |
| tgccttttt ttttttttc gctatcaatc acaggtatac aagtacttgc ctttactcct | 96720 |
| gcatgtagaa gactcttatg agcgagataa tgcagagaag gcctttcata taaatttata | 96780 |
| cagctctgag ctgttcttct tctagggtgc cttttcatta agaggtaggc agtattatta | 96840 |
| ttaaagtact taggatacat tggggcagct aggacatatt cagtatcatt cttgctccat | 96900 |
| ttccaaatta ttcatttcta aattagcatg tagaagttca ctaaataatc atctagtggc | 96960 |
| ctggcagaaa tagtgaattt ccctaagtgc cttttttttg ttgtttttt gttttgtttt | 97020 |
| ttaaacaagc agtaggtggt gctttggtca taagggaaga tatagtctat ttctaggact | 97080 |
| attccatatt ttccatgtgg ctggatacta actatttgcc agcctccttt tctaaattgt | 97140 |
| gagacattct tggaggaaca gttctaacta aaatctatta tgactcccca agttttaaaa | 97200 |
| tagctaaatt tagtaaggga aaaaatagtt tatgttttag aagactgaac ttagcaaact | 97260 |
| aacctgaatt ttgtgctttg tgaaatttta tatcgaaatg agctttccca ttttcaccca | 97320 |
| catgtaattt acaaaatagt tcattacaat tatctgtaca ttttgatatt gaggaaaaac | 97380 |
| aaggcttaaa aaccattatc cagtttgctt ggcgtagacc tgtttaaaaa ataataaacc | 97440 |
| gttcatttct caggatgtgg tcatagaata aagttatgct caaatgttca aatatttga | 97500 |
| ttgcctcttg aattcatttg ctaattgtat gtgtgtgtgt ttctgtgggt ttctttaagg | 97560 |
| tttggacaga agggtaaagc tattaggatt gaaagagtca tctatactgg taaagaaggc | 97620 |
| aaaagttctc agggatgtcc tattgctaag tgggtaagtg tgacttgata aagcctttgg | 97680 |
| tcttaaatct tgggcatttt gatttgtaaa tctgaccctg agaattgggt tacccagatc | 97740 |

```
aaagactcat gccagttaaa aagaacatta cctgtatttt ttatcatgtg ttatctctta    97800
agaagaggca gattagttct aaaatcaaca aattgtattt aattgaaata atttagtgat    97860
gaggaagagg tccattctag tgcctgctaa atgtataatc cttcttagaa tgtgaagttg    97920
tccttaaact tttaaatacc ttcagttaat ctttatattg tcatttatga aaaccttgaa    97980
ctaagactta tgtatctttc atctagctct ggttttaatg caggtagcat ttaattgtcc    98040
ccactgtact gggtatagtc tgctaaacat taaggagtag ttttgcatct ctccttgttc    98100
tgatactagg gtcaaagccc acttttata gatgggcagc aaaaggcaca ttggacatgc     98160
tgataaatgt tgccctaatt gtgatctaaa catgataaaa tatacataca taagtgccct    98220
tatctgctgc aagtgaccct tgttttgttt tggttggggt gggggtgtt tgggatggaa     98280 tggtgatcca cgcaggtggt tcgcagaagc agcagtgaag agaagctact gtgtttggtg    98340
cgggagcgag ctggccacac ctgtgaggct gcagtgattg tgattctcat cctggtgtgg    98400
gaaggaatcc cgctgtctct ggctgacaaa ctctactcgg agcttaccga gacgctgagg    98460
aaatacggca cgctcaccaa tcgccggtgt gccttgaatg aagagtaagt gaagcccagg    98520
gcctctcccc tctttgcggc cactgatagg aaagcccaat ctttggttga aggaagaga    98580 gttcagcgtg cactttaca tttataaaat gggcatcaaa atgcctgttt ggcagtcatg     98640
cgataagaag ttgtatttgc taatgtgaat aacttgagat gatttcatta tctgaattgt    98700
acagtttagc cattaattag gagcagtcag agtgtctgta accacatggc ctcagttata    98760
ccataaactt gaaattgttt atgtgctcac atgctacaag tgacggctcc tgtgtgcctg    98820
gccactatat tagtatgtat tgactccact tccatgttgc agtatctgaa acagaaagta    98880
agtctaatga gaaactttgg gattcccagg tcaaatacct tccatatgta tgtagcaaaa    98940
acaaaataca aagcctagaa gttctgtaga aatagaactg atttttactt tcattcaaac    99000
tattcattat ttccacaata gtaatcaaaa ctgcttctac ttttactgct gctaaatgat    99060
cagcaaatta ctggatatgg atatatatta ttttccagga atataagaat ttagaataga    99120
actgcaagag tatgcactta aatatatttta gtgcatccag ttgctaatgt tttgttttaa   99180
acaccatcca ctttgcatga agtctaaacc ttcagttgga aaaagcctca ttttaatat    99240 tcctctactg tgctgataat cctgtataac actaaaagaa tagatgaatg ttcacggtgc    99300
tacacagaaa tgttttttt ttttttttt ttttttttga gatggagttt cgctcttgtt      99360
gcccaggctg gagtgcaatg gcgcgatctt ggttcaccgc gacctccacc tcccaggttc    99420
aagagattct cctgcctcag cctccctagt agctgggatt acaggcatgt gccaccacac    99480
ccggctaatt ttgtattttt agtagagaca gggtttctcc atgttggtca ggctggtctc    99540
gaactcccga cctcaggtga ttgcccacct cggcctccca aagtgcctta caggcatgag    99600
ccgccgcgcc tggccagaaa tcttacaagt tattttgccc acgattggtt ttaaaataat    99660
tttaattttg cactatttcc tttagtgtct ttttctctgc atccaccaaa ctatagaatc    99720
atttgctgag cttataagaa atgctcatac tgctcattgc aacagctagc caaatttgtc    99780
ctttgctgtt taaaactcta actagcatgg ttttactaaa tttatgttaa cacagtttct    99840
ctctctgggt tgtggggaga caaatcaatt ataaataatc tctttagaaa agttactctt    99900
tctatatgaa agtgtgactt gactttctat gataattatg atccaaaaat tttatggtgt    99960
gtacctgacc acttttacaa atgattaatt ggaaggtaga aattgctgat tcataacatg   100020
taacttataa acttatgatg gactactta agcataaatt tttttttttt ttttaagaca   100080
```

```
gagtttcact ctgtcaccca ggctggagtg caatggtgcg atctcggctc actgcaacct  100140
ccatctcctg ggttcaagca attctcctgc ctcagcctcc cgaatagctg ggattacagg  100200
catgcactac cacacccagc taattttgta tttttagtag agacagggtt tctccatgtt  100260
gatcaggctg gtctggaact cctgacctcg ggtgatccgc ccgcctcggc ctcccagagt  100320
gctgggatta caggcatgag ccactgtgcc cagcctgaaa tattttttta atctaccctg  100380
actcctcttg ctctttctga agaaaaattt ttaaaaatgt atgtaggtgc ctttaattag  100440 aaaaaaatt aaaaattaag gcaacttgtg ctcatattgg taatagcatt tctttcaaga  100500
actcagtaat actgcattgt ctttaaagca taatatctct tagacttgac ggtttgagat  100560
tctaaatcac tgaagaacct cttgtgaaaa tgatagtttt aaaatttctt ttcaaaaata  100620
gtcctattgc aaaatgtttg atttttcttga agtttcctgg aaactatatt tcattcattg  100680
taatgaattt aattttcatt aacatagatc tctaatattt ttctcagctc accacaacct  100740
ccacctcccg ggttcaagtg attctcatgc cacagcctcc cgagtagcta gaattacagg  100800
cacccacccg gctcatttt gtattttag tagagacagg gtttcaccat gttggccaga  100860
ttgatctcga actcctggct tcaggtaacc cacccaccct ggcctcccaa agtgctggga  100920
ttacaggtgt aggccaccat gcccagccag cttttccata attcttataa atgccaatgc  100980
ctgaaatgga atctgacata taaaaaatta catgaagaac ttttattatt ttgcatttga  101040
aaaccatgaa aaatagttgg accagagtct cagaaagctt gtagtttgtt agtttaactg  101100
ctctaaatgt caggcagata caaaactatt aaaagacatg cttcaaatat gaagacaatt  101160
taaaagcaca gctgtacact tttgctttt gtctagtttc aaggtaaaga tgaataatca  101220
tttagataat gcttaagcta tgcttatgca tacttagagc aattctccaa aataaaaaat  101280
tttaatactt aaatacatga ttaaaataga cacgtatcca atgtcaatac agactttact  101340
cagaaatagc ttttgaagtt tcttctaccc cataaataga ttttatttta tggctggcag  101400
aaatgaaaat tacaacttt tgccaagaac agagaataga ataatctcaa attggggctg  101460
cggactcagt tttatgttca aagctgtgtg aacctcatca ctgagttctt acaaatccct  101520
gtgtccacat gctccaaacc acccactgtg agttcagaaa agaactctga gtgcatcttt  101580
cagtaggaaa gtaaaaactg attttttacat ttcctttgag ccaaaccagc tgtttcttct  101640
ttaaagattt ccctttgaga tttccatttt atgactaagt ctaaccagta ttttttggc  101700 aagtaagagt tgtgggagtg tatctgtcat cataaggaaa tcaaagccag aaatgccttc  101760
tgccatggtg ggtgatgtta aacatttcaa ggaactttat attataaaaa ttgtcaaaca  101820
taaaaggaaa agtgcaatat aatgaattcc atggacccat cacacagcat caatatttat  101880
caacatttta tcaatatttt ttcatatatt tttcccacat ccactcccac tagtgtttga  101940
aagcagaaga cagataactt accatcttac ctgttaacat ttcaggatgt atttctaaca  102000
ggtaaagact ttatcattta atattagac tgtgtttgtt caaattatct gattagattc  102060
tatttcagaa aacacacaca taaacaaaaa tgataatgag aaaagaaag cccttccaca  102120 tgattgacac ttctgagtag tgtgatccca gttcatgtcc attgtctggg atagctatta  102180
aataaaactt cctctcataa aattctctcc atttagaaga taaattctgt gattcacaag  102240 cctctttta tttataatag ccccttcccct ttctttatga atttgaattt gttttttaaa  102300
gaaactgtga ttttctctgt aaaattcccc acattctgga tttggccgat tcatcttgg  102360 ttcttttgtt tactttaacc tattcctcta tccccagtat cttctgtgga ctggtagttt  102420
gactggttct ttttctttc ttttttttt ttttttttt ttttgagac aggctctcgc  102480
```

```
tctgtcgctt aggctggagt gcagtggccc aatctcagct cactgcaacc tccacctccc 102540
aggttcaagc tattctcatg cctcagcctc ctgagtaact gggactgcaa gcatgtgcca 102600
cctcatcctg ctgattttg  tacttttagt agagacgggg tttcgccatg ttggccaggc 102660
tggtctggaa ctcctggcct caagtgatcc gcccaccttg gcctcccaaa gtgctgggat 102720
tacaggcatg agctatcacg cccagctgat ttttaagtaa tataagtatg tgtgcatgta 102780
tagtatacat tggcaaaaac acttcataag tagtgctaaa atcatcttat ttatatacat 102840
caggagacac ataatgtctg tttgtttccc attttagtga tattaagagt gtttagcatg 102900
tttagttgtc agcctgatcc atcattatgt tcttcatcaa actttcacca gatagtttca 102960
catcaattga tgatcattgc ctgtttctat tattttgttt tcaagttgac agttttctct 103020
cacttgatgt tgtgtaaatt tagttatata aagttaaatt attttgctat ttttttctatg 103080 ctgtatacat ttgaataact gacctaattt ttactttaaa aatattttac aattagaagt 103140
ccaaatagta aatcaaaggt taagaatttt tgcagaaatc tgttatatag atgacatttt 103200
aatatttgcc ctttatatca tttaccatga gccaaatttc aagtcatatt aaaatgactg 103260
tcatgtgcta attctaacaa tatttgaaag acccctatca aaataaatat aacctttagt 103320 agccactta  ttagaaaatc aactttaagt tattcccca  tgttttttc taattgagat 103380 ataattcaca taccataaaa tttaccctt  taaagtatac aattcagttg tttcagtaca 103440
ttcacaaagc tatgcaaatg tcacctctac ctagttcag  aacgttttca tcattcccag 103500
aaggaaaccc tgtatttatt aggcagtcac ttccccttct cccccttcttc cttcctctaa 103560 gtggcaacca caaataaaca ttcagtttct ctggatttac ctattctggg cattttgtat 103620
tagtgaaatc atgtatttgg cctttctctc tggcttcttt catgtacctc aatgttttca 103680
agtctcattc attttattaa aaaaaaaaag tacctttttt cttttctttt ttttttttt 103740 tgtccacgta tatattcaca ccacattttt tgagacagag tctcgctctg ttgcccaggc 103800
tagggtgcaa tggtgcaacc tcagctcact gcaacctctg tctcccgggt tcaagtgatt 103860
ctcatgcctc agcccccaag tagttgggat tacagttgtg caccaccaca cccagctaat 103920
ttttgtattt ttagtagaga cagggtttca ccatgttggc taggctggtc tcaaactcag 103980
cctcaagtga tccttctacc ttagcctcct aaagtgctgg gattacaagc atgagccact 104040
gtgcccagcc acatttctt ttttccatta ttagttaatt gacatttgga tcgttctac 104100 tttttggcga ttataaatta tgctgcaatg aacatcggtg tacaagtttt tgtgtgaaca 104160
tgttttcagt taccttggga tatacaccta ggagtgacat tgttagtaat atggtaactt 104220
tatgtttaac tttttgaaga actgccaaac tgttttccaa agtagcttta tgcttttaca 104280
tttctgccaa caatgtatga aggttccagt gtatctccac atcctcaaga aaatgttatt 104340
gtctttttaa ttgtaaccat ccaagtgggt atgaagttta tctcgtgatt ttgatttgca 104400
ttttcctaat ggctgatatt gggcatcttt tcacgtgtgt attgaccatg tatttttttg 104460
agaaaagtct acttatatgt ttttaattgt attattttta gagttgtaag aatatgttat 104520
gttgatactt gaactttgtc aaatgcctgg tttgcagata ttttctccta tcccacaggt 104580
tgtcgcttca ctttgataat gtccttaaag tacaaaagtt ttaaattgat tttgatgaaa 104640
ctcaatttct ttttaattgg cagcttgtgc atttggggtc atatttaaga aatcattgcc 104700
tcattcaaga tctgaaagat ttacacctat gctttcttct cagagtatta aactttagt  104760 tcttacattt agattttaa  ttaatgttga gttaatttga tggtgagaga taagagtcca 104820
```

```
acttcattcc tttgcaagta gctgtccagt tttctcagca ccatttgtta aaagactgtt   104880
ttttttcaat taactgacca agatgtatgg gtttatttct ggactcttaa ttctgttaat   104940
ctgcatgact tttcttatgc cagtaccaca ctgtgctgat tcctgtagtt ttgtagtaaa   105000
ttttgaaatc aagacaggta agtcttccaa ctttgtactt ttgcctacca tgtttcttgg   105060
gtttccatat gcattttaag atcagcttct ccgtttcctt tctggatttt tttttttttt   105120
tttttttttt tttttttggt ggagctggag tcttactata ttacccaagc tggttttgaa   105180
ctcctggcta aagagatcct ccctcctagg cttcccagag agctggggtt acaggcatga   105240
gccaccacat ccaaccccct tctgggactt tgactggggt tctgttgaat ctgttggtca   105300
atttggagag tattgatatc ttaacattaa agcttccaat ttatgaacac aggctatttt   105360
tccatttatt cttaaatttc tttcagtaat gttttggatg aaacatgtac aaagtcctgc   105420
actttttatt tttttttaaga cagagtcttg ctctgctgcc cagtccagag tgcagtgctg   105480
ccatctcagc tcactgcaac ctccacctcc gggttcaagt gattctcctg cctcagctgg   105540
aactacaggt gcgcgccacc atgcctggct aattgttttg tgttttttggt ggagacaggg   105600 tttcaccatg ttggccaggc tggtctcaaa cacctggcct caagtgacct gactgccttg   105660
gcctcccaaa gtactgggat tacaggcatg agccaccacg cctggcctgt acttctgtta   105720
aaattttttc tatgtatttt ttttatccta ttgcaaaatc aaatttttttg ttgataatat   105780 atggtcataa atttcatttt tatatattgg tctcatatcc taccaacttg ctgaactagc   105840
ttattagcac taactttttt tggtagattc cttaggattt gctgcataca agattatgtc   105900
atctacaagt agagatagtt ttgtttcttc acttccaatc tgggtggctt tatgttttttt   105960 tcttgcctga ttacccagtt agaacttcca gaaaatgtca ggtacaatta acaactgcaa   106020
acatccttgt cttattcatt ttagaaagaa attttttagtt tttcaccatt aagtatgata   106080
ctagttgtag gttttgttta aaaaaagact gtgtcaagtt cagaagttcc cttctgttgc   106140
tagtttgttg aataattta tcacgaaagg gtgttgaact tttctcaaat gctgtggcta   106200
catctaatga aatgatcatg cgttcttctc ctttattcta ttaatatggt atattatatt   106260
gattcatttt tatacattag attaacatta tatttctgga ataaatccca cttggcctca   106320
gtgtgtatta cttttatat attgctggag tctgtttgca ggtatttcat tgaggacttt   106380
cgcatctctg ttgataaggt atactgatct ttagttctct tgtgatatct ttggttttgg   106440
tgtcagagta attctgagtt cacaaaatgc attgggaaat gttcccttct ctatcttttg   106500
gaagagttta caaaggattg gtttaactct tttttaaatg tttgaggaaa ttctctaccc   106560
ctgggctttc ctttgtggga atttttaaac atttttaaaa tagattattt ttaaagcaat   106620
tttagggtaa aagcacattg aatgaaaggc acagagcttc cttaagtaca tgctgcccct   106680
gtatgtgcat agcctccctc attatcaaca tcctttacca gaatggtaca tttgttgcag   106740
tcaatgaacc tgcattgaca attgtcgatg aaagttcata gtttagagtt caccctttggt   106800 gttatgtatt ctgtgagtct ggatccatgt ttaatgatac tcattcacca ttacagtatc   106860
attcagagta atttcactgc cttaaaagtc ctctgtaccc tacctatttt tctctcctac   106920
cccactaacc cttagcaacc aatgatcttt ttatctcaat aatttttgcct attccagaat   106980 gtcatatagt tggaatgata cagtatatgg agccttttca gactggtttt tgtcacttag   107040
taataagctt ttaaatttttc caccatgtca tgatcgttca tttcttttttca gcattgaata   107100 atattccatt gtctggttta tcacagttga tttatccatt cacatagtga aagacatctt   107160
agttgcttcc aagttttgac aattatgaat aaagctgtta taaaagtatg taggttttg   107220
```

```
tgtggacaaa agttttcagc tcctttgagt aaataacaca gagcacagta gcttgattga 107280
cagtaagagt aagaaatatt ttttctcagt ctgtgtctta tttttttcatt cacttgacag 107340 tgccatttgc agaacaaaca gaaagtttta attttaatga agtctaggtt atcagttaat 107400
tcatgaataa tgtttttggt attgtatcta aaaagtcaac accaaggtca tctatatgtt 107460
ctgtgttatc ttccagaaat tttatagttc tgcattttac atttagggct gtgacccatt 107520
ttgcattaat tttgcaaaag ctataaagac tatgtataga ttcacttgtt tgcatgtgga 107580
gttgtccagt tgttcccgta ccatttctta aagactatct ttgctttatt gtattacctt 107640
tgctactttg tcaaagatca gttgattata attaagtggt ctgtttctgg actctttatt 107700
ctgttccatt gatatatttg tctagacttt caccaatacc acactatctt gttaacttag 107760
gctttagagt aagtcttgca atcatgtagt gtcagtcctc tgacattgtt tttctccttc 107820
agtattgagt tggctattct tttgcctatt actaagtaaa aaaagcagtc tgaaaaggct 107880
atatatacag tcatttattg gtcttttgcc tcttgatata aactttaaaa ttactttgtc 107940
agtatcctca aaatcttgca ggaattttga tagattgcac tgcatttcta gattgagtta 108000
gaaatactgc catcttgaca atacacatct tcctatccat gaacatggaa catctctttc 108060
ttggatatcc ttcattagaa ttttgcattt tccccatata gaccatgtac atattagatt 108120
tatacataaa tatttcattt ggggggggtgc taatggtaat gtatttttat ctcagattct 108180
gcttgtacat tgctggtatg cagaaaagtg atcaactttt gtatattaaa cttgtttcct 108240
gcaaccatgt tatataatca ctttagatcc agttttttttt tttttggtca ttctttcata 108300
ttttctaggt gatcatgtca tctagcaaag acaacttctt tctaatctgt atacctttta 108360
ttttcttgtc ttaatgtatt agctagcatt tccagtatga tgttgaaagg cattggtgag 108420
aggcaacata cttgccttgt tcctgatctc agcaggaaat cttcaatttt atgttagctc 108480
tatggttttg tagatattct ttatttacat taaatatgtt agctgtatgg ttttgtatat 108540
attctttatc aggttcaggt agttcccctc ttttcctagt ttactgagag gcttttgaaa 108600
atcattaatc agtgttggat tttgtaaata ctttttttcc acctattgat attaccatat 108660 gattttctt tagcttatta acgaaatgga ttacattaat tgattttcaa attttgaact 108720
agactggcat acctggagca aatcccacat ggttgtgata cattatttat gaatgcattc 108780
atggtcatgg ttgctattag tctgtagtta tcttttattg taaagacttt ggtgttggta 108840
ttaaggtaat gctgccctca tagaataagt tatgaagtat tttctctgct tctgtcttaa 108900
ttgagattgt agagaattca tataatttct tccttaaaac tttggtagaa atcagaatga 108960
accatctgtg tctggtactt tgttttgaaa agttattgct gattcaattt ctttcataga 109020
tataggccta tttagattat tattttgcat aaatattggt agttgtgtcc ttcaaggaat 109080
tggtccattt caccttgatt attaaatgtg tgggcacatt tgttcataat atttctttat 109140
tatcctttgt ttttgagaca gggtctcact ctggttgccc aggctggagt gcagtagtat 109200
gatctcagct cactgcagcc ttgacttcct gggctcaagt gatttaccca cctcagcctc 109260
ccaagtagct cggactacag gcacatgcca ccatgcctgg ctaattttt tattattatt 109320 agagatggag ttttcctatg ttgcccagtg tggtcttgaa ctcctggact caagcaatct 109380
gcctgcctca gctccaaag agtgatggga ttgcaggcat gagccatcac acctagcctg 109440
atggcagaac ttttaggaa caatagaatg gtatatggca ttttcaaaaa ttgttttccc 109500
ctcctcctat ggaagcatga agggattttt ctctagtatt cattgtgaga acctcatctg 109560
```

```
gctcctgaat gtagaaaact cacaaaactg tgaggaacct attatgactg gatgcctttg    109620
gagttgttca cactgaacct ccagcaattc atcaattata tttcagattt tcctatccca    109680
acactggttc ctacagaggt ttctgctcca gtaagctgta attctttta tccatctgct    109740 tccttggttg tgagggcagt gatttcccct gtgacctcat ttctctgaca gatctaagta    109800
gtcttgatta catcttttaa cctgttgtag gtatattcag attttctatt tcttcttcag    109860
tcaattttag tagtttgtgt ttttctagaa gtttgttctc tagctctgct ttagctccat    109920
ccaataaaat atgagtatgt cgagttttca tttacaacaa ggtattttct aatttctatc    109980 atgtttttt gattcctgac tgtataggag tatatttta cctattaccc aaatttgctt    110040
gttattcatg tataatttta tcagaaaaca cactttgcac aattttgca gtgttacatt    110100 tatttagact tgttttataa cttgacatac agtccatcct ggagaatgtt tcacgtgtgc    110160
ttgagaagaa tgtgtatatt cagctgttgg tgggtggcat gttttataga tgtctgttag    110220
acctagttgg tttatagtgt tttttacaac ttctgtttc ttttaatct tctatctact    110280 tttagccatt attgaaagtg gattagtaaa ttatctattt attcctttaa ttctgccatt    110340
ttttgcttca tgtattttgg tgctctgttg cttattacat gtatgtttac atttgttaca    110400
tcattttaat ggcttgaact ttttattata aaatgtgtat atcttgtaga tatcgtatag    110460
ttaaatcttt ttaaaaattg atattgctag tctttgcctt ttaattttc aatttatata    110520 catttaacat aattattgat aaggtaggat ttgtctgcca ttttgtctgt atcttgtctt    110580
tttttgtgtt caatagatat tttctagtgt actgttttaa ttcccttgtc ttttactaaa    110640 tttttgatg ttcttaatgg tttccctggg gattacaact aacttataac agctagtctg    110700
aagtaatacc aatttcatta caatataagg aaactttgtt cccatatagc tacattccct    110760 cttttactc tgtgctatta tacaaattac attttatttt atgcccatta acacagatta    110820
tgttttttct tttaaatcag attgatattg tcatttaaat caaatatgag aaaaatagtt    110880 acaaaaaat acatatatga tttcatattt acctatgtaa ttatctttac tggtgctctt    110940
taagttctta ggtgtatttg aggtactgtc tagtgtcctt tcctttcagc ctgaagtata    111000
catttagtat ttttttgtagg acatgcctga aaacaataaa ctcttattta tcagagaatg    111060
tcctaattta ttatataata catttctgaa agatagtttt gcaaaataca gaattcttgg    111120
ttggcagtct ttttcttgtg gttctatgtc attctactgc cttctggtct tcattgtttc    111180
tgatcagaga tcagctatta atcttattgg gaatcctgca tacatgataa tcatacagtt    111240
ttcatgattt tcttgtgttg gcttcagca gtttggttat gatgtttata tgtatgcata    111300
tctttgggtt tatgttacat ggagttagtt gagcttcttg gacatgtaga ttgatgttgt    111360
tcatcaaatt tgagaagttt tcggccatta tttttcaaat attcttccta ttctttattc    111420
ttcatcctct actttgggga cctgcattat gtctatgttg gtatgcttta tggtcttcca    111480
cagatctctg aggttctgtt tatgttttca tttttcagac tgaataatct caattgactt    111540
atcttcaagt ccctttttcc cctccttttc aactctgcta ttgaacccct ctaatttta    111600 ctgcagttat tacactttca gctttagaat tctatttaat aatatctttt tcttgagttt    111660
atctcatgta tttaataaaa tgctgtagtc ttacttagt tatttaaata cagttttctt    111720 tcattattttg ggcatacatg aaatagctga cttaaagtct tgtccagtg gcctaacatc    111780 tggactttt caggaatagc ctctattgac tactttatag gggccatact tgtttctgt    111840 ttctcttaat tgtttagaca ttttaaacta atgtaatggc tgagagcagt ggctcgtgcc    111900
tgtaatccca gcacgttgag aggccaaagc aggagcatca cttaagccca ggagttcaag    111960
```

-continued

```
actagcctgg gcagcatagt gagaccctgt ctctacaaaa ataaaaataa ataaaataat  112020
ataatctggt aaatctgaaa atcagattct accccctgcc cagaatatgt tactgtttct  112080
ggtggttgtt gtttatttct ttttaactac tcctataaag tttgtattgt ttctcataga  112140
tagccatcga agtctttgct tggttaactt agaggtcagc taaggattag acagaattcc  112200
ttaggtgcct gagatcaata agtcagtctt tgacaaaggg gtctgtatgt gtgttggggc  112260
atgcattcaa cactcagcca ggctatttgc agctctggat tagcctttat tccctgcttg  112320
tgcagagtct caaggttaga ctgtggtgag agtttagggc tttctgaggt cttttgtggg  112380
ccctacagtt gcatgtggct ttctaaattc ccaggaatat attttcaaag cctcctgtgg  112440
atcatctcat ttcccaggta atttactttt aagctttttt agttatctta tgttttgctc  112500
cagttattag ctacacctga gtcagtgaca atattcaaca gctgcctatg attatttgac  112560
aaatgcctct gtggaaaagg tggttcacac taggtgaact ccaagttaga taaagtaaag  112620
ataaccttac tagtgggatc ttccaggaaa ctaccaaaca ggtcaaataa tgtaaggtct  112680
ctgtgaatgg gactttagag tatatccaac cagtctagag tatatccaac caatctggcc  112740
tcctctagtg gcagcctggc tgctgctttt cataataaat gtgggctgtt ttgatttgaa  112800
ggctaccata gagctgtggg gaaagttaaa ataccacaga gctcactctt ctcactgaaa  112860
tcctgtcttt ttttcccttg aacaaattct ccctatattg ctgcaagctt tttgctaatt  112920
tccagatctg aaaaagctga ttctgacaat atttatcagt acttttattg cttttatgga  112980
ggataaaatt ttcagagatc cttattctgc cattttgct gacatgtgta aagtgatcat  113040
ttctaattgt aaaattcctt ttgcatttat tagctggaat actttacagg acttttcctc  113100
atcaaccgtt agttaccatt taatatagtt tgtaagaatg atagaataaa tgcatggcaa  113160
gaatctttac ttctcaaatt tcagagattt tgatgggaaa ttatatttag agatcacaat  113220
cagtgtctag atgtgctccc tgctatggag gtgtcattac ttttaggctt ttttaatggg  113280
caaatacatg aagtaattat tttttagaaa gaaaatctga gattaactca aatcattaat  113340
tcatactgat ttttcctatt catagttgac agagtattat tatcttttgt tctgcttctc  113400
ttgtacactg aaattcttgg ttttttgatat taacaattat ttacttatat cacaatatac  113460
atacattaat ttaaaaataa tttacagtgc tacctgaata ttttttcttg taagttgttt  113520
tatctctctt tgcttacttg tatgtttgtt tattgtcatt agaatgtatc aaactagggc  113580
tataaagctg taatactata ttttagccag aaactaggac ctagcactca aatgcccatc  113640
aatggtagaa taattcatca cattttata agatggaata tggtactcaa tgaaaatgaa  113700
taaagtacaa ctacatgcag tgatttggat ggatatccca aacataatgg aaaaagcaca  113760
cacaaataag cttatattat ataattccat atacctatgt atatatcaag tataaaagta  113820
ggcaaaacaa gctactgatg gtggcacaca cctatagttc cagctatttg ggaggctgag  113880
gcgggaagat cacttgagcc cagaagttca ggttcaacct gagcaacata gcaagacccc  113940
atctgtaaaa aagaaagcat tattaacata aaaataggca gaactactat attcttagag  114000
aagttactgt tagggagaca gacagtgagt gactgaaagg caaaatgagg ggaaattcca  114060
ggggatagta aatattttgt ttcttagtgt gggttctact taactgggta ttttccattt  114120
gtaaactgta aaattatgtg cacttttctg tatgtgtatt acattgcaat aaaattgttt  114180
aaaagtcaat tgaaatagtt ctgtgtgtgg ttatgccaca gcttaataca gagttagatt  114240
agacttcttt tcaaactcat tttgcatata gacacctata atatcagctg cacagcctat  114300
```

```
ataatgctat ccatagcaat gaatttggtc ttttgatttt tcaggagaac ttgcgcctgt    114360
caggggctgg atccagaaac ctgtggtgcc tccttctctt ttggttgttc atggagcatg    114420
tactacaatg gatgtaagtt tgccagaagc aagatcccaa ggaagtttaa gctgcttggg    114480
gatgacccaa aagaggtttg tttacttcct gatgtataat cgctttattt ttcatagaga    114540
attcattagc ttagatgaag tgaacaatat gacatatctt ggtaagctct tattaatcaa    114600
agtttttccc aaactgtaga tacacactat tttttaagtt ggcataataa tcatattatg    114660
ccaaaataat agataaaatt tgagcaacaa aaacttcctc tttggtcttt tatgttaatt    114720
ccaaagtttt aaaggggtgt cacttcattg ttaaaactaa atgagaattg gtgatgtttt    114780
tcatattttg actctgaatt atggaagtta cataagtact acattcagaa aagaccattt    114840
ttagtcacat ttatgtgcaa tgagattcaa ataatttaaa gtcactgtaa tgaatgcatt    114900
taataaagtc actgtaatga atgcatttaa gtaactaaaa catttagatt ttaatataac    114960
tctgtaatgg aaataaatgg acactaattt ctcactgaag tcattggttt ttgtcttgtc    115020
tgtagaatac gtatttctta taatttgcaa attgataaat ttaacaactt ttgggtggca    115080
tgtagtctag agtatagata cttcttgact tatgaggaga ctacattcct ataaatccgt    115140
tgtaaaatga aaatccattt aatacccccca ataaacccat cctaaagtaa aaaaaaaacg    115200
aagccattat aggtcaggga ctgtctccgt actaattgaa tgatgagaaa acctcagtat    115260
atttagcatt tagctatgac cacattttca gtcattctat acacttacaa ttatcttttg    115320
aatttcgaat acaattaaaa tatttccata ctatagatat tataacattg atgagtccct    115380
ttaaatgaag aatttgttaa ccttattaag ctttcactta ctattatagt cacagttaat    115440
aaagcaagtg caaaaactcc tgaaatcaca gtataagttt tttaaaggat gttttcaata    115500
attaaagttt acttaaatgt gcgagacatc atttcataag acaagaatat gaatattaat    115560
aacttaatga aaagtactga ttttgcttgc tgtcatttta attttctaca gataactttt    115620 ttttttaacca ctgttttatc aagtgataaa tgtttatcac tttcacgagg tttcatgtaa    115680
accaaatcca gaggatacca agtaacttat tgcctctgtt gggtaggaga gctctgttca    115740
gaaacctcct caccttctaa aatttacatc tctgccaggt ggttatgtct cacaacttttt    115800 ttttttttaga gaaatatcaa tctgaaatga agacttctaa gtataaatgg agcagctaaa    115860
tatgatcacc taccattttt taacagtata ttacttggaa aatctgttct tcatgagcag    115920
ggcaggtggg ggtgtaactg agcatttccc ctttcaagta aattctgcaa aggttttcat    115980
gtatcctgca ttctagttct gaagcatttt atccatattt gaagtgtcca gtaaatttta    116040
gttgctctat ggagagatca ttccaaatta tttaaatact atctttataa acataaaatg    116100
taaagattag aaatagacaa attaagctaa agaagttctt ttaatagttc atcttccttg    116160
gtagctaaaa aatgtgacct ctttaagacc atacggctta attccctaa ccctactcct    116220 ggcacaggct tgtgtgtata aaatgcaaaa tatctgcatg cagttagaaa atcaatctta    116280
tgaaaaaaac aaatagctag atatttacta gcacatatga aattaaatga tagtcatgtt    116340
ttaaagatgc tttatttagt aataaaggca ccatatattg tgtttgggat tcaaaatgta    116400 agggaataa tctaactgat agtctctttt acatagagaa aatggactta gaatttaata    116460
tgtagaatta ttcactttat acaggaagag aaactggagt ctcatttgca aaacctgtcc    116520
actcttatgg caccaacata taagaaactt gcacctgatg catataataa tcaggtaagt    116580
ttaaataatc attggcagca attgtaacaa cttacttgtt actaatgacc tatgtccaaa    116640 aatattttg aaacaatgat ttttaaatat tattctaact tttcctctta attgttgaaa    116700
```

```
ccactgcagt gttcagtttc gagtatataa aaattatacc atacaaaagt acatttttt   116760
tgtcttttag ctgtaaagac atgcgcttct aaaagtcaca ggctgttcta tctactaatc   116820
ttgttctcat atgaataatt ttgtttctgt aaacagacta tggagattac atcaaaatta   116880
tgtggcccaa gctataggtt ctaactacct atttttactg caagtctata agtataaatg   116940
agtattcata agaatttata gacttacaaa tattcacata aagctatgca tatactaaca   117000
ttgtaagtat atatatttcg gtccagatgt gtcagatttt gctgatcttc ctttttgtt   117060
tgaccttgac ttcatacacc aagcaaaaac attttttttt tctattttac atgtgtattc   117120
taaactatag ctagttaaga caggtagatg atttggtcag aaatctctca tcatgaaggc   117180
aaaaaactaa aatcttcact gtttcagtaa catcaacaac aaaagcatta agtgaaagtc   117240
tattacaaac taaacactgt gtttagtcac tgggaacata aaggtgagca gtgccatctc   117300
tgtctgtctt taagaattcc gtctttgctg ggtacggtgg ctcacacctt taatcccaac   117360
actttgggag gccaaggcag gtggatcacc tgaggtcagg agttctagac cagcctgatc   117420
aacatggaga aaccctgtct ctactaaaaa tacaaaatta gctgggtgtg gtggcaggca   117480
cctgtaatcc cagctactcg gaaggctaag gcaggagaat agcttgaacc tgggaggtgg   117540
aggttgcagt gagccgaagt caaaccattg cactccagcc taggcaacaa gagcgaaact   117600
ccatctcaaa aaaaaaaaaa aattcatctt taactgggtg cggtagttta tgcctgtaat   117660
cccagctacc caggagacca ggagtctgag gctgcggtga gccatgattg catcactgtg   117720
ctccatcctg ggtgacaaag atgacccaga ttctaaaaaa aaagcaaaaa acaaagaat   117780
tccttcttta gtggagacag agacatataa aataaatagc aatttttagaa ttacacagtt   117840
ccagctggaa tagaagaatg tgcacatttc taaaaaaatt taaaaacaaa acccaaaagt   117900
agactagatg tcacaagcag ccttagacgc taaataaaga tctttgaact ttattctgta   117960
ggtaaccatt gggctgtttc aagtgtgtgt tggggatgga agggtaaagt gatgtaattc   118020
gtattttgaa aaatttactt aaaagccaag taagggaaat ataacttaaa tctatgtaag   118080
attagagaga gaagaaagct attgcaatca ttgggcaaga gattttaagg acctaaagaa   118140
atggcaggaa ttaagtatgt acactaacta aggtggagct tagagaactt ggtgactaga   118200
tgtatggatg agaaaagaat ttggagatac aacaaatttc cagtttggac aggtagttct   118260
attaactagt atcagaaatt ggtaagaaat agtaagtttt gggatgggga gaagatatca   118320
aaatttggga catgctaggc ttctaggtta attagatgga gaatcaggag aaaaattcag   118380
gctagcactg tagatttgag agtcagaatg ctggcaggac ttaaagttga atacatagga   118440
atgaaaggag gttttcaaag tagagattat aaagaggaca aagggctgat gatgggattc   118500
tggagccatc aatcatttta ggcatgagtg gaggaagaga agccaatgaa gtaagaactg   118560
ggggagggag tagaagaaat gtagtaggaa aagtgaaaga gggagatgga tggatggagg   118620
aaagctggaa tgatgagaag acacccagag cagagtatac aggagcaata ggtatggggc   118680
tctgggatgg gtgctctgtc atttacttga taatattaaa gactctcgtg ggattagatt   118740
agtttacaca gcagacatgg acaagggact aatcctaaaa tgatttagct actcttcttt   118800
tccactgtgg actttaacgt cccaaacatt ttttttttt tttggttcga acaatagagg   118860
caaattaaac gatggtctat ttgtaagtta ttttatgtca aattatgttt ttagaaatgt   118920
gtatgaatat ctatgaaaag ttttaaaca ctattaatag ttggattaat actgttattt   118980
tgtttagcta gtatcacaaa gtataaggag tgctttgata ctgtcgtaaa agtttaattc   119040
```

```
tcagcaagaa cttctgaaat aaatcaagct ataaaaataa ataaatgaat gagtctatgt 119100
tgctagattt aaagttgggt cattttctat taaatgaatt tttaataggt gctgttaatc 119160
aaatggcttt acttgaggca gaataacaaa gcattgatgt tcttttttgct cccttgattc 119220
ttattatgga ccgtctcata cttgaaacta ttttatacat ttcctaaaac ttaagtaccc 119280
aaaatatgaa gccatcaaat atgttcaagt tttaatattt atatatgaaa atgtgttgat 119340
gtaatgtcta gataaaattaa gtcaattaat agttgtaaat ggatgagatg cttctgaatg 119400
gataaaatat ttttatattg catggtaggt actattggta atattcatcc atgtatgtta 119460
atatgcttta gagatcaaaa taatagccat gtgatgtttc cacacagtac acggaagac 119520
catttgatgt tatagatgct gtcataaaac ctactatttg atctttacct cctttcccca 119580
actgagtgtc gtatctctat ttctcacatc tgaatattct tccttgcttt attccttgat 119640
ttcatgaagt cttattgcta aagtttagtt ggctctccac agcatctctt ctgtcagtcc 119700
catggaatta gagcttcagt tttctcaact taaatgtcct ttcttcgtgt ctatccagta 119760
gacatatatt tggctctgtc ttttctatgc ctgccttaca atttaacagt agacctgaaa 119820
tagcaggtgt caatctcaaa atcgtgtgct atttatcata catgaagatg acattttaga 119880
caaatgcttc taagagagct ttctatgaag atggaaatat tctctattta tgctgttcag 119940
tgtaataggc actagccaca tgtggttatt atttaacagt tgatacgtgg ctagtgtaat 120000
tgagtttaaa ttaatgtaaa aattaacaca acagccaca tgtggataat ggttaccata 120060
gtgaacagca caaccttaga ccatgagaaa gttatgcatt tagaattgtc ttccagacat 120120
ttagatggat ttccagtaat tcattcacaa aatcctgcat ggtattttt aggagatggc 120180
ataagtgtaa tttctagctg attgtatatc tgttttttgtt caagaaacag aataaagcta 120240
actagaccac agcatgaact gaacggccac aaagcacaca tctatgttaa agagtagttg 120300
gtaccttcat tttccttttgg ccaaagtttt atgaggttag atagacaaat acatatatga 120360
atccaacagt aaataatatg aagccaccac aaacttttat cctaatgcaa gttcatcttc 120420
tagccatgat ggagtaaaca gagactacat atgccgttac acatttaaga aaaaactgac 120480
aaaatatatg aaacaatggt ttttagacat agaataagaa attcaagaga cagtggcacc 120540
agagagaaag gaagtaaaaa ggtgaaccta taaatacccc agtttacttc ctgaagagag 120600
tattaggctc cagtgtagcc agtaggaacc caaacacacc cagccttatc tctgtattaa 120660
ggagacaaag ttcaaaattt ggagaggcca aggtgacgag agttcactat tcagaatatc 120720
agagaggaga gagtgttatt gagaaaagct ccagagacct gcagagggtt ctgatccagt 120780
cttcagctga gtattaaaca gcacatgcat gtgaaaaaac tgccaaggct aggtagggaa 120840
agaaccatca gaagaagcag gcagaataat cccttgatct cacacaggac ctggaatagt 120900
tcttgatcat accagccaga cggagaagac ttcataatac tattcataat tgtattgcct 120960
tggtagtaga agtaaatttg gcagttctga cctcatctaa aaatgcttaa aatgaaaaca 121020
tagaagggcc aaactgattc taagtaattt aactgcatca cagtacaaaa attaaaaaaa 121080
aaatctacca acaaggtaaa atttatagtc tagcattcca tcagaaaata caaggcatac 121140
aaagaaaaaa gaaatatataa cctttactgg ggaacaggca gaaatcaatc aataaaaata 121200
gtcccagaac tgacatatgt gatacaatat gtaaataagt tcattaaaat ggctatcata 121260
tttcatatgt taaatgccaa gaggaaagca tgagagtgat aaggaaagat cagaagatat 121320
taaaatacccc tacaatgacc ttctagaagt gaaaatatata tatctagatt aaaaatacac 121380
taggcggaat taacagatta aggaacttga agacatagta atagaaattt ttcagtataa 121440
```

```
agaaaaaact gaaaaaaatg aatatataaa agacctatta gccaatattg ttacactaat  121500
atatgtgtaa ttggagtacc agaaggaggt gggagacaga aaaatattta agaaacaat   121560 ggccaaattt ttttcagatt tgttcaaaac tgtgaaccca cagatctcag cagctcagca  121620
aaccccagat taaaaaacaa agacataaaa aaagactatc aaaaatttat aatcaacttg  121680
cttacaatct gtgataaaga gaaactcaga aaggcaaatg gagaaaaaag gacatattac  121740
actaggtggg aaaaaataag acaggagact tcattcagaa aaaggcaaga gagaagatgt  121800
aagagaaaca tctttaacat actaaaagaa aaaagactct ccacccagaa atatataacc  121860
aatgaaaaca actctcaaaa aagacagcaa aataaagaat attttttcag acatacatac  121920
aaaagctgaa agaattcacc accaacaaac tagcacttta aaaatgttaa acgaaatcct  121980
tcaggaagaa agaacatgat accagacaga aatccagatc aacataatga aatgaacagt  122040
atcaaaaata gtaaacatgg ttaaaagact tttaaaaaaa tgataacttg ctatcttaaa  122100
aatatattaa caatgtatta tgaggtttat aacacgtaga agtagcacag aggctgagga  122160
attgaaagta tattattgta aagtacttat acgatatgtg gactgggtat attacttggc  122220
tgtaaactgt gagacgttag agtacactgt gtaccttaaa ccactaaaaa aaaaaaaaaa  122280
agtatatagc taatcagcca gtaaagacag aaaaatgaaa tcaatccaaa aatgttttta  122340
aaaatatata ggaccaaaaa aagataaata taaaaataaa acaaatagca agatggttta  122400
tttaaaccca actgtatcaa caaccacatt aaatgtaaat ggttttaaca cccctaatta  122460
taaggcagag cttgtgatat tgaaaaaaaa gcaaaaacca agaaaccac tttaaatata  122520 aagatacaaa taaattaaaa agatatttt aacataaaaa atgatgttga aaagacataa  122580
caggaaaaaa tatgattatt gcagtaggta cagaaaaacc atttgataat attcaacatt  122640
cataaaagga aactttctca acctattaaa tacataaatg gaaagccaaa agctaatgct  122700
atacttagtg gtgaaagact aatacttgac ccctaagata aggaacaaga caacaatgtc  122760 cattttttaac caactgcttc tattcaacat caaactgtaa attttagaaa gtgcagtaag  122820
gcaataaata aagcagtcaa gattgggtag gaaaaaataa aactgtactt atttgcagat  122880 gacatgttg tctacataag aagtctcaaa aaatctacca gaaaatgaaa ttaatatatg  122940
aatttagcaa agttgtgaaa tacaaaattc aagtgtatt ttatatacta gcaataaata  123000
aatcaaaata aaccattaaa atagcatcaa aatataaaat tcttagacat acatttgaca  123060
aaaatgtata agattatata ctggaaacta aaacattgct gagataaatt atagaaaact  123120
tcagtaactg gagagataca ctatgttaat ggatcaaaag actaaatatt attaagatgt  123180
cagttctccc caaactaatc aatatgttca atacatgatg tttcaaaacc ccagcaggtt  123240
ttttgaaaga attggacaag atggctgtaa aatatatata cttggaaatg caaggactt   123300 ggaatagtca ataatatttt taaaataagg gcagaatttg agactatata ttgcatggtt  123360
ttcagattta ctgaaatcta taattgctac tgtctgtcaa gacagtttga tattgcccag  123420
gcgcagtggc tcacgcctgt aattccagca ctttcggagg ccgaggtggg tggatcactt  123480
gaggccagga gttttgagac cagcctggcc aacatggcaa aactctatct ctaataaaaa  123540
tacaaaaaat tactggggca tggtggcgcg tgcttatagt cccagctgct tgggaggttg  123600
aggcctgaga atcgcttgaa tccaggaggc agaggttgca gtgagcccag atcgtgccac  123660
tgcactccag cctgggtgac agagtgggac tctgtctcaa taaataaata aaattttaa   123720 aaagtttgat attgacatac ctacatacac accattatac acaagtggat cagaatagag  123780
```

```
aatccttaag tagacccaac atatataata tggtcaattg attttttaaca aagatgattc   123840 aattgggaag ggataaccat tttatccagt agtatctgaa cagttggaaa gccataaggg   123900
aaaaaaggta atcttgaccc ttaatttcac accatttata aaaattaact ccaaataaat   123960
ccatttatat gaaattctag aaaatgaaaa tctgtagtga tagattagta gttgtctgag   124020
aacaaagcag gaagcatgaa ttatacaggg gcatgaggaa attttttaaga gtaatgaata   124080 tgtactttat tttggttgtg acaaatatat atcaaaactc aaatagcata ctttatggcc   124140
tcaataacac tataaaataa aaattttacc atgtcaagat atttgctcta ttttgtgtca   124200
ttccattttg tttctggata tatatttaag ttcaaaacat ttttttaaag ttctaaatgg   124260
tctaaatact agtgagtttt cggtgtaaga gtaaaactaa ctactttcgc attcacacac   124320
acttttattt ttcagattga atatgaacac agagcaccag agtgccgtct gggtctgaag   124380
gaaggccgtc cattctcagg ggtcactgca tgtttggact tctgtgctca tgcccacaga   124440
gacttgcaca acatgcagaa tggcagcaca ttggtaagtt gggctgagga cagcttagca   124500
gctgttgagt ctgttctcac actgctaata aagacatatg caagactggg taatttataa   124560
aggaaagaga tttaattgac tcacagttcc acatggctgt ggaggcctca caatcatagc   124620
tgaaggcaaa tgaggagcaa agtcacatct tacatggcgg caggcaagag aacatgtgca   124680
ggggaactcc cctttataaa atcatcagat ctcatgagac ttactctcct gagaacagca   124740
tgggaaagat ctgcccccat gattcaatta cctcccactg ggtccttccc aaaacacatg   124800
ggaattttgg gagctacaat tcaagatgag atttaggtag ggacacagcc agaccatatc   124860
agcagcatct catgttgagg agcagaacac tggaatttag tagcattcgg ttagagtaat   124920
atgttgtctg caggtttcac tggacagcaa tattttcatg aatgaattcc tgttgcaaag   124980
tgacctgctt tggcataact agcactctca tgataggttg gcacattagt ttcctgtcaa   125040
ttgtgttgac aagcacatga gaatcatgga aatccttggt gttaatctaa accagtgact   125100
atgcattgcc agttacagtt aacttccagg aaaatctcaa aattcagtgc cagttacctg   125160
gtagattgta atcagttaag caaaaagcca aatacaagcc attcaccttla cagagagaga   125220 agcatattca ccttacagag agagaagcat aaatgagaaa cacatcatca ttgtcacagt   125280
aactgtggta acctattgta aaagattcac agtgcaaaag agcctgacta catattacag   125340
tgggtaaaat ggatcggtct tgtaattgga ggcagtggtg aggggaaaat agatacatgt   125400
tatatatata tatatatata tatatgttct ataccaacaa agggttcagg gtataatttt   125460
gcatgtaaag gggtgaccca gagtagagat aaagaacaaa atattctgtt gaaaaaacta   125520
tgaatcaatc aacctaatga attatcaaca tggatgtagg tgtagttgaa gaagatggtc   125580
agtgagaata tggaaacaga tatcaggaat taaagtcata ttctagggca gaaaagcatt   125640
catggaggta ttagatgata gctgaagtaa tttgaagaag ctggtgtgaa gttttttgttg   125700 agaagcagag aagatattaa tttaatgttc tagatcagag attggaaaac tcttctctat   125760
aaagggcaag atggtaaata ttttagggac tgcaggccac ataggatttc tgtcacattg   125820
tttggtgggg ttttttttgtt tattttgttt tttaaaaact ccttgaaaat gtaaaaacca   125880
ttcttagttt actggccata caaacacaag ctgtgaggca cattagccgt aggttctggt   125940
ttcctaactt ctgatccaga agaacaaaca caaggcctac caaccacccc aacatctaaa   126000
atcatcacta atcatgtact cagcacctgc tcattattag gaggctatgc tagtttctga   126060
aaagcagaag tagtaaatga taactggggc tatagtgcat cctaatataa ccatgtttca   126120
ttccaggaag gtgacagaga gtaagatgat gagaaggatg tttagaatca agaagaattt   126180
```

```
gcctctgata gagcatgggt tctgtgaagt aaaatggaaa ggagcactag ataagaactg  126240
aatagggtta aatatgtatg ggaaaagtaa caaggtgctc agagacatga atttgaagac  126300
ttctgtgcag aaagtgacag gctcattaat accatctcat gttgaagtta tttctaaagt  126360
cagtccattg tgatcacatt tctctcaaga atatcttcta attttatttt agatcacatt  126420
agatcacatt gtctccattg atcaaaaaca ctaaatacta aaagttagt atttaaaaac  126480 cacaaataat cttttaccaa agctagtgta attgtagtaa ctaaagcaaa aagtaccatt  126540
taattatcaa agcaacagag gtagcttttcc tccctccacc ccttacccctt ttcagagtac  126600 ccacttatat ggtcatattt cagaaaagaa atgaagaaaa gagaaagtta ggtttgacag  126660
agtacaaagg aggagagaca agagagtgaa aatagtatta agttgcatat tacctgtatc  126720
agccaaatct ttacctttttc attttttata ttttttacttc agttatctta tggaaatttc  126780
ttaaacagag agagttaggt gtcaggtatg tgaaaagaca tgaaatttgt gttcagaagt  126840
atgagatgag gcaaatgtga tactaccaaa aacagaggaa gtcatttcgt agaaaaaact  126900
tttagcctgt ttttgaagag gcttcacatc tagcacatct attttttgaag tgtgaaaagc  126960 aagagagtgc ttcatttttgg gggagtgttg cttcttccca tagacagaaa catatgtgaa  127020
gaacaagggt caccacagct aactgttcct gatagactca gagaaagggt gggtgggcaa  127080
tgtcaatttg tcttatctcc ctgtaccatt ttgttgctat tttcattaat aacaggtagg  127140
atggttttat ggtaatatat atgtcactga tctggatcaa ctaggccacc aacacaaatc  127200
tgaatactga gaggagaaag atacacacac acacacacgt tttctttggg acctgtagtt  127260
gaggctgtaa tgtcttactt ccctaccagg tatgcactct cactagagaa gacaatcgag  127320
aatttggagg aaaacctgag gatgagcagc ttcacgttct gcctttatac aaagtctctg  127380
acgtggatga gtttgggagt gtggaagctc aggaggagaa aaaacggagt ggtgccattc  127440
aggtactgag ttcttttcgg cgaaaagtca ggatgttagc agagccagtc aagacttgcc  127500
gacaaaggaa actagaagcc aagaaagctg cagctgaaaa gctttcctcc ctggagaaca  127560
gctcaaataa aaatgaaaag gaaaagtcag ccccatcacg tacaaaacaa actgaaaacg  127620
caagccaggc taaacagttg gcaggtaaat ttaatgtaaa gcatttgtag ataaatgtgt  127680
tgtgtggtat attaaaaatg aaaattattt tggttttgcc cccatcaact tgtaagttct  127740
ggggtacaca tgcaggatgt gcaggtttgt tatacaggta aacatgtgcc atggtgattt  127800
gctgcacaga tcaacccatt acctaggtat taagcccagc atcttcctga tgcacccctga  127860 ccaataggcg ccagtgtgtg ttgtccccac tcccccacca tgtgtccatg tgctcttatt  127920
gtaaaatgaa cattgttaat tttggaaagt tatatcaatc atggtcttag ttctgtgcca  127980
gagtcttctc taaagtagca agggccaggc tttgttctca gagatggtaa tgagatattg  128040
caccatcaac atggaaaaca tggaaaagtc tggattttat tctataataa acagcaactt  128100
tttttaacag gtaagtgata cgatgaaatt cattgtaatt tggcagtagg ccaaattagt  128160
agaggagcta atagtttgga gataaacaca gtaaaccaga actgaggtaa caagaccttg  128220
aattttgttg gttagtagca aagatatagc aaaatgatgc aaatgagctc ttccaaaatg  128280 ggaaaagaa aatacattgg tgacaaaaca ctggaatgaa agaagagaaa agtttaaaga  128340 tgacccccaaa gttttaaacc taaacttaac ctactgtttt aggtttctaa aacagtacta  128400
tttattgaaa taagtaagtt tgaaaatatg attgagagag agagagggga gaatgaaaca  128460
ttttccttta gacatgttga gtctgtggtt taggaggggt tctacatgta gattatgcta  128520
```

```
caaaactttt acccatcaaa atagattaca gctgtagtaa taacaataga acattattca   128580
tgaatactaa gttattgtct ttccatagcc tcctgcttta tgtctgcagt ttgtaaaaag   128640
aaaaaaaatc caaaatttgg gatggtattg gcctggccat taacaaaagc aaaccagttt   128700
gcttaaaact agccatcttt gctgcttcat gaagtcaaat ttctctactg attcatttcc   128760
aagctcagag gaactaagtt aaataattta gaatatgcta aagatgcttg ataagtgttt   128820
attgactggt tgacttaaca ctaagtaaat actgttcact taggttagct gtgaaatata   128880
attagataga accttgtctc tgctcccttt taactggctt ctgcaggtaa taatcccttc   128940
tgttctcaga actgccattg cagtttcatc tatttgttct taactcatat gacttttttaa  129000 agtgaggtca aaacagaagt atgactttta aaagtttcat ttacaaagct gaaagtttct   129060
ttaaagtgtt atctacaact gtgttaactt cctttctgga aagcctgctt ataaagtagc   129120
acttgttgat tatataagat gcttttttgtg tttaaatacg tgtcattctt ttttttcaca  129180
acattcccga atcttacata ataaatctta ttttaattat ttagcaaatt ccattgcatg   129240
ccaggcaatg aagaagtaag taaaataaaa catttttcctt cccatttagg aatttactta  129300
ccagtggggg tgaagagagg gctaaaaaca taactataat acattgtgag tattgcttta   129360
tcagatctat ctttgcagtt gagtattaca aaagcactag aagatgaggt caaagcggtc   129420
ccttgaggaa gggatgacta caccaaggaa ggatagggag agagggagga aaagggaggc   129480
acttcaagca gaggcatgtt cagaagttcc aaagaacatt ttgctctcaa tggaatggct   129540
ttggatgttt attacatttt ttttttcact aagttttgta tttctaatgc cttagacaaa   129600
aaattgtgct ggacaatgat cagaaccctg actttgctct tatctttgct taatgggtgt   129660
cgtatatcac tagtggagtt tcttacctac atttaagtat cctcactagc cttcataaaa   129720
taatcatcaa catcaaagat acctgtttct gttctctctt accctgtcca cagaactttt   129780
gcgactttca ggaccagtca tgcagcagtc ccagcagccc cagcctctac agaagcagcc   129840
accacagccc cagcagcagc agagaccccca gcagcagcag ccacatcacc ctcagacaga  129900
gtctgtcaac tcttattctg cttctggatc caccaatcca tacatgagac ggcccaatcc   129960
agttagtcct tatccaaact cttcacacac ttcagatatc tatggaagca ccagccctat   130020
gaacttctat tccacctcat ctcaagctgc aggttcatat ttgaattctt ctaatcccat   130080
gaacccttac cctgggcttt tgaatcagaa tacccaatat ccatcatatc aatgcaatgg   130140
aaacctatca gtggacaact gctccccata tctgggttcc tattctcccc agtctcagcc   130200
gatggatctg tataggtatc caagccaaga ccctctgtct aagctcagtc taccaccat    130260 ccatacactt taccagccaa ggtttggaaa tagccagagt tttacatcta aatacttagg   130320
ttatggaaac caaaatatgc agggagatgg tttcagcagt tgtaccatta gaccaaatgt   130380
acatcatgta gggaaattgc tccttatcc cactcatgag atggatggcc acttcatggg   130440
agccacctct agattaccac ccaatctgag caatccaaac atggactata aaatggtga   130500 acatcattca ccttctcaca taatccataa ctacagtgca gctccgggca tgttcaacag   130560
ctctcttcat gccctgcatc tccaaaacaa ggagaatgac atgctttccc acacagctaa   130620
tgggttatca aagatgcttc cagctcttaa ccatgataga actgcttgtg tccaaggagg   130680
cttacacaaa ttaagtgatg ctaatggtca ggaaaagcag ccattggcac tagtccaggg   130740
tgtggcttct ggtgcagagg acaacgatga ggtctggtca gacagcgagc agagctttct   130800
ggatcctgac attgggggag tggccgtggc tccaactcat gggtcaattc tcattgagtg   130860
tgcaaagcgt gagctgcatg ccacaacccc tttaaagaat cccaatagga atcaccccac   130920
```

```
caggatctcc ctcgtctttt accagcataa gagcatgaat gagccaaaac atggcttggc    130980
tctttgggaa gccaaaatgg ctgaaaaagc ccgtgagaaa gaggaagagt gtgaaaagta    131040
tggcccagac tatgtgcctc agaaatccca tggcaaaaaa gtgaacggg agcctgctga     131100 gccacatgaa acttcagagc ccacttacct gcgtttcatc aagtctcttg ccgaaaggac    131160
catgtccgtg accacagact ccacagtaac tacatctcca tatgccttca ctcgggtcac    131220
agggccttac aacagatata tatgatatca cccccttttg ttggttacct cacttgaaaa    131280
gaccacaacc aacctgtcag tagtatagtt ctcatgacgt gggcagtggg gaaaggtcac    131340
agtattcatg acaaatgtgg tgggaaaaac ctcagctcac cagcaacaaa agaggttatc    131400
ttaccatagc acttaatttt cactggctcc caagtggtca cagatggcat ctaggaaaag    131460
accaaagcat tctatgcaaa aagaaggtgg ggaagaaagt gttccgcaat ttacatttt     131520 aaacactggt tctattattg gacgagatga tatgtaaatg tgatccccc ccccgctta      131580 caactctaca catctgtgac cacttttaat aatatcaagt ttgcatagtc atggaacaca    131640
aatcaaacaa gtactgtagt attacagtga caggaatctt aaaataccat ctggtgctga    131700
atatatgatg tactgaaata ctggaattat ggctttttga aatgcagttt ttactgtaat    131760
cttaactttt atttatcaaa atagctacag gaaacatgaa tagcaggaaa acactgaatt    131820
tgtttggatg ttctaagaaa tggtgctaag aaaatggtgt ctttaatagc taaaaattta    131880
atgcctttat atcatcaaga tgctatcagt gtactccagt gcccttgaat aatagggta     131940 ccttttcatt caagttttta tcataattac ctattcttac acaagcttag ttttaaaat     132000 gtggacattt taaaggcctc tggattttgc tcatccagtg aagtccttgt aggacaataa    132060
acgtatatat gtacatatat acacaaacat gtatatgtgc acacacatgt atatgtaaa    132120 atattttaaa tggtgttta gaagcacttt gtctacctaa gctttgacaa cttgaacaat     132180
gctaaggtac tgagatgttt aaaaaacaag tttacttca ttttagaatg caagttgat      132240 tttttaagg aaacaaagaa agcttttaaa atattttgc ttttagccat gcatctgctg      132300
atgagcaatt gtgtccattt ttaacacagc cagttaaatc caccatgggg cttactggat    132360
tcaagggaat acgttagtcc acaaaacatg ttttctggtg ctcatctcac atgctatact    132420
gtaaaacagt tttatacaaa attgtatgac aagttcattg ctcaaaaatg tacagtttta    132480
agaattttct attaactgca ggtaataatt agctgcatgc tgcagactca acaaagctag    132540
ttcactgaag cctatgctat tttatggatc ataggctctt cagagaactg aatggcagtc    132600
tgcctttgtg ttgataatta tgtacattgt gacgttgtca tttcttagct taagtgtcct    132660
ctttaacaag aggattgagc agactgatgc ctgcataaga tgaataaaca gggttagttc    132720
catgtgaatc tgtcagttaa aaagaaacaa aaacaggcag ctggtttgct gtggtggttt    132780
taaatcatta atttgtataa agaagtgaaa gagttgtata gtaaattaaa ttgtaaacaa    132840
aactttttta atgcaatgct ttagtatttt agtactgtaa aaaaattaaa tatatacata    132900
tatatatata tatatatata tatatatatg agtttgaagc agaattcaca tcatgatggt    132960
gctactcagc ctgctacaaa tatatcataa tgtgagctaa gaattcatta aatgtttgag    133020
tgatgttcct acttgtcata tacctcaaca ctagtttggc aataggatat tgaactgaga    133080
gtgaaagcat tgtgtaccat cattttttc caagtccttt tttttattgt taaaaaaaa     133140 agcataccctt ttttcaatac ttgatttctt agcaagtata acttgaactt caaccttttt   133200
gttctaaaaa ttcagggata tttcagctca tgctctccct atgccaacat gtcacctgtg   133260
```

```
tttatgtaaa attgttgtag gttaataaat atattctttg tcagggattt aacccttttta   133320 ttttgaatcc cttctatttt acttgtacat gtgctgatgt aactaaaact aattttgtaa   133380
atctgttggc tctttttatt gtaaagaaaa gcattttaaa agtttgagga atcttttgac   133440
tgtttcaagc aggaaaaaaa aattacatga aaatagaatg cactgagttg ataaagggaa   133500
aaattgtaag gcaggagttt ggcaagtggc tgttggccag agacttactt gtaactctct   133560
aaatgaagtt tttttgatcc tgtaatcact gaaggtacat actccatgtg gacttccctt   133620
aaacaggcaa acacctacag gtatggtgtg caacagattg tacaattaca ttttggccta   133680
aatacatttt tgcttactag tatttaaaat aaattcttaa tcagaggagg cctttgggtt   133740
ttattggtca aatctttgta agctggcttt tgtcttttta aaaaatttct tgaatttgtg   133800
gttgtgtcca atttgcaaac atttccaaaa atgtttgctt tgcttacaaa ccacatgatt   133860
ttaatgtttt ttgtatacca taatatctag ccccaaacat ttgattacta catgtgcatt   133920
ggtgattttg atcatccatt cttaatattt gatttctgtg tcacctactg tcatttgtta   133980
aactgctggc caacaagaac aggaagtata gtttgggggg ttggggagag tttacataag   134040
gaagagaaga aattgagtgg catattgtaa atatcagatc tataattgta aatataaaac   134100
ctgcctcagt tagaatgaat ggaaagcaga tctacaattt gctaatatag gaatatcagg   134160
ttgactatat agccatactt gaaaatgctt ctgagtggtg tcaactttac ttgaatgaat   134220
ttttcatctt gattgacgca cagtgatgta cagttcactt ctgaagctag tggttaactt   134280
gtgtaggaaa cttttgcagt ttgacactaa gataacttct gtgtgcattt ttctatgctt   134340
ttttaaaaac tagtttcatt tcattttcat gagatgtttg gttataaga tctgaggatg   134400 gttataaata ctgtaagtat tgtaatgtta tgaatgcagg ttatttgaaa gctgtttatt   134460
attatatcat tcctgataat gctatgtgag tgttttttaat aaaatttata tttatttaat   134520
gcactctaag tgttgtcttc ctgaagtttt tttagtgctt gaatgactgc cacctcaatg   134580
aagaaaaggg aataaaaaat aattttttaaa gacactttta agatagatag ttagtcttat   134640
gttaaactat atctaagata atacccaaat aattaaggcc gaagtatttc tctggttaaa   134700
tggtgtagat attcactcac tttttccttcc aactaacttg ttagtgtatt cactttgcat   134760
gtgtagacag tgtaaatcag atagagagta aagcacctct aatcttagat tgcccctcc   134820 agtgttttgt gaagggtttc agtgatatag caggtgcact aaggttgaat tcatattgct   134880
tagaactaag gccaactctg ttttcagact ctcaccttcc acttcttgcc tactcttctt   134940
aagggaagat acttcttcct gtacatcaga aaggcagggt ggtaggctgg aggaatgggg   135000
agaggaggcc tggaaggtat cagacaaata tacttgtcct catctagtcc cacatggctt   135060
caaggagctt gaggctaaat catcctcatc tctacccatt ctctgccatg tgaatcatcc   135120
catatataat atcagtgcac tc                                           135142
```

<210> SEQ ID NO 2
<211> LENGTH: 20660
<212> TYPE: DNA
<213> ORGANISM: Homo sapiens

<400> SEQUENCE: 2

```
atttttagta gagacagggg tttcattatg ttagccagcc tggtctcgaa ctcctgactt       60
caagtgatcc gcctgcctcg acctcccaaa agttctagga ttacagacgt gagccaccgc      120
gcccggccca aagtgagatt tcaactctct ctacaccagc tggacctgac agcggactcg      180
cggaggcgca gacgccgccg gcggtcttag ctcaagaatg aagcagccgc actgggctaa     240
```

```
tgcgcctttg ggttcagccc ggcaggcgag ggaagcaaga gttcgctcag attggctttt      300
gggtttaagc taaagcgtca gaaactgaca tccaggttta catggggcat cctggagagg      360
gtcagcctcg caagcggctc tgctaatccc ccagccctga tcccgctcgc gggtcccggt      420
gggtctcacg cctgtagctc ctgcggagct gggctttcag cggcgcccag agaagcacca      480
gccgggcctg ccgccgggt cccggctccc gcgggacgct ggaggcgtcg gcggccctgg       540
ccccgcctcc tccccggcaa ggcccaatgg ggcggcaggc ccggcagccc cgccccggtg      600
gtgcccgcgc ggccagcgcc cgccaggccc agcgttagcc cgcggccagg cagccgggag      660
gagcggcgcg cgctcggacc tctcccgccc tgctcgttcg ctctccagct tgggatggcc      720
ggctacctgc gggtcgtgcg ctcgctctgc agagcctcag gctcgcggcc ggcctgggcg      780
ccggcggccc tgacagcccc cacctcgcaa gagcagccgc ggcgccactg tgagtgccgc      840
gcggagggtc caggcaggcg cgcgccccca gctgcgacgt ggcggcttcc caggctgggg      900
ccgggaagca cgtcccgcca gcccgcagcc cgggacggc ggggtcaggc gcacaaaggg       960
ccgcggggca gcttcgctcc gcgctccccc gcccggcgct tcccggccgt gccaggcgct     1020
ggggtgggga cttgagggac ggtggcaact ggtggcccgg gcgacggcca gctctgcgcg     1080
ggcgggggct cggggctgcc gcgcgcccct aggtatttcg ggagggggtc ctgagagtgt     1140 cccgacccg aagggtggcc tgccgcgcct gcgccctgg aacgagacga gcacccgtgg       1200
ggggctggag caccccgcgc gctcccctgg cgagagggag ggtcgtggct cggcccctgc     1260
tcagacaaag gctgggaggc gggagacatg cacttcccct ccttttcag ccaggcgcgc      1320 gctgatacca ggcccacgtc agctattttt ggagccttt acacgacagc tggaggagcg      1380 tccttttaa ttttccccctt ttgtttggcc gcccccaccc ccacccttc gccttcatcg       1440 ctgcacttga ggctccatcc tggggcctct ccttgacttg acctgccttg gcaggcacat     1500
gccctccctg cctggctcac tcgccgcaga gacctggcag cccgcgcaaa atgtcacttt     1560
gcggaatcgt tcccacggct tctgggtacc cttagttccc tgcttaggag ggaagacagt     1620
agtcgggtcg taataagcaa gacttagccc gagcctccgt tgccaacgca ggctgccttg     1680 cttgcgtgt gggcatcggc ctgccccctc accctggcta cccaacacag ctacaaaagg      1740
cagggaacaa tgtaggtccc ttggccctgc ctaatgcctg ttgccatgga aaccctatc      1800 ctaatctggc caggagcccc ttgcagtgag ccaggagagt gaggaagagg ggatggggcc     1860
cgctggccct gacctggcca gaggaggtaa tggttaaccg gattgtggga gcagctgact     1920
agagccgggg gggtagggag gcttgggccc cagtcctacc ttccctgcca aggagaaagg     1980
ggcatgtctg cttttgtacc tctgggaatc tacctcaggg atctgcccaa caactcccag     2040
gttccaagtg ccccaggacc caagattcc catatagcac accaccttca gcaaaaatat      2100
ggtggaagtt agccacattc tttaattctc ccttttttc tgccttgatg gtaaaaaaaa      2160 aaaaagaaa caacaaccc gaaaacaca cacaaacagg aacacaaagc gccttttaag        2220
ggtcctgaat ttggatacag aaaaagcagt cagttgcagg cccttctaga agtccccatg     2280
tgggttggtt atgaatgggg aaattgcttg gtgttggagt tggacatcag actctacagt     2340
tgcgactctg ccagcttgtt acctggcaac gcagctggac acagaatact tggcattccc     2400
cttgatgaca aggaaagaat attttgggc taaagagcc ccgtgtcttt gctgcctggt       2460
aattcctgca cgcatctttt cctatttgc aacgccatag gcttccagcg actgctggtg      2520
atgtttctgg taagttagag cttggggcag tgcggaccag ttctgtgaac ggctcagtgg     2580
```

-continued

```
cagaattact tatctagcct tccttcactc ctaacccaga aacttcttaa ttcttgcccc    2640
ttaagtgtgc agatctttct gccacgtcag ataaggccct agctgccctg ccagagctga    2700
ttggggtggt tgtgtttagg cctagtaggt actgaggaaa agcctctttg gaatggctga    2760
ggcctgctcc cacatcttct gtgtgaagtt gagggccctt gggctggttc cattcagggt    2820
atgaggtgct ggaaactgct ctcagattac tggaagccag ggtctgtggc cttccctggg    2880
gtttatactc tgtaaaccca tgttaaaaat accagcagat tgcaaatatt agtacactgt    2940
aggttgtaag cttcttcagg gcatggggcc tattgctgga gagagatgcc acccgtgtac    3000
atctggtgca ggctgctggt aagaactcac tggcccctgt gtggcaatgc ataccagatg    3060
ggtgagaggg gaggaaacac attcagtgaa acagaaggtg agggcagggc agccctgacc    3120
acagatggag ttgacttcaa cttgaccttt atttatgtct ttgacaaaag tagtatactc    3180
ctactttgtg ccagacacca tgccgggtgc tggggataga gctgggaata aaccagcag    3240 agactctttc aaaacccctta ggagctcaaa ttctgatgtg ggaggggca gacagtaagc    3300 aagatagatg ttgactagta tgatatatgg gtacaagagc taaggaaggc caggcactgt    3360
ggcttacacc tgtaatccca gaattttggg gggctgaggt gggaggattg cttgaggctg    3420
ggagctccag accagcctgg gcaatatagt gagaccccat ctctacaaaa ataaaaaata    3480
aaattagcca ggcacgatgg tgcatgtctg tggtcttagc tactcaggag gatcatttga    3540
gcccaggagg tcaaggctgc agtgaggtac aattgtgcca ctgcactcta gcctgggtga    3600
caaagcaaga ccctgcctcc cccttctccc cccaaaaaga aagagctaa ggagaaacag    3660 gcaagaaagg tgtgtgcaca aaagtttgta tagggcagcc agaaaagtcc tcactgaagg    3720
aatcgctgag gaggggagga agcaggccat tttcggtatt gggggaagag ggactcgcag    3780
gtgccaaggg catgatggaa gagcagagag gatggtgcga aggctggctc agcaggcacc    3840
aggtggagtg acaggatgag gttcggcagt ggggtctgta gagggctcac aggccatttt    3900
tgagagcttt cgcttttact ttgcagggtt ttgagaggag tatcgttacc tgatttccat    3960
cttatcggga gcattctagc ttcagggacc tggcaagaga ggatgatggc ttggacctgg    4020
gtggtggcgc tggggatggt gaagaagtgg ttggattctg gatatatttt gaaggaggag    4080
ccagtagtgg ggaaaggttc caattcaggc gattttacat aaaaatctag atacgcagca    4140
ggcactcact tatggcaagg gtgggcttgt ctgagggtgg cttctggttt tggtggtttg    4200
gatgtgagag aagggaagga atgaaggatg acaccaagga gtctactaga gtttgttcca    4260
aaatggctgt tctggccgcg tgcggtggct cccaggactt tgggaggccg aagcaggcgg    4320
atcagttggg gccaggagtt cgagacctgc ctggccacca tggtgaaacc cggtctctac    4380
taaaaataca aaaattagct gggtgtggtg gcaggcgcct gtagtcccag ctactcaggg    4440
gctgaggcag gagaattgcc tgaacccagg aggtggagct tgcagtgagc cgagatcacg    4500
ccactgccct ccagtgtagg cgacagagtg agactctgtc tcaatacata catacataca    4560
tacatacata catgcatgca tacatacata catacataca taaaatatac aaagttgctg    4620
tcctgccttc ttgagccccc aggaattgga acctttcccc actctctgat cttttgctgg    4680
gacatgctga ctgagcagcc tttctgctga gagcatgggt aggaatgtgg agggagcagt    4740
tatgcctggg gctggctgcc tgcggctgga cctctagcct cctgctggga gcagcaagaa    4800 gccagggat tgttttgaaa tccttacttg gtattgggtg ctaggagccc cagacaggga    4860
ggagagtcag cctaacgtgc ctctggtgac tggtgtaatt ccatcctgca ctctcgccaa    4920
gaggacagtg tttgtgcaat gcatcagctg aagattcgtg gtggctgtca cttcggaggt    4980
```

```
tttcagggag gcctagctgc tgctctgtgt atttcaggta gcttgtcacc acttatctct   5040
cagagaaggg cagaccatgg ctgtatctcc accatacagg ctgaacagca gacagggtc    5100 tcaaactcca gtgccctggg ccacactgga gggcacttgg ctgtcatgga gtgaagggag   5160
aggccgcctt cagcccagcc catccttgcc atgagtgagt gcctgctgca tttctagatt   5220
tttatataaa atctcctgat ttttttgac tggtttaaat ttttattatt ttggtaaaaa    5280
acgtataaaa cttaccatct tagtcattgt tcagtgtaca gtattgttaa gtacattcgc   5340
actgttgtgc agacattacc accatccatc accagaactt tgtcaccttg caaaaccgaa   5400
actctctacc catgaaacaa tacctcccca cttcccgtcc ccagtccctg gcagccacct   5460
ttttactttc tgtttctatg aatttgacta ttctaggtac ctcatgtaag tagaagcata   5520
tagtatttgt cttttgtgac tggtttattt cacttagtta gcataatgcc ccccaggttc   5580
atccactttg tagcaggtgt cagaatttcc cttcttttca aggctgaatc atattccatt   5640
gtatgtagat aacagtagtc cccttatcc ttggaggatg catttcaaga tccccagtgg    5700
atacctgaaa ctgcaaagcc tgtagatact atgttttttt cctatacata cagatctatg   5760
ataaagttta atttatgaat taggaacagt aagagattag caataataac tagtaataaa   5820
atagaacaat tataacaata tactgtaatg aaagttacat gaatgtgatc tcttaaaata   5880
tcttactgta ctgtactcac ctattttcag actatggttg actgtgggta actgacacca   5940
caggtaactg acgtcatgga aataaaacct ttgataaggg gggactgtat cacattgtct   6000
ttatccattc atctgtgatg acacgtgggg ttgcttctat cttttgctgt tgtgaacatt   6060
gctgctatga atgtgggcat acatatatct ctttcagacc ccgctttcga tattttggga   6120
tgtatataca gaagcagaat tgctggatca tatagtaatt cttgtccttt tcttttcttt   6180 tttttttcg agacggagtc ttgctctctt tcgcccatgc tggagtgcag tggcgcgatc    6240
tcagctcact gcaagctccg cctcccgggt tcatgccatt ctcctgcctc agcctcccca   6300
gtagctggga ctacaggcgc ctgccaccac gcctggctaa ttttttgtat ttttagtaga   6360
gtcagggttt cactgtgtta gccaggatgg tctcgatctt ctgacctcgt gatccacccg   6420
cctcagcctt ccacagtgct gggattacag gtgcgagcca ccgtgcccgg cagtaattct   6480 tttccttttta gctaaggaac acccatactg ttttccacag cagctgcacc atttcacatt   6540
cccaccaaca gggcacaaga gttccaattt ctccacatcc ttgctagcac tttattttct   6600
gttttgtttt tcttttcctg atagtagctc tcttagtggt tgtgagggga tagtggggtg   6660
atatctcatt atggttttga tttgcatttc cctgatgatt agtgatgttg agcatctttt   6720
catgtgcttg ttggccattt gtatatcatc tttggacttg aaatgtctat ttaagtcttt   6780
tgtccattat atttatttat ttattttgag atggagtctt cctgttaccc aggctggagt   6840
gcagtggcat gatctctgct cactgcaacc tccacctcct gggttcaagc aattctcctg   6900
cctcagcctc ccaaatagct gggactacag gtgtgtgtca ccacaccagg ctaattttt    6960 ttctattttt agtagacaca gagtttcacc attgtggcca ggctggtctc gaactcctga   7020
cctcaagtga tctgccctct tcagccttcc aaagtgctgg gattacaggc atgagccacg   7080
gtgcccagcc agtcttctgt ccattttaac gttgagttat ttgttttatt gttgagattt   7140
actgattttt aaaacttggt caccaattaa gatttttta aaaaccagt acctggaaca     7200 agcagaacaa gtctctgctg gccttggctc atgttgctgt tctcagttcc ctgggatgt    7260 ttgcttccag ggaggcctgg gcactcctga ctttggtgac agccctgctt gctctctctc   7320
```

-continued

```
tgttacctgt aggtttcccc ttccacattc actgcctccg ggcaggcact gttgtgtttt    7380
aggcatttca gtatcccagt ggggtactgg ataagtgctt agttagcacc tgccggtgag    7440
taaataatca ggtcctgtgg tctctgaggg tttgacacat caggtctttg atcttgacct    7500
tgaactctcc tagccatgcc tgcctgaagc ccaaccgtgg agcccaggct gaggctgaaa    7560
cctgaagaac tggccccaag tgagtctctc cttagggctc ctgattatga tagttcattt    7620
tttttttttt ttaacaaatt tgattagctg tcctcaaatt aactcatagg agatgctccc    7680
cagaactaaa ctagctctgc aacagctcaa cagactttcc gcaggttctg cagctctttc    7740
cactcaagct tcagaaaaaa gtgaaggaat attgtagatt gggttcaaaa tccccatcgc    7800
gtcttgggaa aggcagtaga gccagcagcc agccacccttt tgttctctag ggaatggaat    7860
agtccaaggc tgtgtttgtg ttctgcttct ctacatctga cccacgggtc ttccagaggc    7920
tgcatttggg tcagggacct gggctctatc ttgcctctga tgcagaccac actctctgag    7980
tctcattatt cccctaaat gatctctaag attattttta gattaaaaaa aaaaaacaaa    8040
ctctttgcat atctttggaa agtcagttgt ttgaggtctg ttaggcttta atcacttttg    8100
ttttaaatgt gccgaggtgg tttctaggcc tgcttttcac aggtattctg tcccttgtca    8160
gttcttccca cccagttttt tttgtttgtt tgtttgtttt tttgagatgg agtctcgttc    8220
tgttgcccag gctggagtgc agtgccgtga tcttggctta ctgcaaccte cacctcccgg    8280 gttcaagcga ttctcctgcc tcagcctcct cggtagctgg gattataggc acgtgccacc    8340
atgcctaatt tttctatttt tagtagagat ggggtttcac catgttggcc aggctggtct    8400
tgaactcctt accttgagtg atccacctgc ctcagcctcc caaagtgcta ggattacagg    8460
catgagccat tacacccagc cccaacccag tgtttttcaaa taatcattct cttcccttca    8520
cctgatttgc tgtgtctaat ctagagtgga gctgaagaca catcaccacc tctctaagga    8580
ctgtgtgtaa cacaagagta attgggctgt aagtgaggct gaggagtgct gctttgagga    8640
aagggcacag ctctcagctg agctggtgag atttccctgt gactgaagtt ttattagatc    8700
ttgttccctg ctctgcattt gctgcttctt cccaggctgt gggcagagga gcaggctggt    8760
gccccggtgc ccctatctgc tgcaggctga ggttcaacaa gccttgtcca aggcagctgt    8820
actgattcat tgttaggtgg ccagttcctg agttttcttt gaaattcact tcccagactg    8880
ttgggtattc ctgcgagtca gactctcctt cagtagcgtc ccctgccccc taccctccac    8940
tggtctccct ggacctctga tcagcccctc attgagtcct ttgatgcttc tctggtagga    9000
ctgacccacc tgcgtcggct gggatcaagg gttctgagtt ccattcgcag gtgctgtaag    9060
cctgtccttc ctgttgaata gggtcagagt cctcgtgact ctgctgtttt caagctctgt    9120
aaccttgggc agtaagctgt taacctctct gagcctcagt ttcccacact taaaatggag    9180
ataatggcca ggcgtggtgg ctcacgcctg taatcccagc actttgggag gccaaagtgg    9240
gtggatcacc tgaggctagg agttcgagac cagcctggcc aacatggcaa acccccgtct    9300
ctactaaaaa tacaaaaatt agccgggcct ggtggcgtgt gcctgtaatc ccagctactc    9360
aggaagctga gacagcagaa tcgcttgaac ccgggaggca gaggttgcag tgagccgaga    9420
tcacgccatt gcattccagc ctgggtgaca gaccaaagac tctgtctcaa aaataaata    9480 aataaataaa taaattaatt aattaaataa aatggaggta atgatacctc cttggggttg    9540
tttttgggat taaatggaat cacattgtac agcattggta cactgtaagg cacatagtag    9600
gcactcaata cctatctata ctatttcctt tatcaccaca agttagttga gggctcttgg    9660
gttgcacgca acagacaaag ttagtgactg gttaacttgg agaggatttt attatgagct    9720
```

```
acacagcgta gctcatagaa ttgcagggaa aactataaag aactaagtct tggacaaaag    9780
taatatcttg gcatgggcct gtagccccag ctactaagga ggctgaggtg caaggattgc    9840
ttgagccccg gagtctgagc ctggcttggg caacagagag agataaagag accctgactc    9900
taaacaataa gtaaatacat aaaagaggac ccaggccctc cttaggaact ggatggcagg    9960
agcccctgga caacctctta ctgatttggt gctggatgag gcagccgcag ctagccagtg   10020
ttctttgtgt tgatctcctc tgccttcata ttccagggggg agagggtctg acaggccaga   10080
ctggccccca ccctcttggc cactggtggg ctgggcatgt ttttgggtag ttctacctag   10140
ccagattaaa gtggggggtgg ggtggggagt ccagccagcc tgggcaacag ggcaagactc   10200
catctctaca aaaaaatttt aaaattaggc tggcacggtg gctcacgcct gtaatcccag   10260
cactttgcgg gggtcaaggc aggtggatca cttgaggtca ggagtttgag accagcctgg   10320
ccaacatggt gaaaccctgt ctctactaaa aatacaaaaa attagccagg tgttgtggtg   10380
cacacctgaa atccccgcta cttgggaggc tgaggcccga gaatcacttg aactcggag    10440 gcggaggttg cagtgggctg agatcatgcc actgcactcc caccctgggg gacaatagcg   10500
aaacttcgtc tcagaaaaaa aaaaaattaa aaatagctgg gtgtggtggc atgcgcctgt   10560
agtcccagct acttgggagg ctgaggtcag aggatcactt gaagccagga agtcaatgct   10620
gcagtaagct atgatggcat cagtgcattc cagcctgacc aatggaacag gaccctgcca   10680
agaaagagag agagaaaggg aggaaggaac gaaaggaagg aaggaaggaa agaaaggaaa   10740
ggaaggaaag aaaggaaagg aagtaagtaa ggatggatgg atccaggtgc tctaaaccag   10800
cagttcccaa agtttttggc accaggggcc agtttcatgg aagacaattt ttccacgggt   10860
ggcagggtgg tgggcagcgg ggatggtttt gggatgagtc aagtgcatta catttattgt   10920
gcactttatt tctattatta ttacattgta atatataatg aaaaaattat atagctcacc   10980
ataatgtaca atcgggggggt cctgagcttg ctttcctgca actagacagt cccatctgga   11040
ggtgctggaa gacagtgaca gatcatcagg cattagattc tcataaggag tatgcaacct   11100
agatccctcg tgtgcgcagt tcccaggcat gagctcaggt ggtagtagtg ctcactcacc   11160
tgcagctctc ctcctgctgt gtggcccagt tcccaacagt ccgtggacct gcactaaagg   11220
ctgtggcctg gtctgctgac ctctctccag agcccacggt actagtccat ggcctgggag   11280
ttggggaccc ctgctctaag cagtgaggga gctgatttgc agacggggga gtggacaccg   11340
ggcagctgga gccctggctt tctgccactg tctcctggtg aagggcgggc ctggctggga   11400
ggagagggcc cccctccagc ctccccaggg gcatgatgcg ctgtgtgtcc ctgcttctag   11460
atgccgacaa aaggatcaag gtggcgaagc ccgtggtgga gatggatggt gatgagatga   11520
cccgtattat ctggcagttc atcaaggaga aggtagtgcc ccctcctgaa gtgggtggct   11580
ctccaggtgg gctggccagg gattgttctg tcccacaggg tcttctggac tgcaggtccc   11640
taggaccccc ccgttgtcct ggtaggcagc agcagctctg tttctctccc tctgtctacc   11700
cttctttcac atctggtcca ctaattgttc agaagtcgtc aggcggggggc ctgtcccag    11760 cagtccgtgt tgtgatggtg ccagatccca cacgttctgt caactttgag aagcttcaag   11820
gttaatcctg tatcatttcc atcttgatcc cctacgtttt gcctcacttc ttgaaaagga   11880
gtgaaaaggg aacagggctg gtgtgtaggg cagtgaccca gcctgcagtt gtgacgagcc   11940
accatggcaa aggggtccca gagtggccgc ttggcttctc caaagttgcc gtggtctatg   12000
tatgtccagg agagcatgta gtccttgtga aggccccaca ctgtgtgtgc gttcatggga   12060
```

```
caaaggttga gaactgtcac ttccaactgt aagatctcaa agcacttgag aagaggaaac   12120
cagttgtata gagaaatcta gatgtacttg gggttggggt ttggctgagt tgatgggcca   12180
tgtgaggggg gcacacaggc acagtggagg aagaaccctc caaaagactg cggcctggcc   12240
tgccaacctc tctccaaagc cccagcctct gccagtctg gccaggcccc actgagaaat    12300
ggctgactcc agctttctgc tgcgcccctc cactggcctt cactcatccc tgttttgact   12360
gactgtcccc tgccatggcc tgcagacttc ttatcctgcc ctttgttgtc atgtccctga   12420
gtcactgggg tgacgccttg ctctggccct ctgtccccag ctcatcctgc cccacgtgga   12480
catccagcta aagtattttg acctcgggct cccaaaccgt gaccagactg atgaccaggt   12540
caccattgac tctgcactgg ccacccagaa gtacagtgtg gctgtcaagt gtgccaccat   12600
cacccctgat gaggcccgtg tggaaggtgc gagggtgtgg aggtgggcgg gccagggagg   12660
gtcacaggct tctcccaccg gcctctccag acttggggtg gggcagttgg ccatgtcact   12720
catctcggga ctgggaggtt gggaggctcc agagctgggg cttctcctgag gccaactgca  12780
cctgaggcca gtctccctgt gtgtgcctgg tggacagtgg ggcctcagag gtcacctttg   12840
atgaggctgg ggcaggcgtg ggtaaggggc tggcctcagg ttccacggtt agggcacagc   12900
agagctgaga acagaatcca tgtcttccat ctcccaggcc agtggtgttt ctgcttcact   12960
ctggctctga cagtggtagg tgtcatcggt gacagggctg aggaggagga ggaggaggaa   13020
ggtaatgctg atgtggtcac agtaaggatg gcttctttgg gcagtagtcc attctggcgt   13080
ggacagtctt gcaggcaggt atgcagagag attgtgcaga ggagtgctgt gtgtaaggcc   13140
tgtgtccttc agagcctcag cagcctctgg ggaacattgc tgttgccctc ctgccactgg   13200
cttggccttg caggtctgcc tctgtcccca tggtcatgca gggtcactga gaggtgcccc   13260
caccaggcct agactggctt ctggtccttg gctgttgggg ccgctctcga gggttccatg   13320
aagtcacagc agtgtgtgtg cagaggggcc aggtttggat aattcgagaa aggatggttg   13380
aggagttttc tgagctctct cttcctactt tccacagttg gagggagctg gcggaaagta   13440
ctcgagatac atctgcaaat tccccaggcc tgccctgtc ctgcaggtca tgcctgaccc    13500
acagcactgg gatcatttga gtgttgagct cttcatttca cctgaacctt gggagttgtg   13560
tatccccatt tatggacaag gcaggagagg gtcacagcct taggaactgg ggtggcgttg   13620
gggccaggac cggagcatgt ggagtgggca gtgtgttgtc aggcttcgtc agacaagtcc   13680
ttcccccgga ctgtactccc tccatgtgtg atgtgggaat cataatggcc aacagagcac   13740
ttagcatgga ccgggcaccg ttctaggccc tttacacacg agctcatttc gtcctcacga   13800
caacacttag gctggttatt ttttccagtaa ttttttttta cagctttggt tgagccactt   13860
ttgtaagcct caccattaaa actggcagac ttgctgggca tggtggctca cacctgtaat   13920
cccagcactt tgggaagccg aggcgggtgg atcacctgag gttgggaggt cgagaccagc   13980
ctgaccaaca tggagaaacc ccatctctcc taaaaataca aaattagctt ggtgtggtgt   14040
cacatgcctg taattccagc tgctcgggag gctgaggcag gagaaccgct tgaacccagg   14100
aggcagaggt tgtggtgagc cgagatcgcg ccattgcact ccagcctggg caataggagc   14160
aaaactctgt ctcaaaaaaa aaaaaaaaa aaaaaaatt ggcagactcc agagcccaca    14220
catttgcact ctagactcta ctgccttcct catgaagaat tttaggaccc ccgtctggct   14280
gtgttgttgc ttggggttca aattctggtt gaaagatggc ggctgcagtg ggaccactat   14340
tatctctgtc ctcacagagt tcaagctgaa gaagatgtgt aaaagtccca atggaactat   14400
ccggaacatc ctgggggga ctgtcttccg ggagcccatc atctgcaaaa acatcccacg    14460
```

```
cctagtccct ggctggacca agcccatcac cattggcagg cacgcccatg gcgaccaggt    14520
aggccagggt ggagagggga tccactgacc tgggcacccc ccgactggag ctcctcgcct    14580
agccatcctc ttgtctctgc agtacaaggc cacagacttt gtggcagacc gggccggcac    14640
tttcaaaatg gtcttcaccc caaaagatgg cagtggtgtc aaggagtggg aagtgtacaa    14700
cttccccgca ggcggcgtgg gcatgggcat gtacaacacc gacgaggtga ggctggcttg    14760
ggcatcctgg gcccctcctc tcccagcttg tctcttcatc tctgtctcgt ggctttcctt    14820
tcttctgtaa tggcctcatt cttaggccac aaagaggcag aaatggccac cagggctggg    14880
catggtggct gacacttgta atcccggcat tttgggaggc caaggcagga ttgcttgaga    14940
ccagaagttt gagaccagcc tgggcaacag tgagacccca tctcttgaaa caaaagaaa    15000 agaaaagaaa agaaaagaaa tggccacgag cagctccagg cgtactcctg cctgcttggc    15060
taccctatca gaagagaatg cctctttatc cccagttcca gctccaatgc caggctgagt    15120
cacatgacca cctctgagcc aatcacagag gccctgggga gaaaggcttc tgattggata    15180
agccagggac acactgtcaa ccccagcgct aggcctggga attagccctg ccccagccac    15240
atgtagtcta aggcggtgct ttccaaaaaa aagttgtttc caaaaaaaaa aaaaaaaagg    15300
cggtgttttc caaaaaaaaa aaaaaggcgg tgttttacaa agcaaagttg agagggagag    15360
gctgggccag cagaaacatc gtgtgcactg cacggaggct ggtgttaaac agtcgcgtgg    15420 gcggcgggt accgttcctg gagagctggg ccttgccctg ggaggtggga ggttgccggc    15480
aatcgccagg ctagggcacc acgccagggc cctgtctctc cccctgcagt ccatctcagg    15540
ttttgcgcac agctgcttcc agtatgccat ccagaagaaa tggccgctgt acatgagcac    15600
caagaacacc atactgaaag cctacgatgg gcgtttcaag gacatcttcc aggagatctt    15660
tgacaagtaa agcctcatcc atgtactctg tggcctttct tcccttcccc ccatgctgtt    15720
cccatcctac cctgggaagg tcgctattag agtgcatttg gctcagctcc gaggctcagg    15780
gagggatccc caacctgtca gccttctgcc ctctccccat aacagaccct tttactccca    15840
ggcactataa gaccgacttc gacaagaata agatctggta tgagcaccgg ctcattgatg    15900
acatggtggc tcaggtcctc aagtcttcgg gtggctttgt gtgggcctgc aagaactatg    15960
acggagatgt gcagtcagac atcctggccc agggtacgct gggaggacgc tgctccctgt    16020
gggggtggac tgttggtctt ctctggctgg agggattttc agacccttt ggtagaaaac    16080 tctagtggag caggactcat tgcagggtcc tctgtggaca gcaggggca ggagctccct    16140 ggcatctgag tgagagagga tcacaaatta ggtttggact ggtgtatgac tgaggctgct    16200
cttagagaga aaggagggca caggaattcc agggctaggt tgacagccct aaggttgctc    16260
cagtccatga tggagcctca tgactctttg gttccagtag gaaaatggga tcaagcggga    16320
ctggaggttc tttaaactac agcgaatgca ttttgcatag tgaacctaat ggatggaaga    16380
gaatgttggg gaagcctgca aaccccccaag ccctaggtg tcctaaaaga caaatcagat    16440
tgcagtaaaa agtataggtg atgaggtcag gagtttgaga ccagcgtggc caacatgacg    16500 aaacccccgtc tctactaaaa atgcaaaaaa atttagctgg gcatggaggc gggcacagtc    16560
atggacacct gtaatcccag ctacttgaga ggctgaggca ggagaatctc ttgaacccag    16620
gaggtggagg ttgcagtgag ccgagattgc gccattgcac tccagcctgg gcaacaaggg    16680
tgaaactccg tctccaaaaa aaataaaaaa taaaaaataa agtataggtg agaccattag    16740
agaagaacag cgagaaatgg gccaattgtg ttgggaacaa gagcaggaaa ggtggtaggt    16800
```

```
gtgggaaaca ggcaggacat agagagtgaa agagaaacct aagcttacca gggcagctcc    16860
tggtatgggg aaaagggaag cccaggacgg gttctgatga aaagcagagt cttgttactt    16920
tgtgtaaacc tttggcttta ctttggaaag ttcagtgggg atcctctcac cgaacaattc    16980
ccatctagga tagaaggatg aaacgccata gcagatgagg cagaggcatg aaaatgaacc    17040
ttaagtgtct aaggaatggt gtgaaggtgc aggtaaaatg gagaagggat tgcttacagc    17100
caaaattctt agaattcata gacaaagcat tttcctgtag atgttgtcca tgttttcttt    17160
cttcaatcct tattttggtg tcatggggt gcctttgaag ccctggagtc cttgacaata     17220
gaaaagcttg ctggagttga catgtggatt tgggagcatt cagaaattaa tcaaaaagct    17280
tgaaagtggc ctaagagagt agctgcaaaa gtgattgttg ggaaatagct gaccacagct    17340
ttattgtttt ccttgaatgt gcctccgggt cacgagccag gctgggtggc aggctgtggg    17400
ggaccacagg actctgtggc ctcttgggcc ctgtgggcca caggctgtgg ggcgcctgga    17460
gctggtgaca cagatggatg ttaatgtgct ggtgatagcc accctccagt gccctccagc    17520
cctgtgctgg gccctggaga cccacaggag ggtgaagaga cctggaacag tccctgtcct    17580
cccagttgca gctgggggag gctgagtaga gccacgaact atggcagcta caatattggg    17640
ttgtagaggg cagcagggct cagctgggtg gccccaggag aggcgaggcc ctgagagaaa    17700
ggctttctac cctccaggct ttggctccct tggcctgatg acgtccgtcc tggtctgccc    17760
tgatgggaag acgattgagg ctgaggccgc tcatggacc gtcacccgcc actatcggga     17820
gcaccagaag gtgagtgcag ggcatgggc ctcacaatgc ccctctaccc caggggccta     17880
aagcccactg ggctgagggc tggaaggacg agcctgaccc accagcccag gggcgggcag    17940
ctgtatctgg gcagcctcct cactagctgg ctcggctctt gatctccctg caaccccgt     18000 ccccagggcc ggcccaccag caccaacccc atcgccagca tctttgcctg gacacgtggc    18060
ctggagcacc gggggaagct ggatgggaac caagacctca tcaggtgagc atggagggag    18120
aggccggagc tgcccaggac aggctctggg tcctgccctt gcacagatgg ggtctcattc    18180
tgccccatcc ccataggttt gcccagatgc tggagaaggt gtgcgtggag acggtggaga    18240
gtggagccat gaccaaggac ctggcgggct gcattcacgg cctcagcaag tgcgtggcct    18300
ggggtggtag gcagaccctg gggccatgtg ggaggaagcc aggggacccc tcctaaagtc    18360
cccctcatga gtcagcttag ctgcaagggg gcctggggca ggacatgtcc acagccctga    18420
gagactgctc aggccagcct ctgtagacca ggtctagtga gttcctcccc atccctgagg    18480
ctggctactc agagctcctt ccgacccctgc ccacacccct ttcccagctt ctctcaggag   18540
agcagttacc tggcaagaca gaccctgcgg gtgcctgccg aatctcggtg gcctcatggt    18600 aggggggctat agctggcctc tggcctgtag tctgggtggc aggagatggc tgttctgatg    18660
cccaagctca ggctgttccc tggaagggcc tggctgatgg ccttggcaag gcctggagcc    18720
acccctgatg tgagtggtgc tctctctgca gtgtgaagct gaacgagcac ttcctgaaca    18780
ccacggactt cctcgacacc atcaagagca acctggacag agccctgggc aggcagtagg    18840
gggaggcgcc acccatggct gcagtggagg ggccagggct gagccggcgg gtcctcctga    18900
gcgcggcaga gggtgagcct cacagcccct ctctggaggc cttttctaggg gatgtttttt    18960 tataagccag atgttttaa aagcatatgt gtgtttcccc tcatggtgac gtgaggcagg     19020
agcagtgcgt tttacctcag ccagtcagta tgttttgcat actgtaattt atattgccct    19080
tggaacacat ggtgccatat ttagctacta aaaagctctt cacaaaattg tctgctgtgt    19140
ttgtccctga ggggaggagg tagtgggacc ctgaggcaga ggccctgcta gagctggcag    19200
```

```
gttcccctgg ggcagaccag agcacctcag gaaggggctg ccacggcagg gaagggacca    19260
ggcagccctg ggagcccgca ttccacaggg gcccactgcg gagttctcgg acactcaggg    19320
cacaggcctg tgggttccct ggaattttct agcatgatcc agtttctgtg tccagttctc    19380
cattctgaga gtcaatcagt tcctgatagg ttgtcattga ttttttcctt cgttggtttt    19440
aaccttctaa acatctccag gccactttct tagccttttt ctaggtacta aaaagaggtc    19500
ctacccacac ctgcctcaca cttctccttt ccaaggctgc ctgagtttgg aggggcttgg    19560
gtgtgtgtga acaagggccc tgcattgtct aggcctgcag ttcccaggct tgggttcact    19620
ttcaccatgc attggcaaaa ctagaaaagt aagcttgtga caaattgttc tcggccgggc    19680
acagtggcgc acgcctataa tccctgtact ttgggaggct gaggtgggtg gatcacttga    19740
ggccaggagt tcgagaccag cctggccaac atggtgaaac cccatctcta ctcaaaatac    19800
aaaaattagc caggcgtggt gatgcgcacc tgcagtccca gctactcggg aggctgaggc    19860
aggaaaatgg cttgaacctg ggaggcagag gttgcagtga gccgagactg caccactgca    19920
ctccagcctg ggtgacagag caagactctg tctcaaaaaa aaaaaaaaa aaaaaaaaa     19980 aaaaattgct ctatgcaagt tttttagccc catgtaaaaa ggaaaaataa aagttgctct    20040
aaagctacat ataatcaaaa ggactgtcct ctgcatagta agttctgcaa agcttcttct    20100
ttttggtgtt aaaatgtcct ggagaagagt tgtataatct ttataaagtc ctggccaggt    20160
gtggtggctc atgcctatag tcccagcact ttgggaggcc aaggtgggag gatcacttga    20220
gcccgggagt ttgaggctgt agtgagctat gactgcacca ctgtactcca gcctgagtaa    20280
cagagtgaga ccccatctct caaaacccca tcttacaaag tccctttcct aaatactggg    20340
gggactccta tggctcctga aacccgacca ttgcggtaga ctgagtggct ttggaagggc    20400
tctagccctc catccacact ggtgaccccc cgcttgcttt tcctgagtaa tgccctgaaa    20460
ctctcagggc tataagaaga aacgtggact gctggctcta gcaggcccag ccctgggag    20520 gaagctcaag gcttcctgcc tcttcttgcc tgtcaccagc acggggctgg cagctctgca    20580
gaacgcagcc tctgaagccc agcctggcat cgggagctgg cttctttcct gaagccatgt    20640
gggtgggtag ggaggggaag                                                20660
```